(12) United States Patent
Leysen et al.

(10) Patent No.: US 9,073,905 B2
(45) Date of Patent: Jul. 7, 2015

(54) ROCK INHIBITORS

(75) Inventors: Dirk Leysen, Diepenbeek (BE); Olivier Defert, Diepenbeek (BE); Sandro Boland, Diepenbeek (BE); Jo Alen, Diepenbeek (BE); Arnaud Pierre Jean Bourin, Diepenbeek (BE)

(73) Assignee: Amakem NV, Diepenbeek (BE)

( * ) Notice: Subject to any disclaimer, the term of this patent is extended or adjusted under 35 U.S.C. 154(b) by 0 days.

(21) Appl. No.: 14/113,941

(22) PCT Filed: Apr. 27, 2012

(86) PCT No.: PCT/EP2012/057785
§ 371 (c)(1),
(2), (4) Date: Oct. 25, 2013

(87) PCT Pub. No.: WO2012/146724
PCT Pub. Date: Nov. 1, 2012

(65) Prior Publication Data
US 2014/0057942 A1    Feb. 27, 2014

(30) Foreign Application Priority Data
Apr. 29, 2011    (GB) .................................. 1107223.8

(51) Int. Cl.
*C07D 409/14*    (2006.01)
*C07D 401/12*    (2006.01)
(Continued)

(52) U.S. Cl.
CPC ............ *C07D 409/14* (2013.01); *C07D 401/12* (2013.01); *C07D 401/14* (2013.01); *C07D 405/14* (2013.01); *C07D 451/04* (2013.01)

(58) Field of Classification Search
None
See application file for complete search history.

(56) References Cited

U.S. PATENT DOCUMENTS 6,369,086 B1    4/2002    Davis et al.
6,369,087 B1    4/2002    Whittle et al.
(Continued)

FOREIGN PATENT DOCUMENTS

WO    01/56988 A1    8/2001
WO    2007/133622 A2    11/2007
(Continued)

OTHER PUBLICATIONS

Takami, A. et al.; Design and synthesis of Rho kinase inhibitors (I); Bioorganic & Medicinal Chemistry; May 1, 2004; pp. 2115-2137; vol. 12—Issue 9; Elsevier Ltd.
(Continued)

*Primary Examiner* — Zinna Northington Davis
(74) *Attorney, Agent, or Firm* — Dinsmore & Shohl LLP

(57) ABSTRACT

The present invention relates to new kinase inhibitors of Formula (I), wherein X is oxygen, —NH—, or a direct bond; Y is —NH— or a direct bond; n is an integer from 0 to 4; m is an integer from 0 to 4; Cy represents a bivalent radical consisting of a satured (poly)cycle, including fused, bi-, spiro or bridged carbocycles and heterocycles; in particular selected from the group consisting of: Formula (II), Ar is selected from the group comprising: Formula (III), $R^2$ is hydrogen or methyl; $R^8$ is hydrogen, methyl, halogen, or alkynyl; $R^1$ is an aryl or heteroaryl more specifically ROCK inhibitors, compositions, in particular pharmaceuticals, comprising such inhibitors, and to uses of such inhibitors in the treatment and prophylaxis of disease. In particular, the present invention relates to new ROCK inhibitors, compositions, in particular pharmaceuticals, comprising such inhibitors, and to uses of such inhibitors in the treatment and prophylaxis of disease. In addition, the invention relates to methods of treatment and use of said compounds in the manufacture of a medicament for the application to a number of therapeutic indications including sexual dysfunction, inflammatory diseases, ophthalmic diseases and Respiratory diseases.

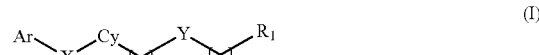

(I)

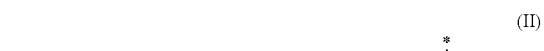

(II)

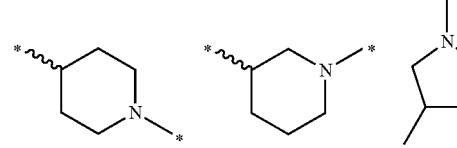

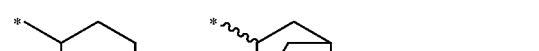

(III)

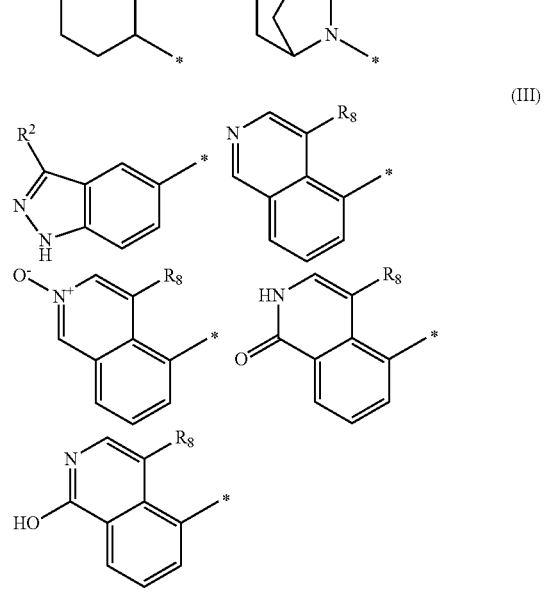

13 Claims, 1 Drawing Sheet

(51) Int. Cl.
*C07D 401/14* (2006.01)
*C07D 405/14* (2006.01)
*C07D 451/04* (2006.01)
*A61K 31/4725* (2006.01)
*A61K 31/439* (2006.01)
*A61K 31/4468* (2006.01)

(56) References Cited

U.S. PATENT DOCUMENTS

| | | |
|---|---|---|
| 6,372,733 B1 | 4/2002 | Caldwell et al. |
| 6,372,778 B1 | 4/2002 | Tung et al. |
| 2008/0214614 A1 | 9/2008 | Lampe et al. |
| 2009/0325959 A1 | 12/2009 | Vittitow et al. |
| 2009/0325960 A1 | 12/2009 | Fulcher et al. |
| 2010/0022517 A1 | 1/2010 | Richards et al. |

FOREIGN PATENT DOCUMENTS

| | | |
|---|---|---|
| WO | 2008/049919 A2 | 5/2008 |
| WO | 2008/077057 A2 | 6/2008 |
| WO | 2009/158587 A1 | 12/2009 |
| WO | 2010/065782 A1 | 6/2010 |
| WO | 2012/015760 A1 | 2/2012 |

OTHER PUBLICATIONS

Iwakubo, M. et al.; Design and synthesis of Rho kinase inhibitors (II); Bioorganic & Medicinal Chemistry; Jan. 1, 2007; pp. 350-364; vol. 15—Issue 1; Elsevier Ltd.

Iwakubo, M. et al.; Design and synthesis of Rho kinase inhibitors (III); Bioorganic & Medicinal Chemistry; Jan. 15, 2007; pp. 1022-1033; vol. 15—Issue 2; Elsevier Ltd.

International Search Report and Written Opinion dated Nov. 23, 2012 pertaining to International application No. PCT/EP2012/057785.

International Preliminary Report on Patentability dated Jul. 2, 2013 pertaining to International application No. PCT/EP2012/057785.

Segain, et al., "Rho Kinase Blockade Prevents Inflammation Via Nuclear Factor KB Inhibition: Evidence in Crohn's Disease and Experimental Colitis", Rapid Communications, Gastroenterology 2003 vol. 124, pp. 1180-1187.

ROCK INHIBITORS

CONTINUING DATA

This application is a 371 of PCT/EP2012/057785 filed Apr. 27, 2012.

FIELD OF THE INVENTION

The present invention relates to new kinase inhibitors, more specifically ROCK inhibitors, compositions, in particular pharmaceuticals, comprising such inhibitors, and to uses of such inhibitors in the treatment and prophylaxis of disease. In particular, the present invention relates to new ROCK inhibitors, compositions, in particular pharmaceuticals, comprising such inhibitors, and to uses of such inhibitors in the treatment and prophylaxis of disease.

BACKGROUND OF THE INVENTION

The serine/threonine protein kinase ROCK consists in humans of two isoforms ROCK I and ROCK II. ROCK I is encoded on chromosome 18 whereas ROCK II, also called Rho-kinase, is located on chromosome 12. They both have a molecular weight close to 160 kDa. They share an overall homology of 65% while being 95% homologous in their kinase domains. Despite their sequence similarity, they differ by their tissue distributions. The highest levels of expression for ROCK I are observed in heart, lung and skeletal tissues whereas ROCK II is mostly expressed in brain. Recent data indicate that these two isoforms are partially function redundant, ROCK I being more involved in immunological events, ROCK II in smooth muscle function. The term ROCK refers to ROCK I (ROK-β, p160ROCK, or Rho-kinase β) and ROCK II (ROCK-α or Rho-kinase α).

ROCK activity has been shown to be enhanced by GTPase RhoA that is a member of the Rho (Ras homologous) GTP-binding proteins. The active GTP-bound state of RhoA interacts with Rho-binding domain (RBD) of ROCK that is located in an autoinhibitory carboxyl-terminal loop. Upon binding, the interactions between the ROCK negative regulatory domain and the kinase domain are disrupted. The process enables the kinase to acquire an open conformation in which it is fully active. The open conformation is also induced by the binding of lipid activators such as arachidonic acid to the PH domain in the kinase carboxyl-terminal domain. Another activation mechanism has been described during apoptosis and involves the cleavage of carboxyl terminus by caspase-3 and -2 (or granzyme B) for ROCK I and II, respectively.

ROCK plays an important role in various cellular functions such as smooth muscle contraction, actin cytoskeleton organization, platelet activation, downregulation of myosin phosphatase cell adhesion, -migration, -proliferation and survival, thrombin-induced responses of aortic smooth muscle cells, hypertrophy of cardiomyocytes, bronchial smooth muscle contraction, smooth muscle contraction and cytoskeletal reorganization of non-muscle cells, activation of volume-regulated anion channels, neurite retraction, wound healing, cell transformation and gene expression. ROCK also acts in several signaling pathways that are involved in auto-immunity and inflammation. ROCK has been shown to play a part in the activation of NF-κB, a critical molecule that leads to the production of TNF and other inflammatory cytokines. ROCK inhibitors are reported to act against TNF-alpha and IL-6 production in lipopolysaccharide (LPS)-stimulated THP-1 macrophages. Therefore, ROCK inhibitors provide a useful therapy to treat autoimmune and inflammatory diseases as well as oxidative stress.

ROCK also plays an important role in numerous critical cellular processes involved in angiogenesis. These include stress fiber formation, endothelial cell (EC) polarity, EC adhesion, EC motility, cytokinesis, and apoptosis. Previous studies already showed that Rho-signaling is essential for vascular endothelial growth factor (VEGF)-dependent in vitro capillary formation and in vivo angiogenesis. This suggests that Rho/ROCK inhibition may be a new way to treat angiogenesis-related disorders, such as neovascularization of the cornea or age-related macular degeneration.

In conclusion, ROCK is a major control point in smooth muscle cell function and a key signaling component involved in inflammatory processes in various inflammatory cells as well as fibrosis and remodeling in many diseased organs. In addition, ROCK has been implicated in various diseases and disorders including eye diseases; airway diseases; cardiovascular and vascular diseases; inflammatory diseases; neurological and CNS disorders: proliferative diseases; kidney diseases; sexual dysfunction; blood diseases; bone diseases; diabetes; benign prostatic hyperplasia, transplant rejection, liver disease, systemic lupus erythmatosis, spasm, hypertension, chronic obstructive bladder disease, premature birth, infection, allergy, obesity, pancreatic disease and AIDS.

ROCK appears to be a relatively safe target, as exemplified by knockout models and a large number of academic studies. These KO mice data, in combination with post-marketing surveillance studies with Fasudil, a moderately potent ROCK inhibitor used for the treatment of vasospasm after subarachnoid hemorrhage, indicate that ROCK is a genuine and significant drug target.

ROCK inhibitors would be useful as therapeutic agents for the treatment of disorders implicated in the ROCK pathway. Accordingly, there is a great need to develop ROCK inhibitors that are useful in treating various diseases or conditions associated with ROCK activation, particularly given the inadequate treatments currently available for the majority of these disorders. Some non-limiting examples are glaucoma, asthma and COPD.

Glaucoma is a neurodegenerative disease that is the second most important cause of irreversible blindness. This disease is characterized by a raised intra-ocular pressure (IOP) and by progressive retinal ganglion cell apoptosis, resulting in irreversible visual field loss. Current treatment of this disease is directed towards the reduction of IOP, which is the main—but not only—risk factor for glaucoma. There is a need for improved treatment as the current therapy does only control and not cure the disease and further causes irritation, local and systemic side effects. In addition, additional positive effects, such as the anti-inflammatory and nerve regenerating components of ROCK inhibitors, would be highly preferred. Reference ROCK inhibitors, such as Y-27632 cause changes in cell shape and decrease stress fibers, focal adhesions and MLC phosphorylation in cultured human TM cells; they relax human trabecular meshwork in vitro, relax human Schlemm's canal endothelial cells in vitro and when topically applied to animals give a significant increase in trabecular outflow, resulting into a strong lowering of intra ocular pressure.

Allergic asthma is a chronic inflammatory airway disorder that results from maladaptive immune responses to ubiquitous environmental proteins in genetically susceptible persons. Despite reasonably successful therapies, the prevalence of allergic asthma increases as these therapies do not cure; there are still exacerbations and an increasing number of non-responders. New, effective and steroid-sparing treatments that tackle all components of the disease are required.

Age-related macular degeneration (AMD) is the leading cause of visual loss in the elderly population. Wet or neovascular AMD leads to rapid, devastating visual loss due to choroidal neovascularization (CNV), macular edema and photoreceptor cell death. Nowadays, anti-Vascular Endothelial Growth Factor (VEGF) therapy constitutes the first line of therapy for active CNV in wet AMD. VEGF promotes angiogenesis and vascular permeability and plays an important role in CNV formation. Different drugs aimed at blocking VEGF or its receptors have been developed. Besides neovascularization, the pathogenesis of AMD also comprises inflammation and scarring. A recent preclinical study showed that anti-VEGF treatment is restricted to reduction of angiogenesis, and can even give rise to inflammation and scarring. Another big concern is that anti-VEGF can give rise to major systemic side effects due to regression of blood vessels and neurodegeneration, as well as local side effects. So there is a need for alternative treatment modalities. Previous studies already showed that pharmacological inhibition of ROCK1 and ROCK2 by Y-27632 strongly disrupts angiogenesis and that ROCK-inhibition reduces inflammation and scarring. Therefore, ROCK-inhibitors might be an attractive and improved alternative to anti-VEGF therapies for the treatment of wet AMD.

Chronic Obstructive Pulmonary Disease (COPD) represents a group of diseases characterized by irreversible limitation of airflow, associated with abnormal inflammatory response, bronchoconstriction and remodeling and destruction of the tissue of the lung. It is one of the leading causes of death worldwide, with a steadily increasing prevalence. There is an urgent need for novel therapeutic approaches as the current regimen is inadequate. The current treatment is essentially based on bronchodilators, since glucocorticoids have limited or no effect. ROCK inhibitors could provide new treatment strategies for COPD. Reference ROCK inhibitors, such as Y-27632 relax human isolated bronchial preparations, inhibit increases in airway resistance in anaesthetised animals, potentiate relaxing effects of β-agonists in vitro and in vivo and give rapid bronchodilatation upon inhalation. In addition, ROCK inhibitors block tracheal smooth muscle contractions induced by $H_2O_2$, the clinical marker for oxidative stress. Related to airway inflammation, ROCK inhibitors counteract the increase in trans-endothelial permeability mediated by inflammatory agents, maintain the endothelial barrier integrity, inhibit the influx of eosinophils after ovalbumin challenge in vivo, protect against lung edema formation and neutrophile migration, suppress airway HR to metacholine and serotonin in allergic mice and block LPS-induced TNF release. With respect to airway fibrosis and remodeling, ROCK inhibitors block the induced migration of airway smooth muscle cells. In vitro evidences for the role of ROCK in airway remodeling were obtained in human lung carcinoma cell line, bovine tracheal smooth muscle cells and human airway smooth muscle. In vivo proof for a role of ROCK in fibrosis in general was generated with mice which exhibited attenuated myocardial fibrosis in response to the partial deletion of ROCK. The attenuation of myocardial fibrosis by Y-27632 in response to myocardial infarction and by fasudil in the case of congestive heart failure in a chronic hypertensive rat model brings additional indications of ROCK importance in remodeling. Finally, ROCK inhibitors increase apoptotic cell loss of smooth muscle cells.

Several different classes of ROCK inhibitors are known. The current focus is oncology and cardiovascular applications. Until now, the outstanding therapeutic potential of ROCK inhibitors has only been explored to a limited extent. The reason is the fact that ROCK is such a potent and widespread biochemical regulator, that systemic inhibition of ROCK leads to strong biological effects that are considered as being side effects for the treatment of most of the diseases. Indeed, the medical use of ROCK inhibitors to treat diseases with a strong inflammatory component is hampered by the pivotal role of ROCK in the regulation of the tonic phase of smooth muscle cell contraction. Systemically available ROCK inhibitors induce a marked decrease in blood pressure. Therefore, ROCK inhibitors with different properties are highly required.

For the target specific treatment of disorders by regulating smooth muscle function and/or inflammatory processes and/or remodeling, it is highly desired to deliver a ROCK inhibitor to the target organ and to avoid significant amounts of these drugs to enter other organs. Therefore, local or topical application is desired. Typically, topical administration of drugs has been applied for the treatment of airway-, eye, sexual dysfunction and skin disorders. In addition, local injection/infiltration into diseased tissues further extend the potential medical use of locally applied ROCK inhibitors. Given certain criteria are fulfilled, these local applications allow high drug concentration to be reached in the target tissue. In addition, the incorporation of ROCK inhibitors into implants and stents can further expand the medical application towards the local treatment of CV diseases such as atherosclerosis, coronary diseases and heart failure.

Despite the fact that direct local application is preferred in medical practice, there are still concerns regarding drug levels reached into the systemic circulation. For example the treatment of airway diseases by local delivery by for instance inhalation, poses the risk of systemic exposure due to large amounts entering the GI tract and/or systemic absorption through the lungs. For the treatment of eye diseases by local delivery, also significant amounts enter the GI tract and/or systemic circulation due to the low permeability of the cornea, low capacity for fluid, efficient drainage and presence of blood vessels in the eyelids. Also for dermal applications, local injections and implantable medical devices, there is a severe risk of leakage into the systemic circulation. Therefore, in addition to local application, the compounds should preferably have additional properties to avoid significant systemic exposure.

Soft drugs are biologically active compounds that are inactivated once they enter the systemic circulation. This inactivation involves the controlled conversion of said soft drug towards a predictable metabolite displaying markedly reduced functional activity or, preferably, negligible functional activity. Inactivation can be achieved in the liver, but the preferred inactivation should occur in the blood. These compounds, once applied locally to the target tissue/organ exert their desired effect locally. When they leak out of the target tissue into the systemic circulation, they are very rapidly inactivated. Thus, soft drugs of choice are sufficiently stable in the target tissue/organ to exert the desired biological effect, but are rapidly degraded in the blood to biologically inactive compounds. Soft drug therefore allow for reduced systemic exposure to a functionally active drug compound. In addition, it is highly preferable that the soft drugs of choice have retention at their biological target. This property will limit the number of daily applications and is highly desired to reduce the total load of drug and metabolites and in addition will significantly increase the patient compliance. Soft drugs should not be confused with prodrugs, which undergo controlled conversion towards a functionally active metabolite and whom purpose is usually to provide increased exposure to a functionally active compound.

In view of the high potential of ROCK inhibitors for generating undesirable side effects, it will be appreciated that soft drug approaches represent an attractive way of generating ROCK inhibitors with improved properties; in particular ROCK inhibitors associated with reduced systemic exposure and therefore lower potential for undesirable side effects.

Although soft drugs represent an attractive approach for the inhibition of ROCK and the treatment of ROCK-associated diseases or conditions, the design and optimization of such compounds is not trivial. Successful soft drugs have to retain strong on-target potency and functional efficacy. Additionally, successful soft drugs should display good stability at the intended site of action (eg eye or lung), so that a pharmacologically relevant concentration of the drug can be reached and maintained for a prolonged period of time (typically several hours) at this intended site of action. Furthermore, successful soft drugs should be rapidly degraded once they enter systemic circulation, so that systemic exposure and the undesired side effects associated with systemic exposure are avoided. Finally, the molecule(s) resulting from the degradation of the soft drug should display markedly reduced, preferably negligible functional activity. As a result, the design and optimization of molecules successfully combining all of these aspects represents a significant technical problem. In conclusion, there is a continuing need to design and develop soft ROCK inhibitors for the treatment of a wide range of disease states.

The compounds described herein are soft ROCK inhibitors and solve the technical problem of successfully combining strong on-target and functional efficacy, good stability in target organs (such as, but not limited to, eye or lung) and rapid conversion in blood towards a predictable, functionally inactive species. The compounds described herein and pharmaceutically acceptable compositions thereof are useful for treating or lessening the severity of a variety of disorders or conditions associated with ROCK activation. More specifically, the compounds of the invention are preferably used in the prevention and/or treatment of at least one disease or disorder, in which ROCK is involved, such as diseases linked to smooth muscle cell function, inflammation, fibrosis, excessive cell proliferation, excessive angiogenesis, hyperreactivity, barrier dysfunction, neurodegeration and remodeling. For example, the compounds of the invention may be used in the prevention and/or treatment of diseases and disorders such as:

Eye diseases or disorders: including but not limited to retinopathy, optic neuropathy, glaucoma and degenerative retinal diseases such as macular degeneration, proliferative vitreoretinopathy, proliferative diabetic retinopathy, retinitis pigmentosa and inflammatory eye diseases, glaucoma filtration surgery failure, dry eye, allergic conjunctivitis, posterior capsule opacification, abnormalities of corneal wound healing and ocular pain.

Airway diseases; including but not limited to pulmonary fibrosis, emphysema, chronic bronchitis, asthma, fibrosis, pneumonia, cytsic fibrosis, chronic obstructive pulmonary disease (COPD); bronchitis and rhinitis and respiratory distress syndrome Throat, Nose and Ear diseases: including but not limited to sinus problems, hearing problems, toothache, tonsillitis, ulcer and rhinitis, Skin diseases: including but not limited to hyperkeratosis, parakeratosis, hypergranulosis, acanthosis, dyskeratosis, spongiosis and ulceration.

Intestinal diseases; including but not limited to inflammatory bowel disease (IBD), colitis, gastroenteritis, ileus, ileitis, appendicitis and Crohn's disease.

Cardiovascular and vascular diseases: including but not limited to, pulmonary hypertension and pulmonary vasoconstriction.

Inflammatory diseases: including but not limited to contact dermatitis, atopic dermatitis, psoriasis, rheumatoid arthritis, juvenile rheumatoid arthritis, ankylosing spondylitis, psoriatic arthritis, inflammatory bowel disease, Crohn's disease and ulcerative colitis.

Neurological disorders: including but not limited to neuropathic pain. The present compounds are therefore suitable for preventing neurodegeneration and stimulating neurogeneration in various neurological disorders.

Proliferative diseases: such as but not limited to cancer of, breast, colon, intestine, skin, head and neck, nerve, uterus, kidney, lung, ovary, pancreas, prostate, or thyroid gland; Castleman disease; sarcoma; malignoma; and melanoma.

Kidney diseases: including but not limited to renal fibrosis or renal dysfunction Sexual dysfunction: is meant to include both male and female sexual dysfunction caused by a defective vasoactive response. The soft ROCK inhibitors of the present invention may also be used to treat sexual dysfunction arising from a variety of causes. For example, in an embodiment, the soft ROCK inhibitors may be used to treat sexual dysfunction associated with hypogonadism and more particularly, wherein the hypogonadism is associated with reduced levels of androgen hormones. In another embodiment, the soft ROCK inhibitors may be used to treat sexual dysfunction associated with a variety of causes including, but not limited to, bladder disease, hypertension, diabetes, or pelvic surgery. In addition, the soft ROCK inhibitors may be used to treat sexual dysfunction associated with treatment using certain drugs, such as drugs used to treat hypertension, depression or anxiety.

Bone diseases: including but not limited to osteoporosis and osteoarthritis

In addition, the compounds of the invention may be used in the prevention and/or treatment of diseases and disorders such as benign prostatic hyperplasia, transplant rejection, spasm, chronic obstructive bladder disease, and allergy.

SUMMARY OF THE INVENTION

We have surprisingly found that the compounds described herein act as inhibitors of ROCK, in particular as soft ROCK inhibitors. Compared to prior art known ROCK inhibitors, such as for example described in WO2008/077057, WO2010/065782, WO2009/158587, US2009/0325959, US2009/0325960, Iwakubo et al. (*Bioorg. Med. Chem.*, 2007, 15, 350-364 & *Bioorg. Med. Chem.*, 2007, 15, 1022-1033) and WO2001/56988, the compounds of the present invention differ in that they are very rapidly converted into predictable functionally inactive compounds when entering systemic circulation, yet retain good stability in target organs. Compound inactivation can occur in the liver, but is preferentially achieved directly in the blood flow, through blood enzymes, for example carboxylic ester hydrolases (EC 3.1.1) such as Cholinesterases, Paraoxonase 1 (PON1) or plasma proteins displaying pseudoesterase activity such as Human serum albumin. The compounds of the present invention therefore solve the technical problem of successfully combining on-target potency (inhibitory activity against ROCK) and functional efficacy, good stability in target organs and rapid conversion in blood towards a predictable, functionally inactive species. As a result, the compounds of the invention can achieve a desired pharmacological effect through inhibition of ROCK at the intended site of action (e.g. eye or lung), while avoiding a systemic inhibition of ROCK that would create potential for side effects.

Carboxylic ester hydrolases (EC 3.1.1) represent a large group of enzymes involved in the degradation of carboxylic esters into alcohols and carboxylic acids. As such, enzymes displaying this catalytic activity are of potential interest for the design of soft kinase inhibitors. EC 3.1.1 includes the following sub-classes: EC 3.1.1.1 carboxylesterase, EC 3.1.1.2 arylesterase, EC 3.1.1.3 triacylglycerol lipase, EC 3.1.1.4 phospholipase A2, EC 3.1.1.5 lysophospholipase, EC 3.1.1.6 acetylesterase, EC 3.1.1.7 acetylcholinesterase, EC 3.1.1.8 cholinesterase, EC 3.1.1.10 tropinesterase, EC 3.1.1.11 pectinesterase, EC 3.1.1.13 sterol esterase, EC 3.1.1.14 chlorophyllase, EC 3.1.1.15 L-arabinonolactonase, EC 3.1.1.17 gluconolactonase, EC 3.1.1.19 uronolactonase, EC 3.1.1.20 tannase, EC 3.1.1.21 retinyl-palmitate esterase, EC 3.1.1.22 hydroxybutyrate-dimer hydrolase, EC 3.1.1.23 acylglycerol lipase, EC 3.1.1.24 3-oxoadipate enol-lactonase, EC 3.1.1.25 1,4-lactonase, EC 3.1.1.26 galactolipase, EC 3.1.1.27 4-pyridoxolactonase, EC 3.1.1.28 acylcarnitine hydrolase, EC 3.1.1.29 aminoacyl-tRNA hydrolase, EC 3.1.1.30 D-arabinonolactonase, EC 3.1.1.31 6-phosphogluconolactonase, EC 3.1.1.32 phospholipase A1, EC 3.1.1.33 6-acetylglucose deacetylase, EC 3.1.1.34 lipoprotein lipase, EC 3.1.1.35 dihydrocoumarin hydrolase, EC 3.1.1.36 limonin-D-ring-lactonase, EC 3.1.1.37 steroid-lactonase, EC 3.1.1.38 triacetate-lactonase, EC 3.1.1.39 actinomycin lactonase, EC 3.1.1.40 orsellinate-depside hydrolase, EC 3.1.1.41 cephalosporin-C deacetylase, EC 3.1.1.42 chlorogenate hydrolase, EC 3.1.1.43 α-amino-acid esterase, EC 3.1.1.44 4-methyloxaloacetate esterase, EC 3.1.1.45 carboxymethylenebutenolidase, EC 3.1.1.46 deoxylimonate A-ring-lactonase, EC 3.1.1.471-alkyl-2-acetylglycerophosphocholine esterase, EC 3.1.1.48 fusarinine-C ornithinesterase, EC 3.1.1.49 sinapine esterase, EC 3.1.1.50 wax-ester hydrolase, EC 3.1.1.51 phorbol-diester hydrolase, EC 3.1.1.52 phosphatidylinositol deacylase, EC 3.1.1.53 sialate O-acetylesterase, EC 3.1.1.54 acetoxybutynylbithiophene deacetylase, EC 3.1.1.55 acetylsalicylate deacetylase, EC 3.1.1.56 methylumbelliferyl-acetate deacetylase, EC 3.1.1.57 2-pyrone-4,6-dicarboxylate lactonase, EC 3.1.1.58 N-acetylgalactosaminoglycan deacetylase, EC 3.1.1.59 juvenile-hormone esterase, EC 3.1.1.60 bis(2-ethylhexyl)phthalate esterase, EC 3.1.1.61 protein-glutamate methylesterase, EC 3.1.1.63 11-cis-retinyl-palmitate hydrolase, EC 3.1.1.64 all-trans-retinyl-palmitate hydrolase, EC 3.1.1.65 L-rhamnono-1,4-lactonase, EC 3.1.1.66 5-(3,4-diacetoxybut-1-ynyl)-2,2'-bithiophene deacetylase, EC 3.1.1.67 fatty-acyl-ethyl-ester synthase, EC 3.1.1.68 xylono-1,4-lactonase, EC 3.1.1.70 cetraxate benzylesterase, EC 3.1.1.71 acetylalkylglycerol acetylhydrolase, EC 3.1.1.72 acetylxylan esterase, EC 3.1.1.73 feruloyl esterase, EC 3.1.1.74 cutinase, EC 3.1.1.75 poly(3-hydroxybutyrate) depolymerase, EC 3.1.1.76 poly(3-hydroxyoctanoate) depolymerase, EC 3.1.1.77 acyloxyacyl hydrolase, EC 3.1.1.78 polyneuridine-aldehyde esterase, EC 3.1.1.79 hormone-sensitive lipase, EC 3.1.1.80 acetylajmaline esterase, EC 3.1.1.81 quorum-quenching N-acyl-homoserine lactonase, EC 3.1.1.82 pheophorbidase, EC 3.1.1.83 monoterpene ϵ-lactone hydrolase, EC 3.1.1.84 cocaine esterase, EC 3.1.1.85 mannosylglycerate hydrolase An example of carboxylic ester hydrolase is PON1. PON1 is a $Ca^{2+}$ dependent serum class A esterase, which is synthesized in the liver and secreted in the blood, where it associates exclusively with high-density lipoproteins (HDLs). Furthermore, it is able to cleave a unique subset of substrates including organophosphates, arylesters, lactones and cyclic carbonates. Therefore, the $R^1$ substituent of the compounds of the present invention, generally represented by formula I hereinbelow, can be selected to comprise a substituent selected from the group of arylesters, lactones and cyclic carbonates, more specifically from arylesters and lactones.

Human serum albumin (HSA) is a major component of blood plasma, accounting for approximately 60% of all plasma proteins. HSA has been found to catalyze the hydrolysis of various compounds such as aspirin, cinnamoylimidazole, p-nitrophenyl acetate, organophosphate insecticides, fatty acid esters or nicotinic esters. HSA diplays multiple nonspecific catalytic sites in addition to its primary reactive site. The catalytic efficiency of these sites is however low, and HSA has often been described not as a true esterase, but as a pseudoesterase, In spite of its low catalytic efficiency, HSA can still play a significant role in the metabolism of drug-like compounds, because of its high concentration in plasma.

It will be understood by those skilled in the art that a major technical problem in the design of soft drugs, including soft ROCK inhibitors, is to successfully combine strong on-target potency and functional activity, good stability in the target organ and rapid degradation in the systemic circulation, towards a functionally inactive species. In order to produce the desired effect(s) in the target organ, soft ROCK inhibitors should achieve a pharmacologically relevant concentration in said target organ and maintain this concentration during a prolonged period of time, typically several hours. In order to avoid systemic inhibition of ROCK, which could potentially lead to undesired effects, soft ROCK inhibitors should be rapidly degraded once entering the systemic circulation, before they can build up a pharmacologically relevant concentration in the blood flow or in non-target organs.

It will also be understood by those skilled in the art that inhibition of ROCK results from recognition (complementary interactions) between ROCK and the soft ROCK inhibitor, while inactivation of the soft ROCK inhibitor in liver or the blood flow results from said soft ROCK inhibitor being recognized as a substrate by one or more liver or blood enzymes, for instance carboxylic ester hydrolases (EC 3.1.1). As these two recognition processes involve independent macromolecules (ROCK and the hydrolase(s)) and therefore independent ligand-binding sites, the structural features governing such recognition processes are also independent from each other and are not necessarily compatible. It will therefore be understood that the inhibitory activity of a chemical compound against ROCK is in no way predictive of its (in) stability in systemic circulation.

As discussed hereinabove, a successful soft ROCK inhibitor simultaneously needs to display low stability in the systemic circulation, but also good stability in the target organ. It will be understood by those skilled in the art that such a difference of stability between different organs and fluids can result from different enzymes (in particular esterases) being present in these tissues or fluids, from different expression levels ("concentrations") of the same enzyme, or from both. It will also be understood that each additional enzyme, including esterases, present in the organ or fluid represents a new ligand-binding site with its own set of rules governing recognition as a substrate. Such rules are not necessarily compatible with each other, usually resulting in most enzymes displaying some degree of substrate specificity. In order to achieve acceptable stability in the target organ, a successful soft ROCK inhibitor should therefore avoid, at least up to a certain point, being recognized as a substrate by the degrading enzymes, including carboxylic ester hydrolases, which are present in significant quantities in the target organ. Once again, it will be understood that the inhibitory activity of a chemical compound against ROCK is in no way predictive of its (in)stability in the target organ. Additionally, it will be understood that as the potential degradation mechanisms in liver, blood flow and target organ can involve different enzymes; (in)stability in the liver or blood flow is in no way predictive of (in)stability in the target organ.

In view of the above, it will be understood that the design of a soft ROCK inhibitor displaying the appropriate activity and stability profile represents a significant technical problem to be solved. In particular, it will be understood that inhibitory activity against ROCK and stability in liver, blood flow or target organ are governed by independent sets of structural rules, making the design of a successful soft ROCK inhibitor non-obvious.

It will also be understood by those skilled in the art that soft drugs and prodrugs represent opposite approaches in their conception and purpose, even though both approaches involve the controlled and predictable metabolism of an administered compound. Indeed, a soft drug is a chemical compound with strong functional activity, which undergoes controlled metabolism towards a functionally inactive and therefore nontoxic species. The purpose of a soft drug is to decrease systemic exposure to a functionally active compound and to direct the metabolism and elimination of this drug compound towards a predictable route, leading to a functionally inactive, nontoxic metabolite. By opposition, a prodrug is a chemical compound that does not necessarily possess functional activity, but undergoes controlled metabolism towards a functionally active compound. The purpose of a prodrug is to increase exposure to a functionally active compound, for example because the prodrug displays higher cellular permeability, higher bioavailability, or allows the sustained release of a functionally active compound which is otherwise rapidly cleared from the blood flow.

Unless a context dictates otherwise, asterisks are used herein to indicate the point at which a mono- or bivalent radical depicted is connected to the structure to which it relates and of which the radical forms part.

Viewed from a first aspect, the invention provides a compound of Formula I or a stereoisomer, tautomer, racemic, salt, hydrate, or solvate thereof,

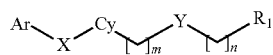

(I)

Wherein

X is oxygen, —NH— or a direct bond;

Y is —NH— or a direct bond;

n is an integer from 0 to 4;

m is an integer from 0 to 4;

Cy represents a bivalent radical consisting of a satured (poly) cycle, including fused, bi-, spiro or bridged carbocycles and heterocycles; in particular selected from the group consisting of:

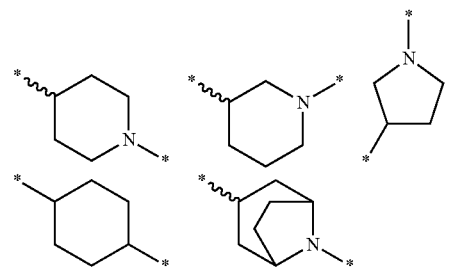

Ar is selected from the group comprising:

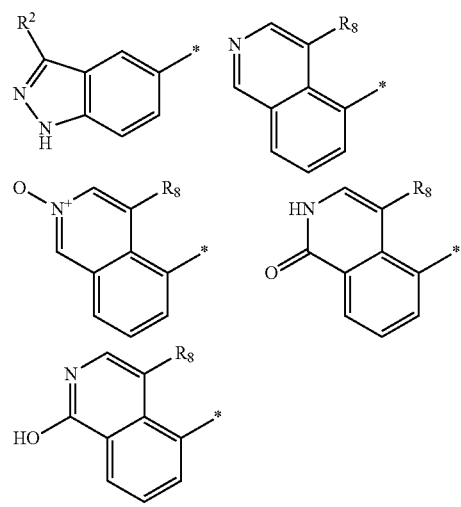

Wherein $R^2$ is hydrogen or methyl;

$R^8$ is hydrogen, methyl, halogen, or alkynyl;

$R^1$ is an aryl or heteroaryl optionally substituted with halo or $C_{1-6}$alkyl; wherein said aryl or heteroaryl is substituted with a substituent selected from the group consisting of:
- —$(CH_2)_p$—C(=O)—$OR^{21}$;
- —$(CH_2)_p$—C(=O)—$NR^3R^4$;
- —$(CH_2)_p$—C(=O)—$SR^{22}$;
- $Het^1$, —O-$Het^1$, —NH-$Het^1$, or —S-$Het^1$; and
- —O—$C_{1-6}$alkyl, —NH—$C_{1-6}$alkyl, —S—$C_{1-6}$alkyl, or —$C_{1-6}$alkyl; wherein said —O—$C_{1-6}$alkyl, —NH—$C_{1-6}$alkyl, —S—$C_{1-6}$alkyl, or —$C_{1-6}$alkyl are each independently substituted with a substituent selected from the group consisting of —C(=O)—$OR^{21}$, —C(=O)—$NR^3R^4$, $Het^1$, —O-$Het^1$, —NH-$Het^1$, and —S-$Het^1$;

Wherein p is an integer from 0 to 3

$Het^1$ is selected from the group consisting of:

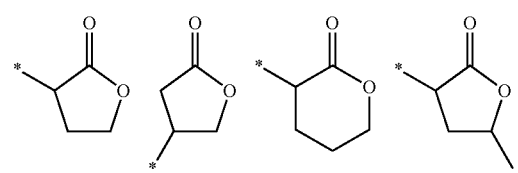

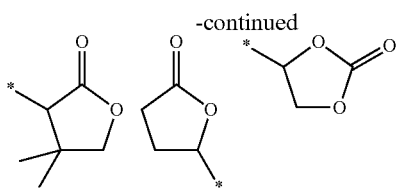

$R^{21}$ is selected from the group consisting of optionally substituted $C_{1-20}$alkyl, optionally substituted $C_{1-20}$alkenyl, optionally substituted $C_{1-20}$alkynyl, optionally substituted $C_{3-15}$cycloalkyl, optionally substituted aryl, optionally substituted heterocyclyl, and optionally substituted heteroaryl;

$R^{22}$ is optionally substituted $C_{1-6}$alkyl;

$R^3$ is selected from the group consisting of Het¹, $C_{1-20}$alkyl, aryl or heteroaryl; wherein said $C_{1-20}$alkyl, aryl or heteroaryl is substituted with 1, 2 or 3 substituents each independently selected from the group consisting of aryl, heteroaryl, —(CH$_2$)$_p$—C(=O)—OR²¹, -Het¹, —NH-Het¹, —O-Het¹, —S-Het¹, —S—C$_{2-6}$alkyl, —NH—C$_{2-6}$alkyl, and —O—C$_{2-6}$alkyl;

Wherein said aryl, heteroaryl, —O—C$_{2-6}$alkyl, —NH—C$_{2-6}$alkyl, or —S—C$_{2-6}$alkyl are each independently substituted with a substituent selected from the group consisting of C(=O)—OR²¹, -Het¹, —O-Het¹, —NH-Het¹, and —S-Het¹; and $R^4$ is selected from the group consisting of hydrogen or $C_{1-6}$alkyl; or $R^3$ and $R^4$ together with the nitrogen atom to which they are attached form a heterocycle substituted with one substituent selected from the group consisting of $C_{1-20}$alkyl, aryl or heteroaryl; wherein said $C_{1-20}$alkyl, aryl, or heteroaryl is substituted with 1, 2 or 3 substituents each independently selected from the group consisting of aryl, heteroaryl, —C(=O)—OR²¹, -Het¹, —O-Het¹, —S-Het¹, —NH—C$_{2-6}$alkyl, and —O—C$_{2-6}$alkyl;

Wherein said —O—C$_{2-6}$alkyl, —NH—C$_{2-6}$alkyl, or —S—C$_{2-6}$alkyl are each independently substituted with a substituent selected from the group consisting of C(=O)—OR²¹, -Het¹, —O-Het¹, —NH-Het¹, and —S-Het¹;

with the proviso that $R^1$ can not be selected from aryl or heteroaryl substituted with —O—CH$_2$—C(=O)—OR²¹;

if $R^1$ is phenyl, then said phenyl can not be substituted with —(CH$_2$)$_p$—C(=O)—OR²¹ in the para position; and said compound of formula I is not

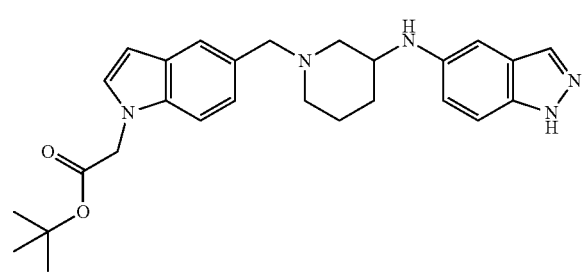 [SMILES: CC(C)(C)OC(=O)Cn1ccc2cc(CN3CCCC(Nc4ccc5[nH]ncc5c4)C3)ccc21]

As can be seen from the above, all compounds of formula I contain at least one ester, thioester, cyclic ester or cyclic carbonate group due to the incorporation of at least one group selected from —C(=O)—OR²¹, —C(=O)—SR²², and Het¹.

Viewed from a further aspect, the invention provides the use of a compound of the invention, or a composition comprising such a compound, for inhibiting the activity of at least one kinase, in vitro or in vivo.

Viewed from a further aspect, the invention provides the use of a compound of the invention, or a composition comprising such a compound, for inhibiting the activity of at least one ROCK kinase, for example ROCKII and/or ROCKI isoforms; in vitro or in vivo.

Viewed from a further aspect, the invention provides a pharmaceutical and/or veterinary composition comprising a compound of the invention.

Viewed from a still further aspect, the invention provides a compound of the invention for use in human or veterinary medicine.

Viewed from a still further aspect, the invention provides the use of a compound of the invention in the preparation of a medicament for the prevention and/or treatment of at least one disease and/or disorder selected from the group comprising eye diseases; airway diseases; throat, nose and ear diseases; intestinal diseases; cardiovascular and vascular diseases; inflammatory diseases; neurological and CNS disorders: proliferative diseases; kidney diseases; sexual dysfunction; bone diseases; benign prostatic hyperplasia, transplant rejection, spasm, chronic obstructive bladder disease, and allergy.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

DETAILED DESCRIPTION OF THE INVENTION

Figure 1:
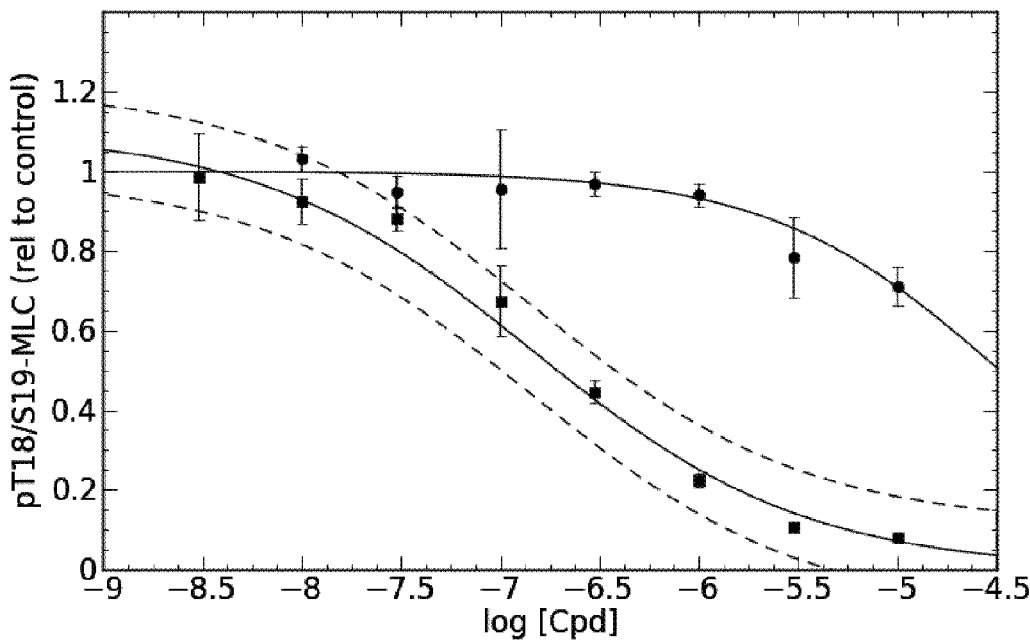
FIG. 1: Concentration-response curves for compound 14 (filled squares) and its metabolite Met1 (filled circles) in the MLC phosphorylation assay. 95% confidence interval is shown for compound 14.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Unless a context dictates otherwise, asterisks are used herein to indicate the point at which a mono- or bivalent radical depicted is connected to the structure to which it relates and of which the radical forms part.

Undefined (racemic) asymmetric centers that may be present in the compounds of the present invention are interchangeably indicated by drawing a wavy bonds or a straight bond in order to visualize the undefined steric character of the bond.

As already mentioned hereinbefore, in a first aspect the present invention provides compounds of Formula I

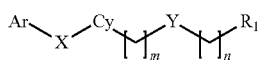
I

Wherein Ar, X, Cy, Y, m, n and $R^1$ are as defined hereinbefore, including the stereo-isomeric forms, solvates, and pharmaceutically acceptable addition salts thereof.

When describing the compounds of the invention, the terms used are to be construed in accordance with the following definitions, unless a context dictates otherwise:

The term "alkyl" by itself or as part of another substituent refers to a fully saturated hydrocarbon of Formula $C_xH_{2x+1}$ wherein x is a number greater than or equal to 1. Generally, alkyl groups of this invention comprise from 1 to 20 carbon atoms. Alkyl groups may be linear or branched and may be substituted as indicated herein. When a subscript is used herein following a carbon atom, the subscript refers to the number of carbon atoms that the named group may contain. Thus, for example, $C_{1-4}$alkyl means an alkyl of one to four carbon atoms. Examples of alkyl groups are methyl, ethyl, n-propyl, i-propyl, butyl, and its isomers (e.g. n-butyl, i-butyl and t-butyl); pentyl and its isomers, hexyl and its isomers, heptyl and its isomers, octyl and its isomers, nonyl and its isomers; decyl and its isomers. $C_1$-$C_6$ alkyl includes all linear, branched, or cyclic alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers, cyclopentyl, 2-, 3-, or 4-methylcyclopentyl, cyclopentylmethylene, and cyclohexyl.

The term "optionally substituted alkyl" refers to an alkyl group optionally substituted with one or more substituents (for example 1 to 4 substituents, for example 1, 2, 3, or 4 substituents or 1 to 2 substituents; in particular one substituent) at any available point of attachment. Non-limiting examples of such substituents include halo, hydroxyl, oxo, carbonyl, nitro, amino, amido, oxime, imino, azido, hydrazino, cyano, aryl, heteroaryl, cycloalkyl, heterocyclyl, acyl, alkylamino, alkoxy, haloalkoxy, haloalkyl, thiol, alkylthio, carboxylic acid, acylamino, alkyl esters, carbamate, thioamido, urea, sulllfonamido and the like. Preferably, such substituents are selected from halo, hydroxyl, nitro, amino, cyano, aryl (in particular phenyl), cycloalkyl, heterocyclyl (in particular pyrrolidine, oxolane, thiolane or $Het^1$ as described hereinbelow; more in particular pyrrolidine or oxolane), and alkoxy. More preferably, the substituents are selected from hydroxyl, aryl (in particular phenyl), cycloalkyl, heterocyclyl (in particular pyrrolidine, oxolane, thiolane or $Het^1$ as described hereinbelow; more in particular pyrrolidine or oxolane), and alkoxy.

The term "alkenyl", as used herein, unless otherwise indicated, means straight-chain, cyclic, or branched-chain hydrocarbon radicals containing at least one carbon-carbon double bond. Examples of alkenyl radicals include ethenyl, E- and Z-propenyl, isopropenyl, E- and Z-butenyl, E- and Z-isobutenyl, E- and Z-pentenyl, E- and Z-hexenyl, E,E-, E,Z-, Z,E-, Z,Z-hexadienyl, and the like. An optionally substituted alkenyl refers to an alkenyl having optionally one or more substituents (for example 1, 2, 3 or 4), selected from those defined above for substituted alkyl.

The term "alkynyl", as used herein, unless otherwise indicated, means straight-chain or branched-chain hydrocarbon radicals containing at least one carbon-carbon triple bond. Examples of alkynyl radicals include ethynyl, propynyl, butynyl, pentynyl, hexynyl, and the like. An optionally substituted alkynyl refers to an alkynyl having optionally one or more substituents (for example 1, 2, 3 or 4), selected from those defined above for substituted alkyl.

The term "cycloalkyl" by itself or as part of another substituent is a cyclic alkyl group, that is to say, a monovalent, saturated, or unsaturated hydrocarbyl group having 1, 2, or 3 cyclic structure. Cycloalkyl includes all saturated or partially saturated (containing 1 or 2 double bonds) hydrocarbon groups containing 1 to 3 rings, including monocyclic, bicyclic, or polycyclic alkyl groups. Cycloalkyl groups may comprise 3 or more carbon atoms in the ring and generally, according to this invention comprise from 3 to 15 atoms. The further rings of multi-ring cycloalkyls may be either fused, bridged and/or joined through one or more spiro atoms. Cycloalkyl groups may also be considered to be a subset of homocyclic rings discussed hereinafter. Examples of cycloalkyl groups include but are not limited to cyclopropyl, cyclobutyl, cyclopentyl, cyclohexyl, cycloheptyl, cyclooctyl, cyclononyl, adamantanyl, bicyclo(2.2.1)heptanyl and cyclodecyl with cyclopropyl, cyclopentyl, cyclohexyl, adamantanyl, and bicyclo(2.2.1)heptanyl being particularly preferred. An "optionally substituted cycloalkyl" refers to a cycloalkyl having optionally one or more substituents (for example 1 to 3 substituents, for example 1, 2, 3 or 4 substituents), selected from those defined above for substituted alkyl. When the suffix "ene" is used in conjunction with a cyclic group, hereinafter also referred to as "Cycloalkylene", this is intended to mean the cyclic group as defined herein having two single bonds as points of attachment to other groups. Cycloalkylene groups of this invention preferably comprise the same number of carbon atoms as their cycloalkyl radical counterparts.

Where alkyl groups as defined are divalent, i.e., with two single bonds for attachment to two other groups, they are termed "alkylene" groups. Non-limiting examples of alkylene groups includes methylene, ethylene, methylmethylene, trimethylene, propylene, tetramethylene, ethylethylene, 1,2-dimethylethylene, pentamethylene and hexamethylene. Similarly, where alkenyl groups as defined above and alkynyl groups as defined above, respectively, are divalent radicals having single bonds for attachment to two other groups, they are termed "alkenylene" and "alkynylene" respectively.

Generally, alkylene groups of this invention preferably comprise the same number of carbon atoms as their alkyl counterparts. Where an alkylene or cycloalkylene biradical is present, connectivity to the molecular structure of which it forms part may be through a common carbon atom or different carbon atom, preferably a common carbon atom. To illustrate this applying the asterisk nomenclature of this invention, a $C_3$ alkylene group may be for example *—$CH_2$ $CH_2CH_2$—*, *—CH(—$CH_2CH_3$)—*, or *—$CH_2$ CH(—$CH_3$)—*. Likewise a $C_3$ cycloalkylene group may be:

Where a cycloalkylene group is present, this is preferably a $C_3$-$C_6$ cycloalkylene group, more preferably a $C_3$ cycloalkylene (i.e. cyclopropylene group) wherein its connectivity to the structure of which it forms part is through a common carbon atom. Cycloalkylene and alkylene biradicals in compounds of the invention may be, but preferably are not, substituted.

The terms "heterocyclyl" or "heterocyclo" as used herein by itself or as part of another group refer to non-aromatic, fully saturated or partially unsaturated cyclic groups (for example, 3 to 13 member monocyclic, 7 to 17 member bicyclic, or 10 to 20 member tricyclic ring systems, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms. An optionally substituted heterocyclyl refers to a heterocyclyl having optionally one or more substituents (for example 1 to 4 substituents, or for example 1, 2, 3 or 4), selected from those defined for substituted aryl.

Exemplary heterocyclic groups include piperidinyl, azetidinyl, imidazolinyl, imidazolidinyl, isoxazolinyl, oxazolidinyl, isoxazolidinyl, thiazolidinyl, isothiazolidinyl, piperidyl, succinimidyl, 3H-indolyl, isoindolinyl, chromenyl, isochromanyl, xanthenyl, 2H-pyrrolyl, 1-pyrrolinyl, 2-pyrrolinyl, 3-pyrrolinyl, pyrrolidinyl, 4H-quinolizinyl, 4aH-carbazolyl, 2-oxopiperazinyl, piperazinyl, homopiperazinyl, 2-pyrazolinyl, 3-pyrazolinyl, pyranyl, dihydro-2H-pyranyl, 4H-pyranyl, 3,4-dihydro-2H-pyranyl, phthalazinyl, oxetanyl, thietanyl, 3-dioxolanyl, 1,3-dioxanyl, 2,5-dioximidazolidinyl, 2,2,4-piperidonyl, 2-oxopiperidinyl, 2-oxopyrrolodinyl, 2-oxoazepinyl, indolinyl, tetrahydropyranyl, tetrahydrofuranyl, tetrehydrothienyl, tetrahydroquinolinyl, tetrahydroisoquinolinyl, thiomorpholinyl, thiomorpholinyl sulfoxide, thiomorpholinyl sulfone, 1,3-dioxolanyl, 1,4-oxathianyl, 1,4-dithianyl, 1,3,5-trioxanyl, 6H-1,2,5-thiadiazinyl, 2H-1,5,2-dithiazinyl, 2H-oxocinyl, 1H-pyrrolizinyl, tetrahydro-1,1-dioxothienyl, N-formylpiperazinyl, and morpholinyl.

The term "aryl" as used herein refers to a polyunsaturated, aromatic hydrocarbyl group having a single ring (i.e. phenyl) or multiple aromatic rings fused together (e.g. naphthalene or anthracene) or linked covalently, typically containing 6 to 10 atoms; wherein at least one ring is aromatic. The aromatic ring may optionally include one to three additional rings (either cycloalkyl, heterocyclyl, or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, 1-, 2-, 3-, 4-, 5-, 6-, 7-, or 8-azulenyl, 1- or 2-naphthyl, 1-, 2-, or 3-indenyl, 1-, 2-, or 9-anthryl, 1-2-, 3-, 4-, or 5-acenaphtylenyl, 3-, 4-, or 5-acenaphtenyl, 1-, 2-, 3-, 4-, or 10-phenanthryl, 1- or 2-pentalenyl, 1,2-, 3-, or 4-fluorenyl, 4- or 5-indanyl, 5-, 6-, 7-, or 8-tetrahydronaphthyl, 1,2,3,4-tetrahydronaphthyl, 1,4-dihydronaphthyl, dibenzo[a,d]cylcoheptenyl, and 1-, 2-, 3-, 4-, or 5-pyrenyl.

The aryl ring can optionally be substituted by one or more substituents. An "optionally substituted aryl" refers to an aryl having optionally one or more substituents (for example 1 to 5 substituents, for example 1, 2, 3 or 4) at any available point of attachment. Non-limiting examples of such substituents are selected from halogen, hydroxyl, oxo, nitro, amino, hydrazine, aminocarbonyl, azido, cyano, alkyl, cycloalkyl, alkenyl, alkynyl, cycloalkylalkyl, alkylamino, alkoxy, —SO$_2$—NH$_2$, aryl, heteroaryl, aralkyl, haloalkyl, haloalkoxy, alkoxycarbonyl, alkylaminocarbonyl, heteroarylalkyl, alkylsulfonamide, heterocyclyl, alkylcarbonylaminoalkyl, aryloxy, alkylcarbonyl, acyl, arylcarbonyl, aminocarbonyl, alkylsulfoxide, —SO$_2$R$^a$, alkylthio, carboxyl, and the like, wherein R$^a$ is alkyl or cycloalkyl. Preferably, such substituents are selected from halogen, hydroxyl, nitro, amino, cyano, alkyl (in particular C$_{1-6}$alkyl; more in particular methyl), alkylamino, alkoxy, and haloalkyl. Where a carbon atom in an aryl group is replaced with a heteroatom, the resultant ring is referred to herein as a heteroaryl ring.

The term "heteroaryl" as used herein by itself or as part of another group refers but is not limited to 5 to 12 carbon-atom aromatic rings or ring systems containing 1 to 3 rings which are fused together or linked covalently, typically containing 5 to 8 atoms; at least one of which is aromatic in which one or more carbon atoms in one or more of these rings can be replaced by oxygen, nitrogen or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, benzopyranyl, 1(4H)-benzopyranyl, 1(2H)-benzopyranyl, 3,4-dihydro-1(2H)-benzopyranyl, 3,4-dihydro-1(2H)-benzopyranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl, 7-azaindolyl, 6-azaindolyl, 5-azaindolyl, 4-azaindolyl.

The term "pyrrolyl" (also called azolyl) as used herein includes pyrrol-1-yl, pyrrol-2-yl and pyrrol-3-yl. The term "furanyl" (also called "fury)") as used herein includes furan-2-yl and furan-3-yl (also called furan-2-yl and furan-3-yl). The term "thiophenyl" (also called "thienyl") as used herein includes thiophen-2-yl and thiophen-3-yl (also called thien-2-yl and thien-3-yl). The term "pyrazolyl" (also called 1H-pyrazolyl and 1,2-diazolyl) as used herein includes pyrazol-1-yl, pyrazol-3-yl, pyrazol-4-yl and pyrazol-5-yl. The term "imidazolyl" as used herein includes imidazol-1-yl, imidazol-2-yl, imidazol-4-yl and imidazol-5-yl. The term "oxazolyl" (also called 1,3-oxazolyl) as used herein includes oxazol-2-yl; oxazol-4-yl and oxazol-5-yl. The term "isoxazolyl" (also called 1,2-oxazolyl), as used herein includes isoxazol-3-yl, isoxazol-4-yl, and isoxazol-5-yl. The term "thiazolyl" (also called 1,3-thiazolyl), as used herein includes thiazol-2-yl, thiazol-4-yl and thiazol-5-yl (also called 2-thiazolyl, 4-thiazolyl and 5-thiazolyl). The term "isothiazolyl" (also called 1,2-thiazolyl) as used herein includes isothiazol-3-yl, isothiazol-4-yl, and isothiazol-5-yl. The term "triazolyl" as used herein includes 1H-triazolyl and 4H-1,2,4-triazolyl, "1H-triazolyl" includes 1H-1,2,3-triazol-1-yl, 1H-1,2,3-triazol-4-yl, 1H-1,2,3-triazol-5-yl, 1H-1,2,4-triazol-1-yl, 1H-1,2,4-triazol-3-yl and 1H-1,2,4-triazol-5-yl. "4H-1,2,4-triazolyl" includes 4H-1,2,4-triazol-4-yl, and 4H-1,2,4-triazol-3-yl. The term "oxadiazolyl" as used herein includes 1,2,3-oxadiazol-4-yl, 1,2,3-oxadiazol-5-yl, 1,2,4-oxadiazol-3-yl, 1,2,4-oxadiazol-5-yl, 1,2,5-oxadiazol-3-yl and 1,3,4-oxadiazol-2-yl. The term "thiadiazolyl" as used herein includes 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl (also called furazan-3-yl) and 1,3,4-thiadiazol-2-yl. The term "tetrazolyl" as used herein includes 1H-tetrazol-1-yl, 1H-tetrazol-5-yl, 2H-tetrazol-2-yl, and 2H-tetrazol-5-yl. The term "oxatriazolyl" as used herein includes 1,2,3,4-oxatriazol-5-yl and 1,2,3,5-oxatriazol-4-yl. The term "thiatriazolyl" as used herein includes 1,2,3,4-thiatriazol-5-yl and 1,2,3,5-thiatriazol-4-yl. The term "pyridinyl" (also called "pyridyl") as used herein includes pyridin-2-yl, pyridin-3-yl and pyridin-4-yl (also called 2-pyridyl, 3-pyridyl and 4-pyridyl). The term "pyrimidyl" as used herein includes pyrimid-2-yl, pyrimid-4-yl, pyrimid-5-yl and pyrimid-6-yl. The term "pyrazinyl" as used herein includes pyrazin-2-yl and pyrazin-3-yl. The term "pyridazinyl as used herein includes pyridazin-3-yl and pyridazin-4-yl. The term "oxazinyl" (also called "1,4-oxazinyl") as used herein includes 1,4-oxazin-4-yl and 1,4-oxazin-5-yl. The term "dioxinyl" (also called "1,4-dioxinyl") as used herein includes 1,4-dioxin-2-yl and 1,4-dioxin-3-yl. The term "thiazinyl" (also called "1,4-thiazinyl") as used herein includes 1,4-thiazin-2-yl, 1,4-thiazin-3-yl, 1,4-thiazin-4-yl, 1,4-thiazin-5-yl and 1,4-thiazin-6-yl. The term "triazinyl" as used herein includes 1,3,5-triazin-2-yl, 1,2,4-triazin-3-yl, 1,2,4-triazin-5-yl, 1,2,4-triazin-6-yl, 1,2,3-triazin-4-yl and 1,2,3-triazin-5-yl. The term "imidazo[2,1-b][1,3]thiazolyl" as used herein includes imidazo[2,1-b][1,3]thiazoi-2-yl, imidazo[2,1-b][1,3]thiazol-3-yl, imidazo[2,1-b][1,3]thiazol-5-yl and imidazo[2,1-b][1,3]thiazol-6-yl. The term "thieno[3,2-b]furanyl" as used herein includes thieno[3,2-b]furan-2-yl, thieno[3,2-b]furan-3-yl, thieno[3,2-b]furan-4-yl, and thieno[3,2-b]furan-5-yl. The term "thieno[3,2-b]thiophenyl" as used herein includes thieno[3,2-b]thien-2-yl, thieno[3,2-b]thien-3-yl, thieno[3,2-b]thien-5-yl and thieno[3,2-b]thien-6-yl. The term "thieno[2,3-d][1,3]thiazolyl" as used herein includes thieno[2,3-d][1,3]thiazol-2-yl, thieno[2,3-d][1,3]thiazol-5-yl and thieno[2,3-d][1,3]thiazol-6-yl. The term "thieno[2,3-d]imidazolyl" as used herein includes thieno[2,3-d]imidazol-2-yl, thieno[2,3-d]imidazol-4-yl and thieno[2,3-d]imidazol-5-yl. The term "tetrazolo[1,5-a]pyridinyl" as used herein includes tetrazolo[1,5-a]pyridine-5-yl, tetrazolo[1,5-a]pyridine-6-yl, tetrazolo[1,5-a]pyridine-7-yl, and tetrazolo[1,5-a]pyridine-8-yl. The term "indolyl" as used herein includes indol-1-yl, indol-2-yl, indol-3-yl, -indol-4-yl, indol-5-yl, indol-6-yl and indol-7-yl. The term "indolizinyl" as used herein includes indolizin-1-yl, indolizin-2-yl, indolizin-3-yl, indolizin-5-yl, indolizin-6-yl, indolizin-7-yl, and indolizin-8-yl. The term "isoindolyl" as used herein includes isoindol-1-yl, isoindol-2-yl, isoindol-3-yl, isoindol-4-yl, isoindol-5-yl, isoindol-6-yl and isoindol-7-yl. The term "benzofuranyl" (also called benzo[b]furanyl) as used herein includes benzofuran-2-yl, benzofuran-3-yl, benzofuran-4-yl, benzofuran-5-yl, benzofuran-6-yl and benzofuran-7-yl. The term "isobenzofuranyl" (also called benzo[c]furanyl) as used herein includes isobenzofuran-1-yl, isobenzofuran-3-yl, isobenzofuran-4-yl, isobenzofuran-5-yl, isobenzofuran-6-yl and isobenzofuran-7-yl. The term "benzothiophenyl" (also called benzo[b]thienyl) as used herein includes 2-benzo[b]thiophenyl, 3-benzo[b]thiophenyl, 4-benzo[b]thiophenyl, 5-benzo[b]thiophenyl, 6-benzo[b]thiophenyl and -7-benzo[b]thiophenyl (also called benzothien-2-yl, benzothien-3-yl, benzothien-4-yl, benzothien-5-yl, benzothien-6-yl and benzothien-7-yl). The term "isobenzothiophenyl" (also called benzo[c]thienyl) as used herein includes isobenzothien-1-yl, isobenzothien-3-yl, isobenzothien-4-yl, isobenzothien-5-yl, isobenzothien-6-yl and isobenzothien-7-yl. The term "indazolyl" (also called 1H-indazolyl or 2-azaindolyl) as used herein includes 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 2H-indazol-3-yl, 2H-indazol-4-yl, 2H-indazol-5-yl, 2H-indazol-6-yl, and 2H-indazol-7-yl. The term "benzimidazolyl" as used herein includes benzimidazol-1-yl, benzimidazol-2-yl, benzimidazol-4-yl, benzimidazol-5-yl, benzimidazol-6-yl and benzimidazol-7-yl. The term "1,3-benzoxazolyl" as used herein includes 1,3-benzoxazol-2-yl, 1,3-benzoxazol-4-yl, 1,3-benzoxazol-5-yl, 1,3-benzoxazol-6-yl and 1,3-benzoxazol-7-yl. The term "1,2-benzisoxazolyl" as used herein includes 1,2-benzisoxazol-3-yl, 1,2-benzisoxazol-4-yl, 1,2-benzisoxazol-5-yl, 1,2-benzisoxazol-6-yl and 1,2-benzisoxazol-7-yl. The term "2,1-benzisoxazolyl" as used herein includes 2,1-benzisoxazol-3-yl, 2,1-benzisoxazol-4-yl, 2,1-benzisoxazol-5-yl, 2,1-benzisoxazol-6-yl and 2,1-benzisoxazol-7-yl. The term "1,3-benzothiazolyl" as used herein includes 1,3-benzothiazol-2-yl, 1,3-benzothiazol-4-yl, 1,3-benzothiazol-5-yl, 1,3-benzothiazol-6-yl and 1,3-benzothiazol-7-yl. The term "1,2-benzoisothiazolyl" as used herein includes 1,2-benzisothiazol-3-yl, 1,2-benzisothiazol-4-yl, 1,2-benzisothiazol-5-yl, 1,2-benzisothiazol-6-yl and 1,2-benzisothiazol-7-yl. The term "2,1-benzoisothiazolyl" as used herein includes 2,1-benzisothiazol-3-yl, 2,1-benzisothiazol-4-yl, 2,1-benzisothiazol-5-yl, 2,1-benzisothiazol-6-yl and 2,1-benzisothiazol-7-yl. The term "benzotriazolyl" as used herein includes benzotriazol-1-yl, benzotriazol-4-yl, benzotriazol-5-yl, benzotriazol-6-yl and benzotriazol-7-yl. The term "1,2,3-benzoxadiazolyl" as used herein includes 1,2,3-benzoxadiazol-4-yl, 1,2,3-benzoxadiazol-5-yl, 1,2,3-benzoxadiazol-6-yl and 1,2,3-benzoxadiazol-7-yl. The term "2,1,3-benzoxadiazolyl" as used herein includes 2,1,3-benzoxadiazol-4-yl, 2,1,3-benzoxadiazol-5-yl, 2,1,3-benzoxadiazol-6-yl and 2,1,3-benzoxadiazol-7-yl. The term "1,2,3-benzothiadiazolyl" as used herein includes 1,2,3-benzothiadiazol-4-yl, 1,2,3-benzothiadiazol-5-yl, 1,2,3-benzothiadiazol-6-yl and 1,2,3-benzothiadiazol-7-yl. The term "2,1,3-benzothiadiazolyl" as used herein includes 2,1,3-benzothiadiazol-4-yl, 2,1,3-benzothiadiazol-5-yl, 2,1,3-benzothiadiazol-6-yl and 2,1,3-benzothiadiazol-7-yl. The term "thienopyridinyl" as used herein includes thieno[2,3-b]pyridinyl, thieno[2,3-c]pyridinyl, thieno[3,2-c]pyridinyl and thieno[3,2-b]pyridinyl. The term "purinyl" as used herein includes purin-2-yl, purin-6-yl, purin-7-yl and purin-8-yl. The term "imidazo[1,2-a]pyridinyl", as used herein includes imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl and imidazo[1,2-a]pyridin-7-yl. The term "1,3-benzodioxolyl", as used herein includes 1,3-benzodioxol-4-yl, 1,3-benzodioxol-5-yl, 1,3-benzodioxol-6-yl, and 1,3-benzodioxol-7-yl. The term "quinolinyl" as used herein includes quinolin-2-yl, quinolin-3-yl, quinolin-4-yl, quinolin-5-yl, quinolin-6-yl, quinolin-7-yl and quinolin-8-yl. The term "isoquinolinyl" as used herein includes isoquinolin-1-yl, isoquinolin-3-yl, isoquinolin-4-yl, isoquinolin-5-yl, isoquinolin-6-yl, isoquinolin-7-yl and isoquinolin-8-yl. The term "cinnolinyl" as used herein includes cinnolin-3-yl, cinnolin-4-yl, cinnolin-5-yl, cinnolin-6-yl, cinnolin-7-yl and cinnolin-8-yl. The term "quinazolinyl" as used herein includes quinazolin-2-yl, quiriazolin-4-yl, quinazolin-5-yl, quinazolin-6-yl, quinazolin-7-yl and quinazolin-8-yl. The term "quinoxalinyl". as used herein includes quinoxalin-2-yl, quinoxalin-5-yl, and quinoxalin-6-yl. The term "7-azaindolyl" as used herein refers to 1H-Pyrrolo[2,3-b]pyridinyl and includes 7-azaindol-1-yl, 7-azaindol-2-yl, 7-azaindol-3-yl, 7-azaindol-4-yl, 7-azaindol-5-yl, 7-azaindol-6-yl. The term "6-azaindolyl" as used herein refers to 1H-Pyrrolo[2,3-c]pyridinyl and includes 6-azaindol-1-yl, 6-azaindol-2-yl, 6-azaindol-3-yl, 6-azaindol-4-yl, 6-azaindol-5-yl, 6-azaindol-7-yl. The term "5-azaindolyl" as used herein refers to 1H-Pyrrolo[3,2-c]pyridinyl and includes 5-azaindol-1-yl, 5-azaindol-2-yl, 5-azaindol-3-yl, 5-azaindol-4-yl, 5-azaindol-6-yl, 5-azaindol-7-yl. The term "4-azaindolyl" as used herein refers to 1H-Pyrrolo[3,2-b]pyridinyl and includes 4-azaindol-1-yl, 4-azaindol-2-yl, 4-azaindol-3-yl, 4-azaindol-5-yl, 4-azaindol-6-yl, 4-azaindol-7-yl.

For example, non-limiting examples of heteroaryl can be 2- or 3-furyl, 2- or 3-thienyl, 1-, 2- or 3-pyrrolyl, 1-, 2-, 4- or 5-imidazolyl, 1-, 3-, 4- or 5-pyrazolyl, 3-, 4- or 5-isoxazolyl, 2-, 4- or 5-oxazolyl, 3-, 4- or 5-isothiazolyl, 2-, 4- or 5-thiazolyl, 1,2,3-triazol-1-, -4- or -5-yl, 1,2,4-triazol-1-, -3-, -4- or -5-yl, 1H-tetrazol-1-, or -5-yl, 2H-tetrazol-2-, or -5-yl, 1,2,3-oxadiazol-4- or -5-yl, 1,2,4-oxadiazol-3- or -5-yl, 1,2,5-oxadiazolyl, 1,3,4-oxadiazolyl, 1,2,3-thiadiazol-4- or -5-yl, 1,2,4-thiadiazol-3- or -5-yl, 1,2,5-thiadiazol-3- or -4-yl, 1,3,4-thiadiazolyl, 1- or 5-tetrazolyl, 2-, 3- or 4-pyridyl, 3- or 4-pyridazinyl, 2-, 4-, 5- or 6-pyrimidyl, 2-, 3-, 4-, 5-6-2H-thiopyranyl, 2-, 3- or 4-4H-thiopyranyl, 4-azaindol-1-, 2-, 3-, 5-, or 7-yl, 5-azaindol-1-, or 2-, 3-, 4-, 6-, or 7-yl, 6-azaindol-1,2-, 3-, 4-, 5-, or 7-yl, 7-azaindol-1-, 2-, 3-, 4,5-, or 6-yl, 2-, 3-, 4-, 5-, 6- or 7-benzofuryl, 1-, 3-, 4- or 5-isobenzofuryl, 2-, 3-, 4-, 5-, 6- or 7-benzothienyl, 1-, 3-, 4- or 5-isobenzothienyl, 1-, 2-, 3-, 4-, 5-, 6- or 7-indolyl, 2- or 3-pyrazinyl, 1,4-oxazin-2- or -3-yl, 1,4-dioxin-2- or -3-yl, 1,4-thiazin-2- or -3-yl, 1,2,3-triazinyl, 1,2,4-triazinyl, 1,3,5-triazin-2-, -4- or -6-yl, thieno[2,3-b]furan-2-, -3-, -4-, or -5-yl, benzimidazol-1-yl, -2-yl, -4-yl, -5-yl, -6-yl, or -7-yl, 1-, 3-, 4-, 5-, 6- or 7-benzopyrazolyl, 3-, 4-, 5-, 6- or 7-benzisoxazolyl, 2-, 4-, 5-, 6- or 7-benzoxazolyl, 3-, 4-, 5-, 6- or 7-benzisothiazolyl, 1,3-benzothiazol-2-yl, -4-yl, -5-yl, -6-yl or -7-yl, 1,3-benzodioxol-4-yl, -5-yl, -6-yl, or -7-yl, benzotriazol-1-yl, -4-yl, -5-yl, -6-yl or -7-yl1-, 2-thianthrenyl, 3-, 4- or 5-isobenzofuranyl, 1-, 2-, 3-, 4- or 9-xanthenyl, 1-, 2-, 3- or 4-phenoxathiinyl, 2-, 3-pyrazinyl, 1-, 2-, 3-, 4-, 5-, 6-, 7- or 8-indolizinyl, 2-, 3-, 4- or 5-isoindolyl, 1H-indazol-1-yl, 3-yl, -4-yl, -5-yl, -6-yl, or -7-yl, 2H-indazol-2-yl, 3-yl, -4-yl, -5-yl, -6-yl, or -7-yl, imidazo[2,1-b][1,3]thiazol-2-yl, imidazo[2,1-b][1,3]thiazol-3-yl, imidazo[2,1-b][1,3]thiazol-5-yl or imidazo[2,1-b][1,3]thiazol-6-yl, imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl or imidazo[1,2-a]pyridin-7-yl, tetrazolo[1,5-a]pyridine-5-yl, tetrazolo[1,5-a]pyridine-6-yl, tetrazolo[1,5-a]pyridine-7-yl, or tetrazolo[1,5-a]pyridine-8-yl, 2-, 6-, 7- or 8-purinyl, 4-, 5- or 6-phthalazinyl, 2-, 3- or 4-naphthyridinyl, 2-, 5- or 6-quinoxalinyl, 2-, 4-, 5-, 6-, 7- or 8-quinazolinyl, 1-, 2-, 3- or 4-quinolizinyl, 2-, 3-, 4-, 5-, 6-, 7-, or 8-quinolinyl(quinolyl), 2-, 4-, 5-, 6-, 7- or 8-quinazolyl, 1-, 3-, 4-, 5-, 6-, 7- or 8-isoquinolinyl(isoquinolyl), 3-, 4-, 5-, 6-, 7- or 8-cinnolinyl, 2-, 4-, 6- or 7-pteridinyl, 1-, 2-, 3-, 4- or 9-carbazolyl, 1-, 2-, 3-, 4-, 5-, 6-, 7-, 8- or 9-carbolinyl, 1-, 2-, 3-, 4-, 5-, 6-, 7-, 8-, 9- or 10-phenanthridinyl, 1-, 2-, 3- or 4-acridinyl, 1-, 2-, 3-, 4-, 5-, 6-, 7-, 8- or 9-perimidinyl, 2-, 3-, 4-, 5-, 6-, 7-, 8-, 9- or 10-(1,7)phenanthrolinyl, 1- or 2-phenazinyl, 1-, 2-, 3-, 4-, or 10-phenothiazinyl, 3- or 4-furazanyl, 1-, 2-, 3-, 4-, or 10-phenoxazinyl, or additionally substituted derivatives thereof.

An "optionally substituted heteroaryl" refers to a heteroaryl having optionally one or more substituents (for example 1 to 4 substituents, for example 1, 2, 3 or 4), selected from those defined above for substituted aryl.

The term "oxo" as used herein refers to the group =O.

The term "alkoxy" or "alkyloxy" as used herein refers to a radical having the Formula —OR$^b$ wherein R$^b$ is alkyl. Preferably, alkoxy is $C_1$-$C_{10}$ alkoxy, $C_1$-$C_6$ alkoxy, or $C_1$-$C_4$ alkoxy. Non-limiting examples of suitable alkoxy include methoxy, ethoxy, propoxy, isopropoxy, butoxy, isobutoxy, sec-butoxy, tert-butoxy, pentyloxy and hexyloxy. Where the oxygen atom in an alkoxy group is substituted with sulfur, the resultant radical is referred to as thioalkoxy. "Haloalkoxy" is an alkoxy group wherein one or more hydrogen atoms in the alkyl group are substituted with halogen. Non-limiting examples of suitable haloalkoxy include fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy, 2,2,2-trichloroethoxy; trichloromethoxy, 2-bromoethoxy, pentafluoroethyl, 3,3,3-trichloropropoxy, 4,4,4-trichlorobutoxy.

The term "aryloxy" as used herein denotes a group —O-aryl, wherein aryl is as defined above.

The term "arylcarbonyl" or "aroyl" as used herein denotes a group —C(O)-aryl, wherein aryl is as defined above.

The term "cycloalkylalkyl" by itself or as part of another substituent refers to a group having one of the aforementioned cycloalkyl groups attached to one of the aforementioned alkyl chains. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, 3-cyclopentylbutyl, cyclohexylbutyl and the like.

The term "heterocyclyl-alkyl" by itself or as part of another substituents refers to a group having one of the aforementioned heterocyclyl group attached to one of the aforementioned alkyl group, i.e., to a group —R$^d$-R$^c$ wherein R$^d$ is alkylene or alkylene substituted by alkyl group and R$^c$ is a heterocyclyl group.

The term "carboxy" or "carboxyl" or "hydroxycarbonyl" by itself or as part of another substituent refers to the group —CO$_2$H. Thus, a carboxyalkyl is an alkyl group as defined above having at least one substituent that is —CO$_2$H.

The term "alkoxycarbonyl" by itself or as part of another substituent refers to a carboxy group linked to an alkyl radical i.e. to form —C(=O)OR$^e$, wherein R$^e$ is as defined above for alkyl.

The term "alkylcarbonyloxy" by itself or as part of another substituent refers to a —O—C(=O)R$^e$ wherein R$^e$ is as defined above for alkyl.

The term "alkylcarbonylamino" by itself or as part of another substituent refers to an group of Formula —NH(C=O)R or —NR'(C=O)R, wherein R and R' are each independently alkyl or substituted alkyl.

The term "thiocarbonyl" by itself or as part of another substituent refers to the group —C(=S)—.

The term "alkoxy" by itself or as part of another substituent refers to a group consisting of an oxygen atom attached to one optionally substituted straight or branched alkyl group, cycloalkyl group, aralkyl, or cycloalkylalkyl group. Non-limiting examples of suitable alkoxy group include methoxy, ethoxy, n-propoxy, isopropoxy, n-butoxy, iso-butoxy, sec-butoxy, tert-butoxy, hexanoxy, and the like.

The term "halo" or "halogen" as a group or part of a group is generic for fluoro, chloro, bromo, or iodo.

The term "haloalkyl" alone or in combination, refers to an alkyl radical having the meaning as defined above wherein one or more hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl, and the like.

The term "haloaryl" alone or in combination, refers to an aryl radical having the meaning as defined above wherein one or more hydrogens are replaced with a halogen as defined above. The term "haloalkoxy" alone or in combination refers to a group of Formula —O-alkyl wherein the alkyl group is substituted by 1, 2, or 3 halogen atoms. For example, "haloalkoxy" includes —OCF$_3$, —OCHF$_2$, —OCH$_2$F, —O—CF$_2$—CF$_3$, —O—CH$_2$—CF$_3$, —O—CH$_2$—CHF$_2$, and —O—CH$_2$—CH$_2$F.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

As used herein the terms such as "alkyl, aryl, or cycloalkyl, each being optionally substituted with" or "alkyl, aryl, or cycloalkyl, optionally substituted with" refers to optionally substituted alkyl, optionally substituted aryl and optionally substituted cycloalkyl.

As described herein, some of the compounds of the invention may contain one or more asymmetric carbon atoms that serve as a chiral center, which may lead to different optical forms (e.g. enantiomers or diastereoisomers). The invention comprises all such optical forms in all possible configurations, as well as mixtures thereof.

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers and mixtures thereof are included within the scope of the invention.

Whenever used in the present invention the term "compounds of the invention" or a similar term is meant to include the compounds of general Formula I and any subgroup thereof. This term also refers to the compounds as depicted in Tables 1 to 11, their derivatives, N-oxides, salts, solvates, hydrates, stereoisomeric forms, racemic mixtures, tautomeric forms, optical isomers, analogues, pro-drugs, esters, and metabolites, as well as their quaternized nitrogen analogues. The N-oxide forms of said compounds are meant to comprise compounds wherein one or several nitrogen atoms are oxidized to the so-called N-oxide.

As used in the specification and the appended claims, the singular forms "a", "an", and "the" include plural referents unless the context clearly dictates otherwise. By way of example, "a compound" means one compound or more than one compound.

The terms described above and others used in the specification are well understood to those in the art.

As used herein, the term "ROCK" refers to either of the ROCK-I or ROCK-II isoforms or both. The terms "ROCK-I", "ROCK1" or any of their synonyms accepted in the art encompasses the known naturally occurring or biologically engineered mutants and constructs of ROCK-I. The terms "ROCK-2", "ROCK2" or any of their synonyms accepted in the art encompasses the known naturally occurring or biologically engineered mutants and constructs of ROCK-II.

Whenever used in the present document, the terms "soft inhibitor(s)", "soft kinase inhibitors", "soft ROCK inhibitors" or similar terms refer to compounds possessing inhibitory properties against ROCK, which are stable in a target organ, but are rapidly converted into a predictable, functionally inactive species once entering the systemic circulation. This inactivation process can occur in liver, but is preferentially achieved in blood.

As used herein, the term "target organ" refers to an organ (eg: eye), organ part (eg cornea, retina) or cellular tissue where inhibition of ROCK is expected to result in beneficial effects.

As used herein, the terms "functionally active species" of "functionally active compound" refer to a compound displaying significant in vivo activity and/or significant activity in cellular assays that are acknowledged in the art as physiologically relevant readouts of cellular ROCK activity. An example of such cellular assays is a Myosin Light Chain phosphorylation assay described by Schröter et al in *Biochemical and Biophysical Research Communications* 374 (2008) 356-360, which has been used to evaluate the cellular activity of compounds of the present invention. (see Examples, section C.1.2). As used herein, the terms "functionally inactive species" or "functionally inactive compound" refer to a compound displaying markedly reduced, preferably negligible activity in the same in vivo or cellular readouts of ROCK activity.

As used herein, the terms "esterase" or "esterases" encompasses all enzymes displaying carboxylic ester hydrolase (EC 3.1.1) activity. This definition includes enzymes displaying additional hydrolytic activity on substrates that are not carboxylic esters. For example; Paraoxonase 1 (PON1) displays aryldialkylphosphatase activity (EC 3.1.8.1, also known as paraoxonase activity, hence its name) and diisopropyl-fluorophosphatase activity (EC 3.1.8.2), but also arylesterase activity (EC 3.1.1.2) and lactonase activity. PON1 is therefore considered as an esterase. As used herein, the term "pseudoesterase" refers to a protein displaying some degree of carboxylic ester hydrolase activity, but low catalytic efficiency against carboxylic esters. Some proteins known as pseudoesterases, such as serum albumin, actually lack a true catalytic site.

In a further embodiment, the present invention provides compounds of formula I

Wherein

X is oxygen, —NH—, or a direct bond; in particular oxygen or —NH—; more in particular —NH—;

Y is —NH— or a direct bond;

n is an integer from 0 to 4;

m is an integer from 0 to 4;

Cy is selected from the group consisting of:

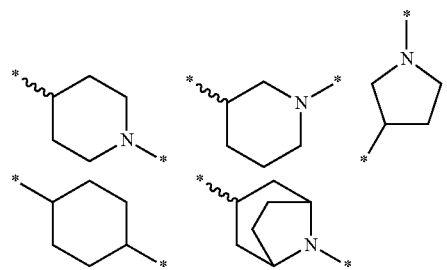

Ar is selected from the group comprising:

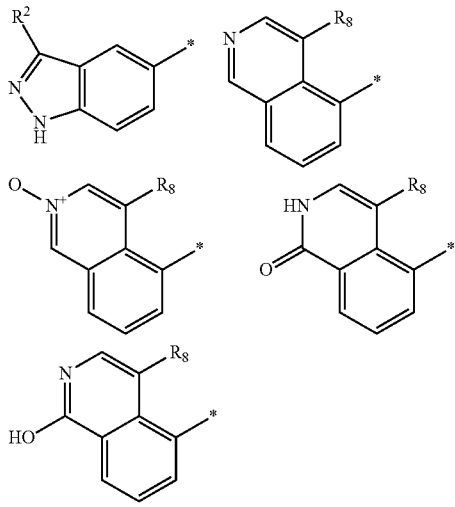

R² is hydrogen or methyl; in particular hydrogen;

R⁸ is hydrogen, methyl, halogen, or alkynyl; in particular hydrogen or methyl; more in particular hydrogen;

$R^1$ is an aryl or heteroaryl optionally substituted with halo or $C_{1-6}$alkyl; wherein said aryl or heteroaryl is substituted with a substituent selected from the group consisting of:

—$(CH_2)_p$—C(=O)—$OR^{21}$;

—$(CH_2)_p$—C(=O)—$NR^3R^4$;

—$(CH_2)_p$—C(=O)—$SR^{22}$;

$Het^1$, —O-$Het^1$, —NH-$Het^1$, or —S-$Het^1$; and

—O—$C_{1-6}$alkyl, —S—$C_{1-6}$alkyl, or —$C_{1-6}$alkyl; wherein said —O—$C_{1-6}$alkyl, —NH—$C_{1-6}$alkyl, —S—$C_{1-6}$alkyl, or —$C_{1-6}$alkyl are each independently substituted with a substituent selected from the group consisting of —C(=O)—$OR^{21}$, —C(=O)—$NR^3R^4$, $Het^1$, —O-$Het^1$, —NH-$Het^1$, and —S-$Het^1$;

Wherein p is an integer from 0 to 3

$Het^1$ is selected from the group consisting of:

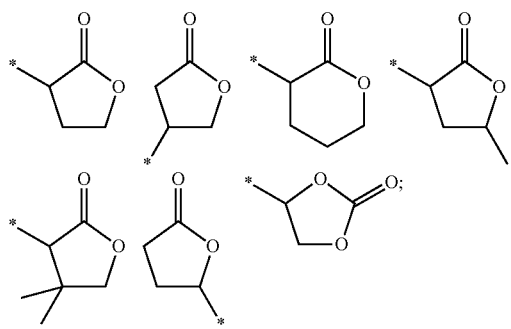

in particular $Het^1$ is selected from the group consisting of

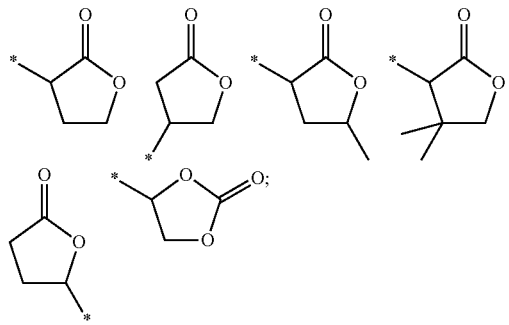

more in particular $Het^1$ is selected from the group consisting of

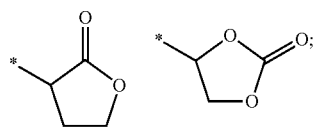 [SMILES: *C1CCOC1=O ; *C1COC(=O)O1]

$R^{21}$ is selected from the group consisting of optionally substituted $C_{1-20}$alkyl, optionally substituted $C_{1-20}$alkenyl, optionally substituted $C_{1-20}$alkynyl, optionally substituted $C_{3-15}$cycloalkyl, optionally substituted aryl, optionally substituted heterocyclyl, and optionally substituted heteroaryl; in particular $R^{21}$ is selected from optionally substituted $C_{1-20}$alkyl and optionally substituted aryl; more in particular from aryl and optionally substituted $C_{1-20}$alkyl;

$R^{22}$ is optionally substituted $C_{1-6}$alkyl; in particular $R^{22}$ is $C_{1-6}$alkyl;

$R^3$ is selected from the group consisting of $Het^1$, $C_{1-20}$alkyl, aryl or heteroaryl; wherein said $C_{1-20}$alkyl, aryl or heteroaryl is substituted with 1, 2 or 3 substituents each independently selected from the group consisting of aryl, heteroaryl, —$(CH_2)_p$—C(=O)—$OR^{21}$, -$Het^1$, —NH-$Het^1$, —O-$Het^1$, —S-$Het^1$, —S—$C_{2-6}$alkyl, —NH—$C_{2-6}$alkyl, and —O—$C_{2-6}$alkyl;

Wherein said aryl, heteroaryl, —O—$C_{2-6}$alkyl, —NH—$C_{2-6}$alkyl, or —S—$C_{2-6}$alkyl are each independently substituted with a substituent selected from the group consisting of C(=O)—$OR^{21}$, -$Het^1$, —O-$Het^1$, —NH-$Het^1$, and —S-$Het^1$;

in particular $R^3$ is selected from the group consisting of $Het^1$, $C_{1-20}$alkyl, aryl or heteroaryl; wherein said $C_{1-20}$alkyl, aryl or heteroaryl is substituted with 1, 2 or 3 substituents each independently selected from the group consisting of —$(CH_2)_p$—C(=O)—$OR^{21}$, -$Het^1$, —NH-$Het^1$, —O-$Het^1$, and —S-$Het^1$;

more in particular $R^3$ is selected from the group consisting of $Het^1$, $C_{1-20}$alkyl, or aryl; wherein said $C_{1-20}$alkyl or aryl is substituted with 1, 2 or 3; preferably 1; substituents each independently selected from the group consisting of —$(CH_2)$—C(=O)—$OR^{21}$, -$Het^1$, and —S-$Het^1$;

and $R^4$ is selected from the group consisting of hydrogen or $C_{1-6}$alkyl; in particular hydrogen; or R³ and R⁴ together with the nitrogen atom to which they are attached form a heterocycle substituted with one substituent selected from the group consisting of $C_{1-20}$alkyl, aryl or heteroaryl; wherein said $C_{1-20}$alkyl, aryl, or heteroaryl is substituted with 1, 2 or 3 substituents each independently selected from the group consisting of aryl, heteroaryl, —C(=O)—OR²¹, -Het¹, —O-Het¹, —S-Het¹, —S—$C_{2-6}$alkyl, —NH—$C_{2-6}$alkyl, and —O—$C_{2-6}$alkyl;

Wherein said —O—$C_{2-6}$alkyl, —NH—$C_{2-6}$alkyl, or —S—$C_{2-6}$alkyl are each independently substituted with a substituent selected from the group consisting of C(=O)—OR²¹, -Het¹, —O-Het¹, —NH-Het¹, and —S-Het¹;

with the proviso that

R¹ can not be selected from aryl or heteroaryl substituted with —O—$CH_2$—C(=O)—OR²¹;

if R¹ is phenyl, then said phenyl can not be substituted with —($CH_2$)—C(=O)—OR²¹ in the para position; and said compound of formula I is not

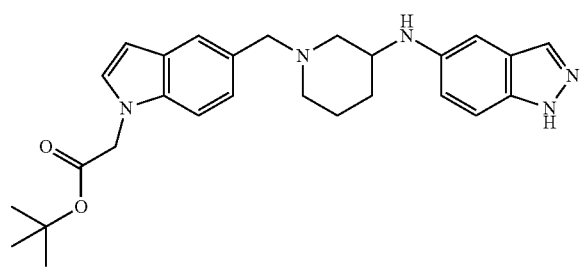 [SMILES: CC(C)(C)OC(=O)Cn1ccc2cc(CN3CCCC(Nc4ccc5[nH]ncc5c4)C3)ccc21]

In a preferred embodiment, the present invention provides compounds of formula I wherein X, Y, n, m, Cy and Ar are as defined hereinbefore and wherein R¹ is aryl or heteroaryl; in particular aryl or any heteroaryl except for indolyl; more in particular phenyl, pyrrolyl or thiophenyl; substituted with a substituent selected from the group consisting of:

—($CH_2$)$_p$C(=O)—OR²¹,
—($CH_2$)$_p$C(=O)—NR³R⁴;
—($CH_2$)—C(=O)—SR²²;
Het¹, —O-Het¹, —NH-Het¹, or —S-Het¹; and
—O—$C_{1-6}$alkyl, —NH—$C_{1-6}$alkyl, —S—$C_{1-6}$alkyl, —$C_{1-6}$alkyl; wherein said —O—$C_{1-6}$alkyl, —NH—$C_{1-6}$alkyl, —S—$C_{1-6}$alkyl, or —$C_{1-6}$alkyl are each independently substituted with a substituent selected from the group consisting of —C(=O)—OR²¹, —C(=O)—NR³R⁴, -Het¹, —O-Het¹, —NH-Het¹, and —S-Het¹;

Wherein p, Het¹, R²¹, R²², R³, and R⁴, are as defined hereinbefore, with the proviso that R¹ can not be selected from aryl or heteroaryl substituted with —O—$CH_2$—C(=O)—OR²¹;

if R¹ is phenyl, then said phenyl can not be substituted with —($CH_2$)$_p$—C(=O)—OR²¹ in the para position; and said compound of formula I is not

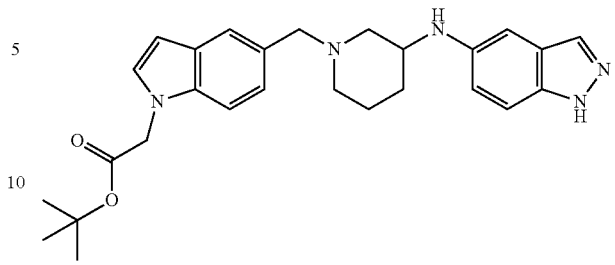

In an even further embodiment, the present invention provides compounds of formula I Wherein X, Y, n, m, Cy and Ar are as defined hereinbefore and wherein R¹ is an aryl or heteroaryl; more in particular phenyl, pyrrolyl or thiophenyl substituted with a substituent selected from the group consisting of;

—($CH_2$)$_p$—C(=O)—OR²¹
—($CH_2$)$_p$—C(=O)—NR³R⁴
—($CH_2$)$_p$—C(=O)—SR²²
—O—$C_{1-6}$alkyl; —NH—$C_{1-6}$alkyl; —S—$C_{1-6}$alkyl; —$C_{1-6}$alkyl; wherein said —O—$C_{1-6}$alkyl; —NH—$C_{1-6}$alkyl; —S—$C_{1-6}$alkyl; or —$C_{1-6}$alkyl are each independently substituted with a substituent selected from the group consisting of —C(=O)—OR²¹; —C(=O)—NR³R⁴; Het¹; —O-Het¹; —NH-Het¹ and —S-Het¹;

Wherein p, R²¹, R²², R³, R⁴ and Het¹ are as defined hereinbefore;

with the proviso that

R¹ can not be selected from aryl or heteroaryl substituted with —O—$CH_2$—C(=O)—OR²¹;

if R¹ is phenyl, then said phenyl can not be substituted with —($CH_2$)$_p$—C(=O)—OR²¹ in the para position; and said compound of formula I is not

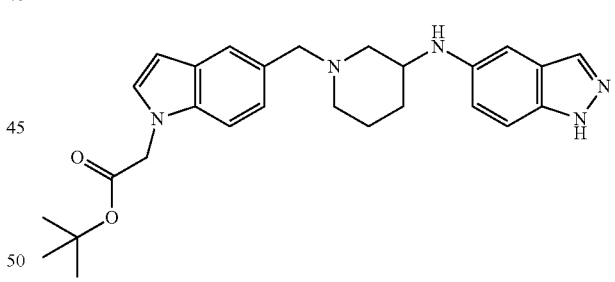

In another embodiment, the present invention provides compounds of formula I

Wherein X, Y, n, and m are as defined hereinbefore and wherein

Cy represents a bivalent radical selected from the group consisting of

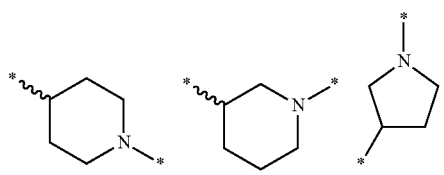

-continued

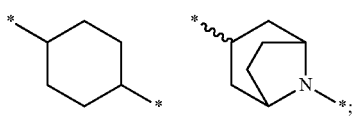

in particular from the group consisting of

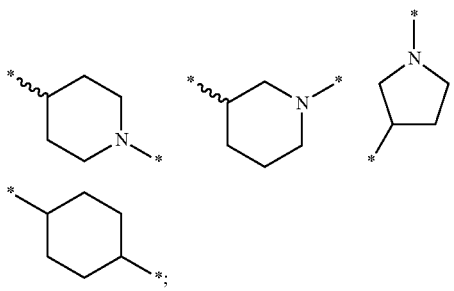

Ar is selected from the group consisting of;

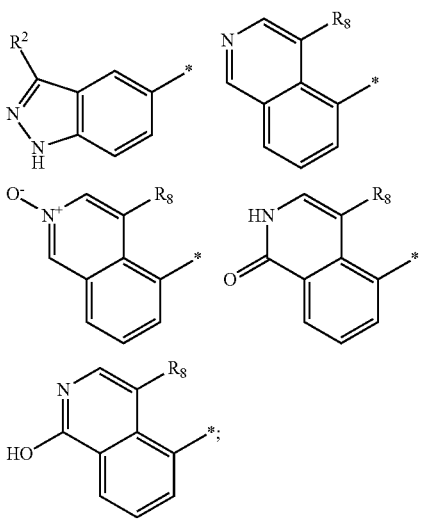

in particular from the group consisting of:

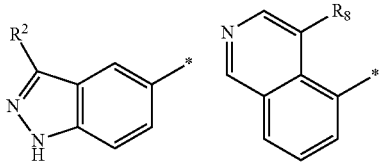

Wherein $R^1$, $R^{21}$, $R^{22}$, $R^3$, $R^4$, and $Het^1$ are as defined hereinbefore;

with the proviso that $R^1$ can not be selected from aryl or heteroaryl substituted with —O—CH$_2$—C(=O)—OR$^{21}$;

if $R^1$ is phenyl, then said phenyl can not be substituted with —(CH$_2$)$_p$—C(=O)—OR$^{21}$ in the para position; and said compound of formula I is not

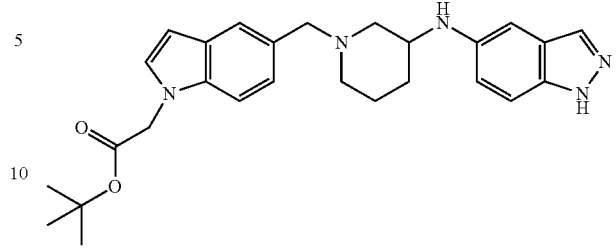

In yet another embodiment, the invention provides compounds of formula I wherein one or more of the following restrictions apply:

X is oxygen, —NH— or a direct bond; in particular oxygen or —NH—; more in particular —NH—;

Y is —NH— or a direct bond; in particular —NH—;

n is an integer from 0 to 4; in particular 0 or 1;

m is an integer from 0 to 4; in particular 0 or 1; more in particular 0;

Cy represents a bivalent radical consisting of a satured (poly)cycle, including fused, bi-, spiro or bridged carbocycles and heterocycles;

Cy is selected from the group consisting of:

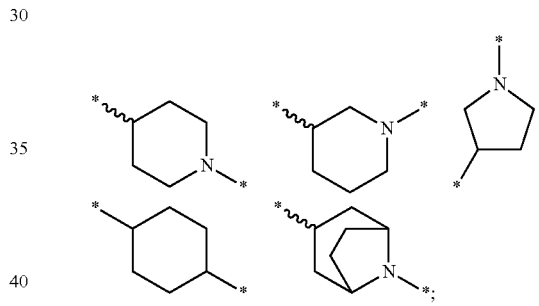

in particular from the group consisting of:

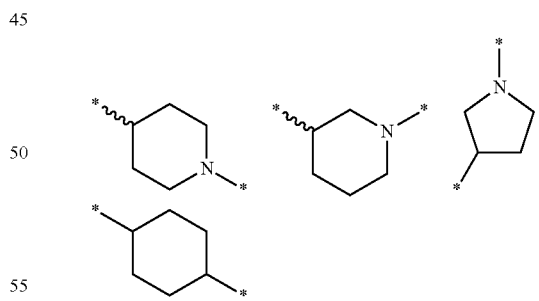

Ar is selected from the group comprising:

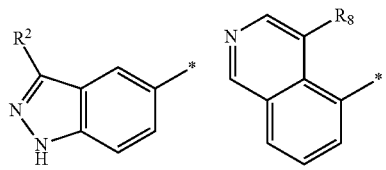

-continued

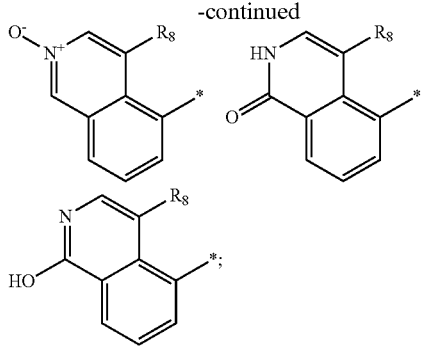

in particular from the group consisting of

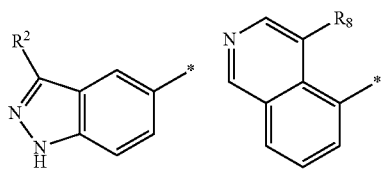

$R^2$ is hydrogen or methyl; in particular hydrogen;
$R^8$ is hydrogen, methyl, halogen, or alkynyl; in particular hydrogen or methyl; more in particular hydrogen;
$R^1$ is an aryl or heteroaryl optionally substituted with halo or $C_{1-6}$alkyl; wherein said aryl or heteroaryl is substituted with a substituent selected from the group consisting of:
—$(CH_2)_p$—C(=O)—OR$^{21}$;
—$(CH_2)_p$—C(=O)—NR$^3$R$^4$;
—$(CH_2)_p$—C(=O)—SR$^{22}$;
Het$^1$, —O-Het$^1$, —NH-Het$^1$, or —S-Het$^1$; and
—O—$C_{1-6}$alkyl, —S—$C_{1-6}$alkyl, or —$C_{1-6}$alkyl; wherein said —O—$C_{1-6}$alkyl, —NH—$C_{1-6}$alkyl, —S—$C_{1-6}$alkyl, or —$C_{1-6}$alkyl are each independently substituted with a substituent selected from the group consisting of —C(=O)—OR$^{21}$, —C(=O)—NR$^3$R$^4$, -, Het$^1$, —O-Het$^1$, —NH-Het$^1$, and —S-Het$^1$;
in particular a substituent selected from the group consisting of:
—$(CH_2)_p$—C(=O)—OR$^{21}$;
—$(CH_2)_p$—C(=O)—NR$^3$R$^4$;
—$(CH_2)_p$—C(=O)—SR$^{22}$; and
—O—$C_{1-6}$alkyl, —S—$C_{1-6}$alkyl, or —$C_{1-6}$alkyl; wherein said —O—$C_{1-6}$alkyl, —S—$C_{1-6}$alkyl, or —$C_{1-6}$alkyl are each independently substituted with a substituent selected from the group consisting of —C(=O)—OR$^{21}$, —C(=O)—NR$^3$R$^4$, -, Het$^1$, —O-Het$^1$, —NH-Het$^1$, and —S-Het$^1$; in particular —O—$C_{1-6}$alkyl substituted with —C(=O)—NR$^3$R$^4$;
$R^1$ is an aryl or heteroaryl; in particular aryl, pyrrolyl or thiophenyl; more in particular phenyl, pyrrolyl or thiophenyl; substituted with a a substituent selected from the group consisting of:
—$(CH_2)_p$—C(=O)—OR$^{21}$;
—$(CH_2)_p$—C(=O)—NR$^3$R$^4$;
—$(CH_2)_p$—C(=O)—SR$^{22}$;
Het$^1$, —O-Het$^1$, —NH-Het$^1$, or —S-Het$^1$; and
—O—$C_{1-6}$alkyl, —S—$C_{1-6}$alkyl, or —$C_{1-6}$alkyl; wherein said —O—$C_{1-6}$alkyl, —NH—$C_{1-6}$alkyl, —S—$C_{1-6}$alkyl, or —$C_{1-6}$alkyl are each independently substituted with a substituent selected from the group consisting of —C(=O)—OR$^{21}$, —C(=O)—NR$^3$R$^4$, Het$^1$, —O-Het$^1$, —NH-Het$^1$, and —S-Het$^1$;
in particular a substituent selected from the group consisting of:
—$(CH_2)_p$—C(=O)—OR$^{21}$;
—$(CH_2)_p$—C(=O)—NR$^3$R$^4$;
—$(CH_2)_p$—C(=O)—SR$^{22}$; and
—O—$C_{1-6}$alkyl, —S—$C_{1-6}$alkyl, or —$C_{1-6}$alkyl; wherein said —O—$C_{1-6}$alkyl, —S—$C_{1-6}$alkyl, or —$C_{1-6}$alkyl are each independently substituted with a substituent selected from the group consisting of —C(=O)—OR$^{21}$, —C(=O)—NR$^3$R$^4$, Het$^1$, —O-Het$^1$, —NH-Het$^1$, and —S-Het$^1$; in particular —O—$C_{1-6}$alkyl substituted with —C(=O)—NR$^3$R$^4$;
p is an integer from 0 to 3; in particular 0 or 1;
Het$^1$ is selected from the group consisting of:

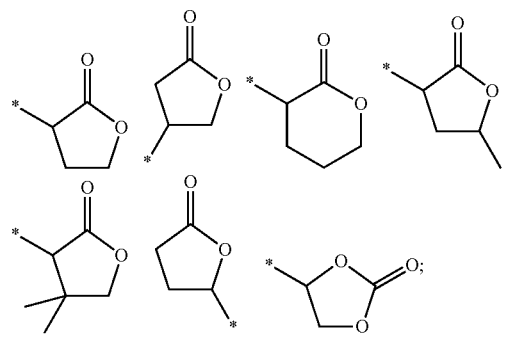

in particular Het$^1$ is selected from the group consisting of

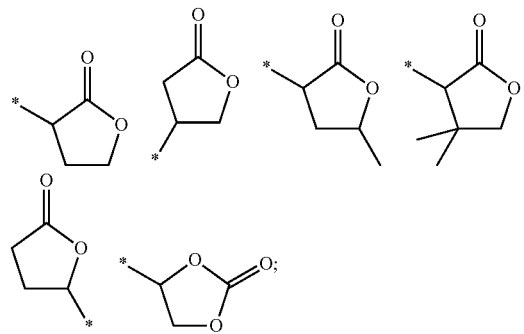

more in particular Het$^1$ is selected from the group consisting of

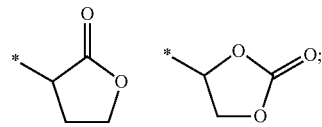

$R^{21}$ is selected from the group consisting of optionally substituted $C_{1-20}$alkyl, optionally substituted $C_{1-20}$alkenyl, optionally substituted $C_{1-20}$alkynyl, optionally substituted $C_{3-15}$cycloalkyl, optionally substituted aryl, optionally substituted heterocyclyl, and optionally substituted heteroaryl; in particular from optionally substituted $C_{1-20}$alkyl and optionally substituted aryl; more in particular from aryl and optionally substituted $C_{1-20}$alkyl;

$R^{21}$ is selected from $C_{1-20}$alkyl or aryl; wherein said $C_{1-20}$alkyl or aryl is optionally substituted with one or more groups selected from halo, hydroxy, cyano, $C_{1-6}$alkyl, cycloalkyl, heterocyclyl, aryl, heteroaryl, and alkoxy; more in particular optionally substituted with one group selected from cycloalkyl, aryl, hydroxy, alkoxy, and heterocyclyl;

$R^{21}$ is selected from aryl and $C_{1-20}$alkyl; wherein said $C_{1-20}$alkyl is optionally substituted with halo, hydroxy, cyano, $C_{1-6}$alkyl, cycloalkyl, heterocyclyl, aryl, heteroaryl, or alkoxy; more in particular with cycloalkyl, phenyl, hydroxy, alkoxy, and heterocyclyl;

$R^{22}$ is optionally substituted $C_{1-6}$alkyl; in particular $C_{1-6}$alkyl;

$R^3$ is selected from the group consisting of $Het^1$, $C_{1-20}$alkyl, aryl or heteroaryl; wherein said $C_{1-20}$alkyl, aryl or heteroaryl is substituted with 1, 2 or 3 substituents each independently selected from the group consisting of aryl, heteroaryl, $-(CH_2)_p-C(=O)-OR^{21}$, -$Het^1$, $-NH-Het^1$, $-O-Het^1$, $-S-Het^1$, $-S-C_{2-6}$alkyl, $-NH-C_{2-6}$alkyl, and $-O-C_{2-6}$alkyl;

Wherein said aryl, heteroaryl, $-O-C_{2-6}$alkyl, $-NH-C_{2-6}$alkyl, or $-S-C_{2-6}$alkyl are each independently substituted with a substituent selected from the group consisting of $C(=O)-OR^{21}$, -$Het^1$, $-O-Het^1$, $-NH-Het^1$, and $-S-Het^1$;

in particular $R^3$ is selected from the group consisting of $Het^1$, $C_{1-20}$alkyl, aryl or heteroaryl; wherein said $C_{1-20}$alkyl, aryl or heteroaryl is substituted with 1, 2 or 3 substituents each independently selected from the group consisting of $-(CH_2)_p-C(=O)-OR^{21}$, -$Het^1$, $-NH-Het^1$, $-O-Het^1$, and $-S-Het^1$;

more in particular $R^3$ is selected from the group consisting of $Het^1$, $C_{1-20}$alkyl, or aryl; wherein said $C_{1-20}$alkyl or aryl is substituted with 1, 2 or 3; preferably 1; substituents each independently selected from the group consisting of $-(CH_2)_p-C(=O)-OR^{21}$, -$Het^1$, and $-S-Het^1$;

even more in particular $R^3$ is selected from the group consisting of $Het^1$, $C_{1-20}$alkyl, or phenyl; wherein said $C_{1-20}$alkyl or phenyl is substituted with 1, 2 or 3; preferably 1; substituents each independently selected from the group consisting of $-(CH_2)_p-C(=O)-OR^{21}$, -$Het^1$, and $-S-Het^1$;

$R^4$ is selected from the group consisting of hydrogen or $C_{1-6}$alkyl; in particular hydrogen;

$R^3$ and $R^4$ together with the nitrogen atom to which they are attached form a heterocycle substituted with one substituent selected from the group consisting of $C_{1-20}$alkyl, aryl or heteroaryl; wherein said $C_{1-20}$alkyl, aryl, or heteroaryl is substituted with 1, 2 or 3 substituents each independently selected from the group consisting of aryl, heteroaryl, $-C(=O)-OR^{21}$, -$Het^1$, $-O-Het^1$, $-S-Het^1$, $-S-C_{2-6}$alkyl, $-NH-C_{2-6}$alkyl, and $-O-C_{2-6}$alkyl;

Wherein said $-O-C_{2-6}$alkyl, $-NH-C_{2-6}$alkyl, or $-S-C_{2-6}$alkyl are each independently substituted with a substituent selected from the group consisting of $C(=O)-OR^{21}$, -$Het^1$, $-O-Het^1$, $-NH-Het^1$, and $-S-Het^1$;

$R^3$ and $R^4$ can not be taken together with the nitrogen atom to which they are attached to form a heterocycle;

$R^1$ can not be selected from aryl or heteroaryl substituted with $-O-CH_2-C(=O)-OR^{21}$;

$R^1$ can not be selected from indolyl;

if $R^1$ is phenyl, then said phenyl can not be substituted with $-(CH_2)_p-C(=O)-OR^{21}$ in the para position;

if $R^1$ is phenyl, then said phenyl is substituted in the meta position; in particular said phenyl is substituted in the meta position with a substituent selected from the group consisting of:
- $-(CH_2)_pC(=O)-OR^{21}$;
- $-(CH_2)_pC(=O)-NR^3R^4$;
- $-(CH_2)_p-C(=O)-SR^{22}$;
- $Het^1$, $-O-Het^1$, $-NH-Het^1$, or $-S-Het^1$; and
- $-O-C_{1-6}$alkyl, $-NH-C_{1-6}$alkyl, $-S-C_{1-6}$alkyl, or $-C_{1-6}$alkyl; wherein said $-O-C_{1-6}$alkyl, $-NH-C_{1-6}$alkyl, $-S-C_{1-6}$alkyl, or $-C_{1-6}$alkyl are each independently substituted with a substituent selected from the group consisting of $-C(=O)-OR^{21}$, $-C(=O)-NR^3R^4$, $Het^1$, $-O-Het^1$, $-NH-Het^1$, and $-S-Het^1$;

in particular a substituent selected from the group consisting of:
- $-(CH_2)_p-C(=O)-OR^{21}$;
- $-(CH_2)_p-C(=O)-NR^3R^4$;
- $-(CH_2)_p-C(=O)-SR^{22}$; and
- $-O-C_{1-6}$alkyl, $-S-C_{1-6}$alkyl, or $-C_{1-6}$alkyl; wherein said $-O-C_{1-6}$alkyl, $-S-C_{1-6}$alkyl, or $-C_{1-6}$alkyl are each independently substituted with a substituent selected from the group consisting of $-C(=O)-OR^{21}$, $-C(=O)-NR^3R^4$, $Het^1$, $-O-Het^1$, $-NH-Het^1$, and $-S-Het^1$; in particular $-O-C_{1-6}$alkyl substituted with $-C(=O)-NR^3R^4$;

said compound of formula I is not

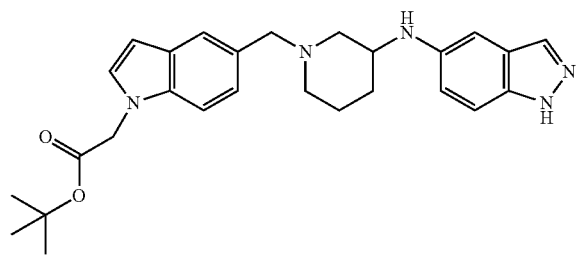 [SMILES: CC(C)(C)OC(=O)Cn1ccc2cc(CN3CCCC(Nc4ccc5[nH]ncc5c4)C3)ccc21]

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

In a preferred embodiment, the compounds of the present invention are useful as kinase inhibitors, more in particular for the inhibition of at least one ROCK kinase, selected from ROCKI and ROCKII, in particular soft ROCK inhibitors.

The present invention further provides the use of a compound as defined hereinbefore or the use of a composition comprising said compound, as a human or veterinary medicine, in particular for prevention and/or treatment of at least one disease or disorder, in which ROCK is involved, such as diseases linked to smooth muscle cell function, inflammation, fibrosis, excessive cell proliferation, excessive angiogenesis, hyperreactivity, barrier dysfunction, neurodegeneration, and remodeling.

In a further embodiment, the invention provides the use of a compound as defined hereinbefore, or the use of a composition comprising said compound in the prevention and/or treatment of at least one disease or disorder selected from the group comprising eye diseases; airway diseases; throat, nose and ear diseases; intestinal diseases; cardiovascular and vascular diseases; inflammatory diseases; neurological and CNS disorders: proliferative diseases; kidney diseases; sexual dysfunction; bone diseases; benign prostatic hyperplasia, transplant rejection, spasm, hypertension, chronic obstructive bladder disease, and allergy.

In a preferred embodiment, the invention provides the use of a compound as defined hereinbefore or the use of a composition comprising said compound in the prevention and/or treatment of eyes diseases including but not limited to retinopathy, optic neuropathy, glaucoma and degenerative retinal diseases such as age-related macular degeneration, retinitis pigmentosa and inflammatory eye diseases, and/or for preventing, treating and/or alleviating complications and/or symptoms associated therewith.

In another preferred embodiment, the invention provides the use of a compound as defined hereinbefore or the use of a composition comprising said compound in the prevention and/or treatment of airway diseases; including but not limited to pulmonary fibrosis, emphysema, chronic bronchitis, asthma, fibrosis, pneumonia, cytsis fibrosis, chronic obstructive pulmonary disease (COPD); bronchitis and rhinitis and respiratory distress syndrome, and/or for preventing, treating and/or alleviating complications and/or symptoms associated therewith.

In a further embodiment, the invention provides the use of a compound as defined hereinbefore or the use of a composition comprising said compound in the prevention and/or treatment of cardiovascular and vascular diseases: including but not limited to pulmonary hypertension and pulmonary vasoconstriction, and/or for preventing, treating and/or alleviating complications and/or symptoms associated therewith and/or alleviating complications and/or symptoms associated therewith.

In a further embodiment, the invention provides the use of a compound as defined hereinbefore or the use of a composition comprising said compound in the prevention and/or treatment of Throat, Nose and Ear diseases: including but not limited to sinus problems, hearing problems, toothache, tonsillitis, ulcer and rhinitis, In a further embodiment, the invention provides the use of a compound as defined hereinbefore or the use of a composition comprising said compound in the prevention and/or treatment of skin diseases: including but not limited to hyperkeratosis, parakeratosis, hypergranulosis, acanthosis, dyskeratosis, spongiosis and ulceration.

In a further embodiment, the invention provides the use of a compound as defined hereinbefore or the use of a composition comprising said compound in the prevention and/or treatment of Intestinal diseases; including but not limited to inflammatory bowel disease (IBD), colitis, gastroenteritis, ileus, ileitis, appendicitis and Crohn's disease.

In yet another embodiment, the invention provides the use of a compound as defined hereinbefore or the use of a composition comprising said compound in the prevention and/or treatment of inflammatory diseases: including but not limited to contact dermatitis, atopic dermatitis, psoriasis, rheumatoid arthritis, juvenile rheumatoid arthritis, ankylosing spondylitis, psoriatic arthritis, inflammatory bowel disease, Crohn's disease and ulcerative colitis, and/or for preventing, treating and/or alleviating complications and/or symptoms and/or inflammatory responses associated therewith.

In another embodiment, the invention provides the use of a compound as defined hereinbefore or the use of a composition comprising said compound in the prevention, treatment and/or management of neurological and CNS disorders: including but not limited to neuropathic pain. The present compounds are therefore suitable for preventing neurodegeneration and stimulating neurogeneration in various neurological disorders, and/or for preventing, treating and/or alleviating complications and/or symptoms associated therewith.

In another embodiment, the invention provides the use of a compound as defined hereinbefore or the use of a composition comprising said compound in the prevention and/or treatment of proliferative diseases: such as but not limited to cancer of breast, colon, intestine, skin, head and neck, nerve, uterus, kidney, lung, ovary, pancreas, prostate, or thyroid gland; Castleman disease; sarcoma; malignoma; and melanoma; and/or for preventing, treating and/or alleviating complications and/or symptoms and/or inflammatory responses associated therewith.

In another embodiment, the invention provides the use of a compound as defined hereinbefore or the use of a composition comprising said compound in the prevention and/or treatment of kidney diseases: including but not limited to renal fibrosis or renal dysfunction; and/or for preventing, treating and/or alleviating complications and/or symptoms and/or inflammatory responses associated therewith.

In another embodiment, the invention provides the use of a compound as defined hereinbefore or the use of a composition comprising said compound in the prevention and/or treatment of sexual dysfunction: including but not limited to hypogonadism, bladder disease, hypertension, diabetes, or pelvic surgery; and/or to treat sexual dysfunction associated with treatment using certain drugs, such as drugs used to treat hypertension, depression or anxiety.

In another embodiment, the invention provides the use of a compound as defined hereinbefore or the use of a composition comprising said compound in the prevention and/or treatment of bone diseases: including but not limited to osteoporosis and osteoarthritis; and/or for preventing, treating and/or alleviating complications and/or symptoms and/or inflammatory responses associated therewith.

In another embodiment, the invention provides the use of a compound as defined hereinbefore or the use of a composition comprising said compound in the prevention and/or treatment of diseases and disorders such as benign prostatic hyperplasia, transplant rejection, spasm, chronic obstructive bladder disease, and allergy, and/or for preventing, treating and/or alleviating complications and/or symptoms associated therewith.

In a preferred embodiment the present invention provides the use of a compound as defined hereinbefore or the use of a composition comprising said compound in the prevention and/or treatment of glaucoma, macular degeneration (including age-related macular degeneration), asthma, sexual dysfunction or COPD.

Method of Treatment

The present invention further provides a method for the prevention and/or treatment of at least one disease or disorder selected from the group comprising eye diseases; airway diseases; throat, nose and ear diseases; intestinal diseases; cardiovascular and vascular diseases; inflammatory diseases; neurological and CNS disorders: proliferative diseases; kidney diseases; sexual dysfunction; bone diseases; benign prostatic hyperplasia; transplant rejection; spasm; hypertension; chronic obstructive bladder disease and allergy; said method comprising administering to a subject in need thereof a therapeutic effective amount of a compound or a composition as defined herein.

In a preferred embodiment, the invention provides a method for the prevention and/or treatment of eye diseases including but not limited to retinopathy, optic neuropathy, glaucoma and degenerative retinal diseases such as age-related macular degeneration, retinitis pigmentosa and inflammatory eye diseases; said method comprising administering to a subject in need thereof a therapeutic effective amount of a compound or a composition as defined herein.

In another preferred embodiment, the invention provides a method for the prevention and/or treatment of airway diseases including but not limited to pulmonary fibrosis, emphysema, chronic bronchitis, asthma, fibrosis, pneumonia, cystic fibrosis, chronic obstructive pulmonary disease (COPD) bronchitis, rhinitis, and respiratory distress syndrome; said method comprising administering to a subject in need thereof a therapeutic effective amount of a compound or a composition as defined herein.

In another embodiment, the invention provides a method for the prevention and/or treatment of cardiovascular and vascular diseases: including but not limited to pulmonary hypertension and pulmonary vasoconstriction; said method comprising administering to a subject in need thereof a therapeutic effective amount of a compound or a composition as defined herein.

In another embodiment, the invention provides a method for the prevention and/or treatment of inflammatory diseases: including but not limited to contact dermatitis, atopic dermatitis, psoriasis, rheumatoid arthritis, juvenile rheumatoid arthritis, ankylosing spondylitis, psoriatic arthritis, inflammatory bowel disease, Crohn's disease and ulcerative colitis; said method comprising administering to a subject in need thereof a therapeutic effective amount of a compound or a composition as defined herein.

In a further embodiment, the invention provides a method for the prevention and/or treatment of Throat, Nose and Ear diseases: including but not limited to sinus problems, hearing problems, toothache, tonsillitis, ulcer and rhinitis; said method comprising administering to a subject in need thereof a therapeutic effective amount of a compound or a composition as defined herein.

In a further embodiment, the invention provides a method for the prevention and/or treatment of skin diseases: including but not limited to hyperkeratosis, parakeratosis, hypergranulosis, acanthosis, dyskeratosis, spongiosis and ulceration; said method comprising administering to a subject in need thereof a therapeutic effective amount of a compound or a composition as defined herein.

In a further embodiment, the invention provides a method for the prevention and/or treatment of Intestinal diseases; including but not limited to inflammatory bowel disease (IBD), colitis, gastroenteritis, ileus, ileitis, appendicitis and Crohn's disease; said method comprising administering to a subject in need thereof a therapeutic effective amount of a compound or a composition as defined herein.

In another embodiment, the invention provides a method for the prevention and/or treatment of neurological and CNS disorders: including but not limited to neuropathic pain. The present compounds are therefore suitable for preventing neurodegeneration and stimulating neurogeneration in various neurological disorders; said method comprising administering to a subject in need thereof a therapeutic effective amount of a compound or a composition as defined herein.

In another embodiment, the invention provides a method for the prevention and/or treatment of proliferative diseases: such as but not limited to cancer of breast, colon, intestine, skin, head and neck, nerve, uterus, kidney, lung, liver, ovary, pancreas, prostate, or thyroid gland; Castleman disease; sarcoma; malignoma; and melanoma; said method comprising administering to a subject in need thereof a therapeutic effective amount of a compound or a composition as defined herein.

In another embodiment, the invention provides a method for the prevention and/or treatment of kidney diseases: including but not limited to renal fibrosis or renal dysfunction; said method comprising administering to a subject in need thereof a therapeutic effective amount of a compound or a composition as defined herein.

In another embodiment, the invention provides a method for the prevention and/or treatment of sexual dysfunction: including but not limited to hypogonadism, bladder disease, hypertension, diabetes, or pelvic surgery; and/or to treat sexual dysfunction associated with treatment using certain drugs, such as drugs used to treat hypertension, depression or anxiety; said method comprising administering to a subject in need thereof a therapeutic effective amount of a compound or a composition as defined herein.

In another embodiment, the invention provides a method for the prevention and/or treatment of bone diseases: including but not limited to osteoporosis and osteoarthritis; said method comprising administering to a subject in need thereof a therapeutic effective amount of a compound or a composition as defined herein.

In another embodiment, the invention provides a method for the prevention and/or treatment of diseases and disorders such as benign prostatic hyperplasia, transplant rejection, spasm, chronic obstructive bladder disease, and allergy; said method comprising administering to a subject in need thereof a therapeutic effective amount of a compound or a composition as defined herein.

In a preferred embodiment, the invention provides a method for the prevention and/or treatment of glaucoma, degenerative retinal diseases, age-related macular degeneration, retinopathy, asthma, sexual dysfunction or COPD; said method comprising administering to a subject in need thereof a therapeutic effective amount of a compound or a composition as defined herein.

In the invention, particular preference is given to compounds of Formula I or any subgroup thereof that in the inhibition assay for ROCK described below inhibit ROCK with an $IC_{50}$ value of less than 10 µM, preferably less than 1 µM, more preferably less than 0.1 µM.

Said inhibition may be effected in vitro and/or in vivo, and when effected in vivo, is preferably effected in a selective manner, as defined above.

The term "ROCK-mediated condition" or "disease", as used herein, means any disease or other deleterious condition in which is known to play a role. The term "ROCK-mediated condition" or "disease" also means those diseases or conditions that are alleviated by treatment with a ROCK inhibitor. Accordingly, another embodiment of the present invention relates to treating or lessening the severity of one or more diseases in which ROCK is known to play a role.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. No. 6,372,778, U.S. Pat. No. 6,369,086, U.S. Pat. No. 6,369,087 and U.S. Pat. No. 6,372,733.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases.

Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. In addition, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

Generally, for pharmaceutical use, the compounds of the inventions may be formulated as a pharmaceutical preparation or pharmaceutical composition comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for parenteral administration (such as by intramuscular or subcutaneous injection, for intravitreal injection, for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is again made to for instance U.S. Pat. No. 6,372,778, U.S. Pat. No. 6,369,086, U.S. Pat. No. 6,369,087 and U.S. Pat. No. 6,372,733, as well as to the standard handbooks, such as the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, creams, lotions, soft and hard gelatin capsules, suppositories, eye drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. . . .

In addition, co-solvents such as alcohols may improve the solubility and/or the stability of the compounds. In the preparation of aqueous compositions, addition of salts of the compounds of the invention can be more suitable due to their increased water solubility.

For the treatment of pain, the compounds of the invention may be used locally. For local administration, the compounds may advantageously be used in the form of a spray, ointment or transdermal patch or another suitable form for topical, transdermal and/or intradermal administration.

For ophthalmic application, solutions, gels, tablets and the like are often prepared using a physiological saline solution, gel or excipient as a major vehicle. Ophthalmic formulations should preferably be prepared at a comfortable pH with an appropriate buffer system.

More in particular, the compositions may be formulated in a pharmaceutical formulation comprising a therapeutically effective amount of particles consisting of a solid dispersion of the compounds of the invention and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

It may further be convenient to formulate the compounds in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds according to the invention involves a pharmaceutical composition whereby the compounds are incorporated in hydrophilic polymers and applying this mixture as a coat film over many small beads, thus yielding a composition with good bio-availability which can conveniently be manufactured and which is suitable for preparing pharmaceutical dosage forms for oral administration. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The preparations may be prepared in a manner known per se, which usually involves mixing at least one compound according to the invention with the one or more pharmaceutically acceptable carriers, and, if desired, in combination with other pharmaceutical active compounds, when necessary under aseptic conditions. Reference is again made to standard handbooks, such as the latest edition of Remington's Pharmaceutical Sciences.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the invention, e.g. about 10, 25, 50, 100, 200, 300 or 400 mg per unit dosage.

The compounds can be administered by a variety of routes including the oral, rectal, ocular, transdermal, or intranasal routes, depending mainly on the specific preparation used and the condition to be treated or prevented, (e.g. eye drops for the treatment of eye diseases or dry powder inhaler for the treatment of lung diseases). The at least one compound of the invention will generally be administered in an "effective amount", by which is meant any amount of a compound of the Formula I or any subgroup thereof that, upon suitable administration, is sufficient to achieve the desired therapeutic or prophylactic effect in the individual to which it is administered. Usually, depending on the condition to be prevented or treated and the route of administration, such an effective amount will usually be between 0.001 to 1000 mg per kilogram body weight day of the patient per day, more often between 0.1 and 500 mg, such as between 1 and 250 mg, for example about 5, 10, 20, 50, 100, 150, 200 or 250 mg, per kilogram body weight day of the patient per day, which may be administered as a single daily dose, divided over one or more daily doses, or essentially continuously, e.g. through an implantable medical device or slow release formulations. The amount(s) to be administered, the route of administration and the further treatment regimen may be determined by the treating clinician, depending on factors such as the age, gender and general condition of the patient and the nature and severity of the disease/symptoms to be treated.

Reference is again made to U.S. Pat. No. 6,372,778, U.S. Pat. No. 6,369,086, U.S. Pat. No. 6,369,087 and U.S. Pat. No. 6,372,733 and the further prior art mentioned above, as well as to the standard handbooks, such as the latest edition of Remington's Pharmaceutical Sciences.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compositions of the present invention can be mixed with suitable additives, such as excipients, stabilizers, or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For injection the compound according to the invention, if desired with the substances customary therefore such as solubilizers, emulsifiers or further auxiliaries are brought into solution, suspension, or emulsion. The compounds of the invention can also be lyophilized and the lyophilizates obtained used, for example, for the production of injection preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquefy and/or dissolve in the rectal cavity to release the drug.

In preferred embodiments, the compounds and compositions of the invention are used locally, for instance topical or in both absorbed and non-adsorbed applications.

The compositions are of value in the veterinary field, which for the purposes herein not only includes the prevention and/or treatment of diseases in animals, but also—for economically important animals such as cattle, pigs, sheep, chicken, fish, etc.—enhancing the growth and/or weight of the animal and/or the amount and/or the quality of the meat or other products obtained from the animal. Thus, in a further aspect, the invention relates to a composition for veterinary use that contains at least one compound of the invention and at least one suitable carrier (i.e. a carrier suitable for veterinary use). The invention also relates to the use of a compound of the invention in the preparation of such a composition.

The invention will now be illustrated by means of the following synthetic and biological examples, which do not limit the scope of the invention in any way.

EXAMPLES

A. Physicochemical Properties of the Compounds

A.1. Compound Purity

Unless indicated otherwise, the purity of the compounds was confirmed by liquid chromatography/mass spectrometry (LC/MS), as follows:

HPLC system: Waters 2690 with photodiode array detector Waters 996; Column: C18; radient: solvent A ($H_2O$/formic acid 26.5 nM) 0%, to solvent B ($CH_3CN$/formic acid 17 nM) 80% in 3 min. Flow: 2.75 ml/min.

Mass spectrometer: Micromass Platform LC. Ionization: electrospray (polarity: negative and positive).

A.2. Attribution of the Configuration:

The Cahn-Ingold-Prelog system was used to attribute the absolute configuration of chiral center, in which the four groups on an asymmetric carbon are ranked to a set of sequences rules. Reference is made to Cahn; Ingold; Prelog *Angew. Chem. Int. Ed. Engl.* 1966, 5, 385-415.

A.3. Stereochemistry:

It is known by those skilled in the art that specific enantiomers (or diastereoisomers) can be obtained by different methods such as, but not limited to chiral resolution (for example, salts formed with optically active acids or bases may be used to form diastereoisomeric salts that can facilitate the separation of optically active isomers of the compounds of Formula I or any subgroup thereof), assymetric synthesis or preparative chiral chromatography (using different column such as Chiralcel OD-H (tris-3,5-dimethylphenylcarbamate, 46×250 or 100×250 mm, 5 μm), Chiralcel OJ (tris-methylbenzoate, 46×250 or 100×250 mm, 5 μm), Chiralpak AD (tris-3,5-dimethylphenylcarbamate, 46×250 mm, 10 μm) and Chiralpak AS (tris-(S)-1-phenylethylcarbamate, 46×250 mm, 10 μm) from Chiral Technologies Europe (Illkirch, France)). Whenever it is convenient, stereoisomers can be obtained starting from commercial materials with known configuration (such compounds include aminoacids for instance).

A.4. Name of the Molecules

The software MDL ISIS™/Draw 2.3 was used to assign the name of the molecules.

B. Compound Synthesis

B.1. Intermediates

The compounds of the invention may be prepared by methods well known to those skilled in the art, and as described in the synthetic and experimental procedures shown below.

Intermediate 1:
5-(Piperidin-3-ylamino)-indazole-1-carboxylic acid tert-butyl ester

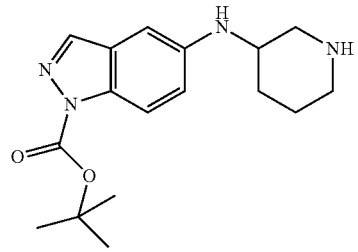 [SMILES: CC(C)(C)OC(=O)n1ncc2cc(NC3CCCNC3)ccc21]

To a solution of 5-nitro-indazole (200 g, 1.2 mol, 1.0 eq) in THF (2 L). DMAP (22 g, 0.18 mol, 0.15 eq) and TEA (248 g, 2.4 mol, 2.0 eq) were then added. The reaction mixture was stirred at 30° C. for 20 min, then $Boc_2O$ (320 g, 1.5 mol, 1.2 eq) was added to the reaction mixture in one portion. The reaction mixture was stirred at 30° C. for 16 hrs, evaporated and the residue was dissolved in DCM (2 L), The DCM solution was washed with aq HCL (0.5M) (1 L×3) and $H_2O$ (1 L×3), dried over $MgSO_4$ and concentrated to dryness to give the Boc protected 5-nitro-indazole (310 g, 96%).

To a solution of 5-nitro-indazole-1-carboxylic acid tert-butyl ester (300 g, 1.1 mol, 1.0 eq) in THF (3 L), and the mixture was hydrogenated at 40° C. with Pd/C (30 g) as catalyst in the presence of $H_2$ (50 psi). The reaction mixture was stirred at 40° C. for 16 hrs. TLC (PE:EA=4:1) showed the reaction was complete. After uptake of $H_2$, the catalyst was filtered off and the filtrate was evaporated to afford the crude 5-amino-indazole-1-carboxylic acid tert-butyl ester (252 g, 95%) which was used directly for next step without purification.

A mixture of 1-benzyl-piperidin-3-one hydrochloride (116 g, 0.52 mol, 1.2 eq) and TEA (43.5 g, 0.43 mol, 1.0 eq) in DCE (800 ml) was stirred at 30° C. for 1 hr. Then 5-amino-indazole-1-carboxylic acid tert-butyl ester (100 g, 0.43 mol, 1.0 eq) and $CH_3COOH$ (25.8 g, 0.43 mol, 1.0 eq) were added to the reaction mixture $NaBH(OAc)_3$ (273 g, 1.29 mol, 3.0 eq) was added in one portion after 30 min. The mixture was stirred at 30° C. for 16 hrs. LC-MS showed the reaction was complete. 1 L DCM was added to the reaction mixture and the organic layer was washed with saturated. $NaHCO_3$ (800 ml*3) and $H_2O$ (500 ml*3), dried over $Na_2SO_4$ and concentrated by rotavapor. The crude product was purified by column chromatography on silica gel using DCM: $CH_3OH$=60:1 to give the 5-(1-benzyl-piperidin-3-ylamino)-indazole-1-carboxylic acid tert-butyl ester (131 g, 75%).

The previous compound (120 g, 0.3 mol, 1.0 eq) was dissolved in $CH_3OH$ (1.5 L). And the mixture was hydrogenated at 40° C. with Pd/C (12 g) as catalyst in the presence of $H_2$ (50 psi). The reaction mixture was stirred at 40° C. for 16 hrs. TLC (DCM: $CH_3OH$=10:1) showed the reaction was complete. After uptake of $H_2$, the catalyst was filtered off and the filtrate was evaporated to afford the title product (90 g, 95%) which was used directly for next step without purification.

Intermediate 2: 5-[1-(3-Carboxy-benzyl)-piperidin-3-ylamino]-indazole-1-carboxylic acid tert-butyl ester (mixture of Boc and de-Boc-ed compound)

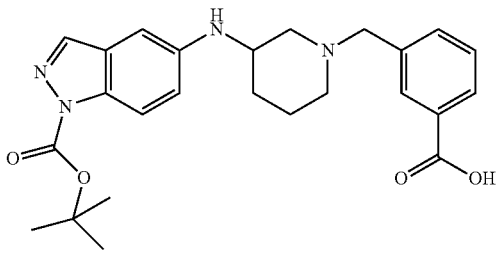 [SMILES: CC(C)(C)OC(=O)n1ncc2cc(NC3CCCN(Cc4cccc(C(=O)O)c4)C3)ccc21]

To a mixture of intermediate 1 (20 g, 0.063 mol, 1.0 eq) and (3-Formyl)-benzoic acid (11.4 g, 0.076 mol, 1.2 eq) and TEA (12.8 g, 0.126 mol, 2.0 eq) in DCE (200 ml) was added NaBH(OAc)$_3$ (26.8 g, 0.132 mol, 2.0 eq). The reaction mixture was stirred at 30° C. for 16 hrs. TLC (DCM/CH$_3$OH=10:1) showed the reaction was complete. 80 ml of DCM was added and the organic layer was washed with saturated NaHCO$_3$ (150 ml×3) and H$_2$O (150 ml×3), then dried on Na$_2$SO$_4$ and concentrated by rotavapor. The crude product was purified by prep HPLC to give the mixture of protected and deprotected Intermediate 5 (15.2 g, 54%).

Intermediate 3: 5-[1-(3-Carboxymethyl-benzyl)-piperidin-3-ylamino]-indazole-1-carboxylic acid tert-butyl ester (mixture of Boc and de-Boced compound)

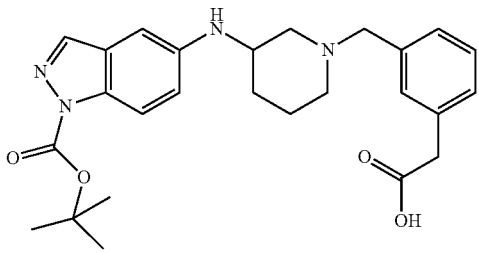 [SMILES: CC(C)(C)OC(=O)n1ncc2cc(NC3CCCN(Cc4cccc(CC(=O)O)c4)C3)ccc21]

A solution of m-Tolyl-acetic acid (15 g, 0.1 mol, 1.0 eq) in anhydrous CCl$_4$ (150 ml) was added to a solution of NBS (18.3 g, 0.105 mol, 1.05 eq) and AIBN (0.8 g, 0.0049 mol, 0.05 eq) in anhydrous CCl$_4$ (150 ml) at room temperature. The reaction mixture was refluxed for 16 hrs, cooled to room temperature, filtered off to give yellow solid which was washed with CCl$_4$ and dried to give desired product (3-bromomethyl-phenyl)-acetic acid (18 g 79.3%).

To a mixture of Intermediate 1 (20 g, 0.063 mol, 1.0 eq) and DIEA (16.3 g, 0.126 mol, 2.0 eq) in THF (200 ml) was added (3-bromomethyl-phenyl)-acetic acid (17.4 g, 0.076 mol, 1.2 eq). The reaction mixture was stirred at 80° C. for 16 hrs. TLC (DCM/CH$_3$OH=10:1) showed the reaction was complete. The solvent was evaporated and the residue was purified by Prep HPLC to give the mixture of protected and deprotected Intermediate 3 (14 g, 54%).

Intermediate 4: Isoquinolin-5-yl-piperidin-3-yl-amine hydrochloric acid salt

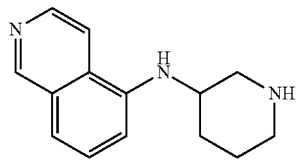

To a solution of isoquinoline (120 g, 0.929 mol) in H$_2$SO$_4$ (1 L) was added KNO$_3$ (112.6 g, 1.115 mol) at −15° C. (portionwise). The mixture was stirred at room temperature for 2 hours. TLC (petroleum ether:ethyl acetate=2:1) showed the reaction was complete. The mixture was added to water (3 L) at 0° C. The mixture was adjusted to pH 8 by the addition of NH$_4$OH and filtered. The filter cake was washed with methyl tertbutyl ether (1 L×2) and concentrated in vacuo to give 5-nitro-isoquinoline (160 g, 94%) as a yellow solid.

To a solution of 5-nitro-isoquinoline (150 g, 0.861 mol) in EtOH/H$_2$O=4:1 (5 L) was added NH$_4$Cl (92.2 g, 1.723 mol) and Fe (193 g, 3.445 mol) at room temperature. Then the mixture was heated to 80° C. and stirred for 10 hours. TLC (petroleum ether:ethyl acetate=1:1) showed the reaction was complete. The mixture was cooled to room temperature and filtered though a pad of celite. The filter cake was washed with EtOH (2 L×2). The filtrate was concentrated in vacuo to remove most of EtOH. The residue was extracted with EtOAc (500 ml×10). The combined layers were dried over Na$_2$SO$_4$, filtered and then concentrated in vacuo to afford 5-amino-isoquinoline (67 g, 54%) as a yellow solid.

To a solution of 5-amino-isoquinoline (47 g, 0.320 mol) in CH$_3$COOH (1800 mL) was added 3-amino-piperidine-1-carboxylic acid tert-butyl ester (69.6 g, 0.376 mol) and Na$_2$SO$_4$ (267 g, 1.88 mol) at room temperature. The mixture was stirred at room temperate for 0.5 hour. Then to the mixture was added NaBH(OAc)$_3$ (84.6 g, 0.376 mol) little by little. The mixture was stirred at room temperature for 18 hours. The mixture was adjusted to pH 8 by the addition of K$_2$CO$_3$ and extracted with EtOAc(2 L×3). (The combined layers were dried over Na$_2$SO$_4$, filtered and then concentrated in vacuo to afford crude product, which was purified by column chromatography on silica gel (petroleum ether:ethyl acetate=5:1) to give 3-(isoquinolin-5-ylamino)-piperidine-1-carboxylic acid tert-butyl ester (55 g, 53%) as a yellow oil.

To a solution of 3-(isoquinolin-5-ylamino)-piperidine-1-carboxylic acid tert-butyl ester (80 g, 0.244 mol) in EtOAc (1000 mL) was added HCl-EtOAc (1000 mL) at room temperature. The mixture was stirred at room temperature for 2.5 hours. TLC (methylene chloride:methanol=10:1) showed the reaction was complete. The reaction mixture was filtered. The filtered cake was dried under vacuum to give the title compound (66 g, 100%) as a yellow solid.

Intermediate 5: 3-[3-(Isoquinolin-5-ylamino)-piperidin-1-ylmethyl]-benzoic acid

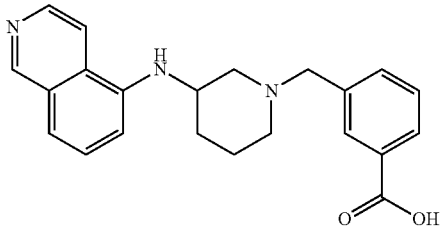 [SMILES: O=C(O)c1cccc(CN2CCCC(Nc3cccc4cnccc34)C2)c1]

To a solution of Intermediate 4 (10 g×2, 0.0379 mol×2) in DCE (400 mL×2) was added Et$_3$N (9.2 g×2, 0.0910 mol×2) and MgSO$_4$ (20×2, 0.139 mol×2), and stirred for 0.5 h at 30° C. 3-formylbenzoic acid (6.26 g×2, 0.0417 mol×2) and AcOH (5.46 g×2, 0.0910 mol×2) was added. The reaction mixture was stirred at 30° C. for 0.5 hours. NaBH(OAc)$_3$ (24.1 g×2, 0.1137 mol×2) was added and the reaction mixture was stirred at 30° C. overnight. TLC (methylene dichloride:methanol=10:1) showed the reaction was complete. The reaction mixture was filtered. The filtered cake was washed with CH$_2$Cl$_2$, the filtrate was washed with brine, dried over Na$_2$SO$_4$ and concentrated in vacuo, and purified by preparative HPLC to give Intermediate 5 (10.2 g, 37.2%) as a yellow solid.

Intermediate 6: 3-[3-(Isoquinolin-5-ylamino)-pyrrolidin-1-ylmethyl]-benzoic acid

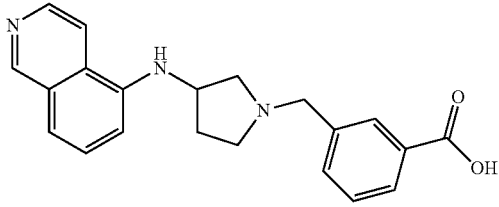 [SMILES: O=C(O)c1cccc(CN2CCC(Nc3cccc4cnccc34)C2)c1]

To a homogenous solution of isoquinolin-5-amine (15 g, 104 mmol) and tert-butyl 3-oxopyrrolidine-1-carboxylate (23.12 g, 125 mmol, 1.2 eq) in AcOH (300 mL) at 0° C. was added dropwise a solution of NaBH(OAc)$_3$ (44.1 g, 208 mmol, 2 eq) in AcOH (200 mL). The mixture was stirred at room temperature overnight and concentrated to dryness. Then, the residue was adjusted to pH 10 by addition of saturated aqueous solution of Na$_2$CO$_3$ and extracted with DCM (×3). The combined organic layers were dried over Na$_2$SO$_4$, filtered and then concentrated in vacuo to afford the expected compound, which was used directly in the next step without further purification.

To a solution of previous compound (104 mmol) in diethylether (10 was bubbled HCl for 1 h. The suspension was stirred for 5 h and the solvent evaporated. Then, the residue was dissolved in water and the pH adjusted to pH>12 by addition of NaOH 5M. The aqueous layer was extracted with DCM (3×) and the combined organic layers, dried over Na$_2$SO$_4$, filtered and concentrated under vacuum to give the expected compound (20.5 g, 92%) as a brown powder.

To a suspension of the previous compound (10 g, 46.9 mmol) in anhydrous THF (100 mL) was added 3-formylbenzoic acid (7.74 g, 51.6 mmol, 1.1 eq) and the mixture was stirred at 50° C. for 15 min. Then a white slurry solution of NaBH(OAc)$_3$ (29.8 g, 141 mmol, 3 eq) in THF (60 mL) was added to the mixture, stirred at room temperature overnight and concentrated to dryness. Finally the residue is purified by C18 column chromatography to give intermediate 6 (8 g, 49%) as a brown powder.

Intermediate 7: 5-Bromo-1-(tetrahydro-2H-pyran-2-yl)-1H-indazole

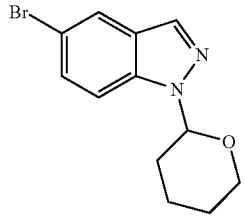 [SMILES: Brc1ccc2c(cnn2C2CCCCO2)c1]

To a suspension of 5-bromo-1H-indazole (2.5 g, 12.69 mmol, 1.0 eq) in DCM (10 ml) was added dihydropyran (3.2 g, 38 mmol, 3.0 eq) and a catalytic amount of PTSA (12% in AcOH, 1.8 ml, 0.1 eq). The mixture was stirred overnight and neutralized by addition of sodium bicarbonate. Then the organic layer was sequentially washed with 10% citric acid and brine, dried on Na$_2$SO$_4$ and concentrated under vacuum. The resulting residue was purified by chromatography on silica gel, eluting with DCM to give the expected compound as a colorless liquid (3.57 g, 82%).

Intermediate 8: 3-(2-Amino-ethylsulfanyl)-dihydro-furan-2-one

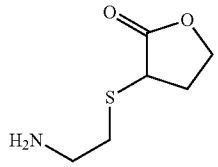

To a solution of 3-Bromo-dihydro-furan-2-one (2.49 g, 15.1 mmol) and 2-(Boc-amino)ethanethiol (2.9 g, 16.5 mmol) in CH$_3$CN (40 ml) was added K$_2$CO$_3$ (4.14 g, 30 mmol. The mixture was stirred at 80° C. for 16 h and the solvent was evaporated to dryness. The residue was then purified by column chromatography (PE/EtOAc=4/1) to give the expected Boc protected Intermediate 8 (3.8 g) as colorless oil.

The previous compound (3.7 g, 14.16 mmol) was dissolved in 10 ml of EtOAc. Then 40 mL of 4N HCl/EtOAc was added to the solution, which was then stirred at 25° C. for 2 h. The white solid was filtered and washed with PE to give the expected Intermediate 8 (2 g),

Intermediate 9: 4-(2-Amino-ethyl)-[1,3]dioxolan-2-one

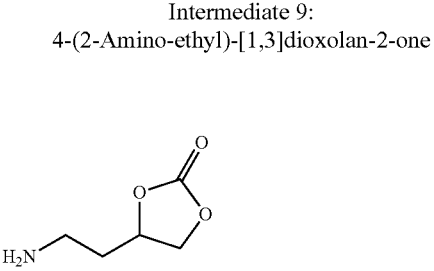

60 mL saturated solution of NH$_3$ in CH$_3$OH was added to 4-bromo-but-1-ene (3 mL) quickly in a 100 mL autoclave reactor. Then the mixture was stirred at 90° C. for 16 hours in the autoclave. After reaction, the solvent was concentrated under vacuum to give the hydrobromide salt of but-3-enylamine (12 g, 95%) as a yellow power.

To a suspension of the previous compound (12 g, 0.08 mol) in CH$_2$Cl$_2$ (10 was added a solution of K$_2$CO$_3$ (33 g, 0.24 mol) in water (80 mL) under N$_2$. The bi-phasic mixture was cooled to 0° C. and Cbz-Cl (22 g, 0.128 mol) was added dropwise. After 15 min of stirring at the temperature, the reaction mixture was stirred for 14 hours at room temperature. After the reaction was completed, to the mixture was added CH$_2$Cl$_2$ and water, the organic layer was dried over anhydrous Na$_2$SO$_4$, concentrated under vacuum and purified through silica gel chromatography (petroleum ether/ethyl acetate=3:1) to give the corresponding Cbz protected compound (12.2 g, 75%) as colorless oil.

To a stirred solution of the above compound (12.2 g, 59.5 mmol) in acetone/H$_2$O (60 mL/50 mL) was added NMO (7.3 g, 62.5 mmol) and OsO$_4$ (303 mg, 1.2 mmol) at room temperature under N$_2$. After addition of OsO$_4$, the color of reaction solution turned black. Then the mixture was stirred at room temperature for 10 h. TLC (CH$_2$Cl$_2$/MeOH=10:1) showed the starting material was consumed completely. The mixture was evaporated under vacuo. To the residue was added water and extracted with ethyl acetate. The organic layer was dried over anhydrous Na$_2$SO$_4$, concentrated under vacuum and purified through silica gel chromatography (CH$_2$Cl$_2$/MeOH=10:1) to give the corresponding diol (12 g, 85%) as pale solid.

To a solution of the diol (9 g, 37.66 mmol) in CH$_2$Cl$_2$ (200 mL) was added triethylamine (15.2 g, 151 mmol) at −20~30° C. under N$_2$. After several minutes, triphosgene (5.5 g, 18.83 mmol) was added to the mixture dropwise at this temperature and stirred at −20~30° C. for half an hour. Then the mixture was stirred at room temperature for 15 h. TLC (CH$_2$Cl$_2$/MeOH=10:1) showed the starting material was almost consumed. To the mixture was added water and extracted with ethyl acetate.

The organic layer was dried over anhydrous Na$_2$SO$_4$, concentrated under vacuum and purified through silica gel chromatography (CH$_2$Cl$_2$/MeOH=10:1) to give the corresponding cyclized dioxolane (6.5 g, 55%) as pale solid.

Intermediate 10: methyl 3-((4-aminopiperidin-1-yl)methyl)benzoate

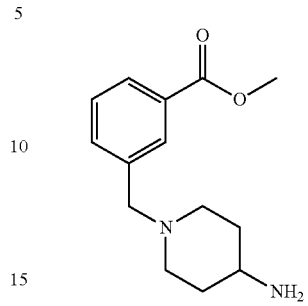

To a solution of tert-butyl piperidin-4-ylcarbamate (1.5 g, 7.48 mmol, 1.0 eq) and K$_2$CO$_3$ (1.55 g, 11.2 mmol, 1.5 eq) in CH$_3$CN (10 ml) was added methyl 3-(bromomethyl)benzoate (1.88 g, 8.22 mmol, 1.1 eq). The mixture was stirred overnight at room temperature and diluted in AcOEt. Then the organic layer was sequentially washed with sat. NaHCO$_3$ and brine, dried over Na$_2$SO$_4$ and concentrated under vacuum. The residue was purified by flash chromatography on silica gel, eluting with DCM/AcOEt (80/20 to 50/50) to give the expected Boc-protected intermediate 10 (1.7 g, 65%).

To a solution of the previous compound in DCM was bubbled HCl gas for 5 min and the reaction mixture was stirred at room temperature overnight. The precipitate was collected by filtration and washed with ether to give the HCl salt of the expected intermediate 10 as a white powder (1.5 g, 80%).

Intermediate 11: methyl 3-{[(4-aminocyclohexyl)amino]methyl}benzoate

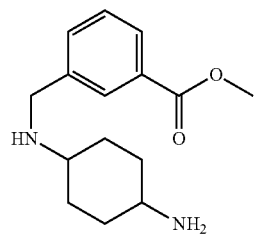 [SMILES: COC(=O)c1cccc(CNC2CCC(N)CC2)c1]

A suspension of trans-4-(tert-butoxycarbonylamino)cyclohexylamine (0.50 g, 2.33 mmol, 1.0 eq) and methyl 3-formylbenzoate (0.41 g, 2.45 mmol, 1.05 eq) in THF (13 ml) was stirred at 50° C. for 30 min. After cooling to room temperature, sodium triacetoxyborohydride (0.79 g, 3.73 mmol, 1.6 eq) was added and the reaction was stirred at ambient temperature till the reaction was completed. The reaction was quenched by addition of NaHCO$_3$ solution, extracted with EtOAc (3×) and washed sequentially with saturated NaHCO$_3$ solution and brine. The organic fraction was dried over Na$_2$SO$_4$ and concentrated under reduced pressure. The crude residue was purified by flash chromatography (silicagel) eluting with DCM/MeOH (99/1 to 91/9) to yield the Boc-protected intermediate as a white powder (0.54 g, 64%).

To a solution of the previous compound in DCM was bubbled HCl gas for 5 min and the reaction mixture was stirred at room temperature for 3 hrs. The precipitate was collected by filtration and washed with ether to give the HCl salt of the expected intermediate 11 as a white powder (0.47 g, 93%).

Intermediate 12: propyl 3-({3-[(isoquinolin-5-yl)amino]-8-azabicyclo[3.2.1]octan-8-yl}methypenzoate

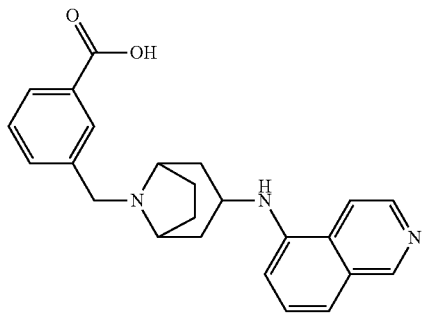 [SMILES: O=C(O)c1cccc(CN2C3CCC2CC(Nc2cccc4cnccc24)C3)c1]

To a homogenous solution of isoquinolin-5-amine (2.67 g, 18.5 mmol) and tert-butyl 3-amino-8-azabicyclo[3.2.1]octane-8-carboxylate (5 g, 125 mmol, 1.2 eq) in AcOH (60 mL) at 0° C. was added dropwise a solution of NaBH(OAc)$_3$ (7.84 g, 37 mmol, 2 eq) in AcOH (40 mL). The mixture was stirred at room temperature 5 days and concentrated to dryness. Then, the residue was adjusted to pH 10 by addition of saturated aqueous solution of Na$_2$CO$_3$ and extracted with DCM (×3). The combined organic layers were dried over Na$_2$SO$_4$, filtered and then concentrated in vacuo. The resulting residue was purified by flash chromatography (silica gel) eluting with DCM/MeOH (98/2) to afford the expected compound (1.4 g, 21%).

To a solution of previous compound (1.4 g, 3.96 mmol) in diethylether (40 mL) was bubbled HCl for 5 min. The suspension was stirred for 5 h and the solvent evaporated. Then, the residue was dissolved in water and the pH adjusted to pH>12 by addition of NaOH 5M. The aqueous layer was extracted with DCM (3×) and the combined organic layers, dried over Na$_2$SO$_4$, filtered and concentrated under vacuum to give the expected compound (900 mg, 90%) as a white powder.

To a suspension of the previous compound (900 mg, 3.55 mmol) in anhydrous THF (10 mL) was added 3-formylbenzoic acid (587 mg, 3.91 mmol, 1.1 eq) and the mixture was stirred at 50° C. for 15 min. Then a white slurry solution of NaBH(OAc)$_3$ (2.2 g, 10.66 mmol, 3 eq) in THF (6 mL) was added to the mixture, stirred at room temperature overnight and concentrated to dryness. Finally the residue is purified by C18 column chromatography to give intermediate 12 (670 mg, 49%) as a brown powder.

Intermediate 13: methyl 3-[(3-aminopyrrolidin-1-yl)methyl]benzoate

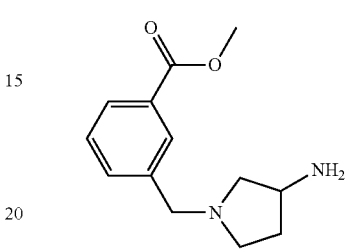

The Boc-protected intermediate (2.11 g, 63%) was prepared using similar conditions as for intermediate 10, starting from tert-butyl pyrrolidin-3-ylcarbamate (1.86 g). Boc-deprotection of the previous compound with HCl gas in DCM yielded the HCl salt of the expected intermediate 13 as a white powder (1.82 g, 94%).

B.1. Compounds of the Invention

General Procedures for Ester or Thioester Formation:

Protocol A

To a mixture of intermediate (200 mg, 1.0 eq) and TEA (3.0 eq) in CH$_3$CN (4 ml) was added HOBT (0.4 eq), EDCI (1.5 eq) and the chosen alcohol or thiol (1.5 eq). The reaction mixture was stirred at 30° C. for 16 hrs and the solvent concentrated to dryness. The crude product was purified by preparative HPLC to give the expected compound.

Protocol B

To a mixture of intermediate (200 mg, 1.0 eq) and TEA (3.0 eq) in CH$_3$CN (4 ml) was added HOBT (0.4 eq), EDCI (1.5 eq) and the chosen alcohol or thiol (1.5 eq). The reaction mixture was stirred at 30° C. for 16 hrs and the solvent concentrated to dryness. The resulting crude product was dissolved in DCM/TFA=7:1 (4 ml), the reaction mixture stirred at 30° C. for 16 hrs and concentrated under vacuum. The residue was purified by prep HPLC to give the expected compound.

The following compounds of the invention were prepared using this general procedure

| Compound | Intermediate | R—OH or R—SH | protocol |
|---|---|---|---|
| (structure) | 5 | Cyclopropyl methanol | A |

-continued

| Compound | Intermediate | R—OH or R—SH | protocol |
|---|---|---|---|
| 2 | 5 | Benzyl alcohol | A |
| 3 | 5 | Phenol | A |
| 4 | 3 | n-propanol | B |
| 5 | 5 | Ethylene glycol | A |
| 6 | 5 | ethanethiol | A |

-continued
| Compound | Intermediate | R—OH or R—SH | protocol |
|---|---|---|---|
| 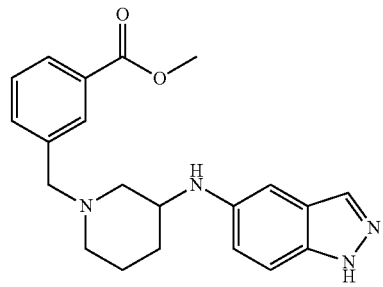 [SMILES: COC(=O)c1cccc(CN2CCCC(Nc3ccc4[nH]ncc4c3)C2)c1] 7 | 2 | Methanol | B |
| 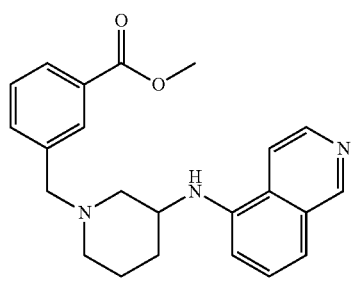 [SMILES: COC(=O)c1cccc(CN2CCCC(Nc3cccc4cnccc34)C2)c1] 8 | 5 | Methanol | A |
| 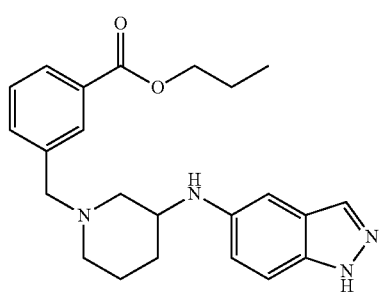 [SMILES: CCCOC(=O)c1cccc(CN2CCCC(Nc3ccc4[nH]ncc4c3)C2)c1] 9 | 2 | n-propanol | B |
| 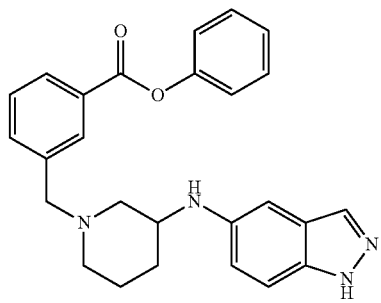 [SMILES: O=C(Oc1ccccc1)c1cccc(CN2CCCC(Nc3ccc4[nH]ncc4c3)C2)c1] 10 | 2 | Phenol | B |

-continued
| Compound | Intermediate | R—OH or R—SH | protocol |
|---|---|---|---|
| 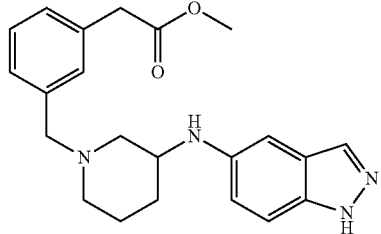 [SMILES: COC(=O)Cc1cccc(CN2CCCC(Nc3ccc4[nH]ncc4c3)C2)c1] 11 | 3 | Methanol | B |
| 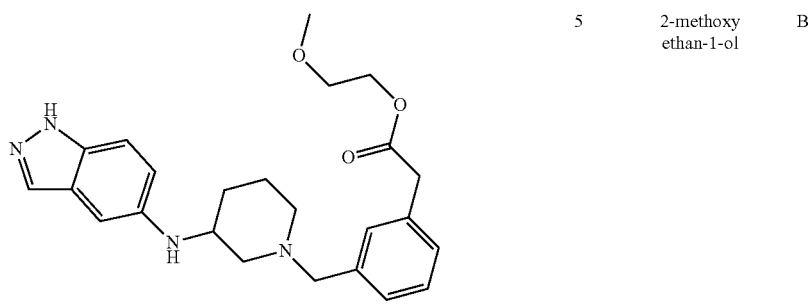 12 | 5 | 2-methoxy ethan-1-ol | B |
| 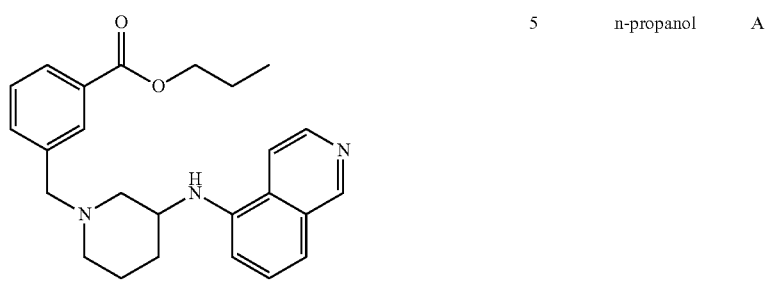 13 | 5 | n-propanol | A |
| 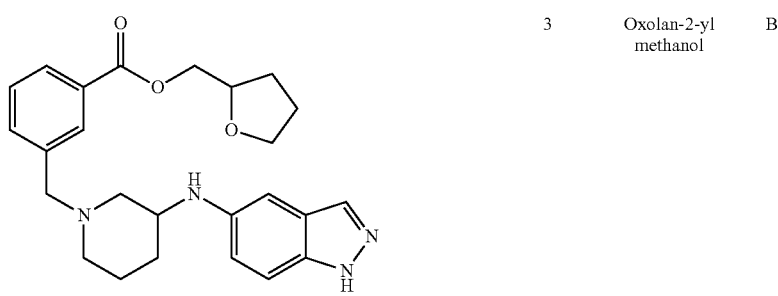 14 | 3 | Oxolan-2-yl methanol | B |

-continued
| Compound | Intermediate | R—OH or R—SH | protocol |
|---|---|---|---|
| 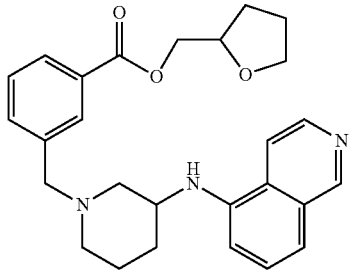 [SMILES: O=C(OCC1CCCO1)c1cccc(CN2CCCC(Nc3cccc4cnccc34)C2)c1] 15 | 5 | Oxolan-2-yl methanol | A |
| 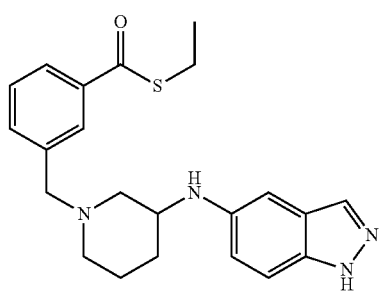 [SMILES: CCSC(=O)c1cccc(CN2CCCC(Nc3ccc4[nH]ncc4c3)C2)c1] 16 | 2 | ethanethiol | B |
| 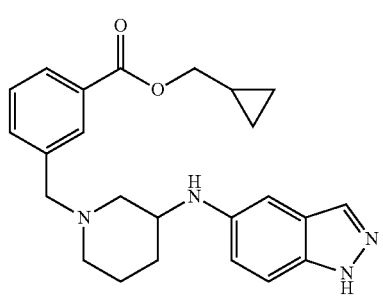 [SMILES: O=C(OCC1CC1)c1cccc(CN2CCCC(Nc3ccc4[nH]ncc4c3)C2)c1] 17 | 3 | Cyclopropyl methanol | B |
| 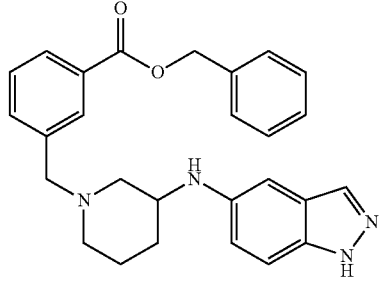 [SMILES: O=C(OCc1ccccc1)c1cccc(CN2CCCC(Nc3ccc4[nH]ncc4c3)C2)c1] 18 | 3 | Benzyl alcohol | B |

-continued
| Compound | Intermediate | R—OH or R—SH | protocol |
|---|---|---|---|
| 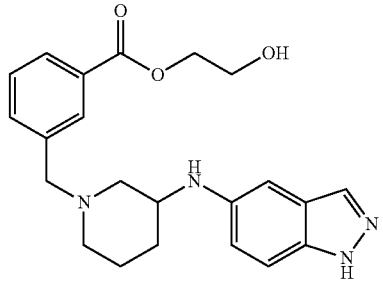 [SMILES: O=C(OCCO)c1cccc(CN2CCCC(Nc3ccc4[nH]ncc4c3)C2)c1] 19 | 3 | Ethylene glycol | B |
| 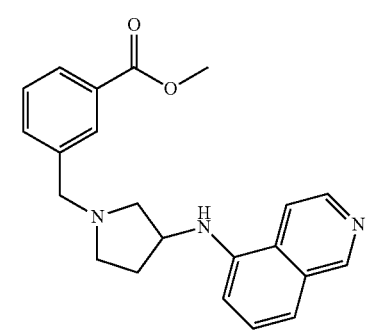 [SMILES: COC(=O)c1cccc(CN2CCC(Nc3cccc4cnccc34)C2)c1] 20 | 6 | Methanol | A |
| 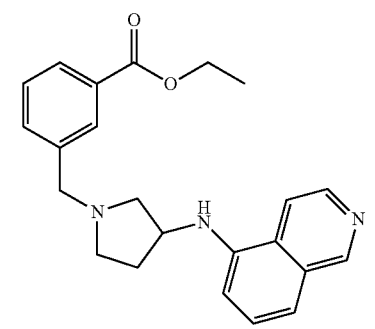 [SMILES: CCOC(=O)c1cccc(CN2CCC(Nc3cccc4cnccc34)C2)c1] 21 | 6 | Ethanol | A |
| 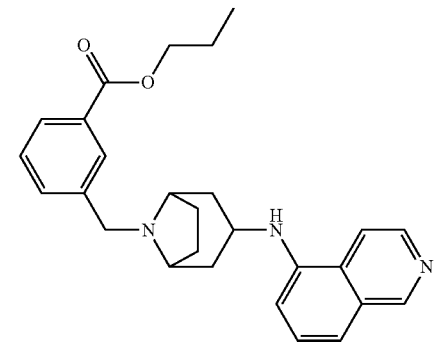 [SMILES: CCCOC(=O)c1cccc(CN2C3CCC2CC(Nc2cccc4cnccc24)C3)c1] 22 | 12 | Propanol | A |

General Procedure for Reductive Amination

To a mixture of intermediate (200 mg), selected aldehyde (1.2 eq) and TEA (100 µl) in DCM (4 ml) was added NaBH(OAc)$_3$ (1.5 eq). The reaction mixture was stirred at 30° C. for 16 hrs and concentrated to dryness. Then the crude product was dissolved in DCM/TFA=7:1 (4 ml). The reaction mixture was stirred at 30° C. for 16 hrs, concentrated and the crude product was purified by prep HPLC to give the expected compound.

The following compounds of the invention were prepared using this general procedure:

| Compound | | Intermediate | Aldehyde |
|---|---|---|---|
| 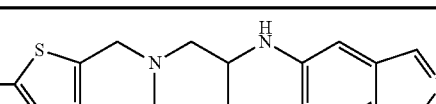 23 | | 1 | 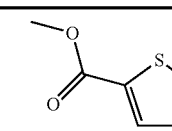 |
| 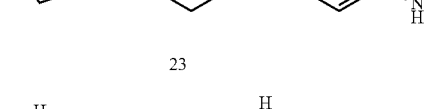 24 | | 1 |  |

General Procedures for Amide Formation

Protocol A

To a mixture of intermediate (200 mg, 1.0 eq) and R—NH$_2$ (2.0 eq) in CH$_3$CN (4 ml) was added HOBT (0.4 eq) and EDCI (1.5 eq). The reaction mixture was stirred at 30° C. for 16 hrs and concentrated to dryness. The resulting crude product was purified by prep HPLC to give the expected compound.

Protocol B

To a mixture of intermediate (200 mg, 1.0 eq) and R—NH2 (2.0 eq) in CH$_3$CN (4 ml) was added HOBT (0.4 eq) and EDCI (1.5 eq). The reaction mixture was stirred at 30° C. for 16 hrs and concentrated to dryness. The resulting crude product was dissolved in DCM/TFA=7:1 (4 ml). The reaction mixture was stirred at 30° C. for 16 hrs, concentrated and the crude product was purified by prep HPLC to give the expected compound.

Protocol C

To a solution of intermediate (100 mg, 1.0 eq), R—NH2 (1.5 eq) and triethylamine (3.0 eq) in DMF (2 ml) was added HATU (1.0 eq). The reaction mixture was stirred at 30° C. overnight and concentrated under vacuum. The resulting crude product was purified by prep. HPLC to give the expected compound.

Protocol D

To a solution of intermediate (100 mg, 1.0 eq), R—NH$_2$ (2.0 eq) and triethylamine (10.0 eq) in DMF (2 ml) was added HATU (1.5 eq). Then DMAP (1.0 eq) was added into the mixture. The reaction mixture was stirred at 50° C. overnight and concentrated under vacuum. The resulting crude product was purified by prep. HPLC to give the expected compound.

Protocol E

To a solution of intermediate (100 mg, 1.0 eq), R—NH$_2$ (1.5 eq) and triethylamine (3.0 eq) in DMF (2 ml) was added HATU (1.0 eq). The reaction mixture was stirred at 30° C. overnight and concentrated under vacuum. The crude product was dissolved in 4 ml of a solution of TFA in DCM (1:4) and the reaction mixture stirred at 30° C. for 4 hrs. Then the solvent was concentrated under vacuum and the crude product purified by prep. HPLC to give the expected compound.

Protocol F

To a solution of intermediate (100 mg, 1.0 eq), R—NH$_2$ (2.0 eq) and DIEA (6.0 eq) in DMF (1.5 ml) was added HATU (1.5 eq). Then HOBT (0.5 eq) was added into the mixture. The reaction mixture was stirred at 30° C. overnight. Then the solvent was concentrated under vacuum and the crude product purified by prep. HPLC to give the expected compound.

Protocol G

To a solution of intermediate (100 mg, 1.0 eq), R—NH$_2$ (2.0 eq) and DIEA (6.0 eq) in DMF (1.5 ml) was added HATU (1.5 eq). Then HOBT (0.5 eq) was added into the mixture. The reaction mixture was stirred at 30° C. overnight and concentrated under vacuum. The crude product was dissolved in 4 ml of a solution of TFA in DCM (1:4) and the reaction mixture stirred at 30° C. for 4 hrs. Then the solvent was concentrated under vacuum and the crude product purified by prep. HPLC to give the expected compound.

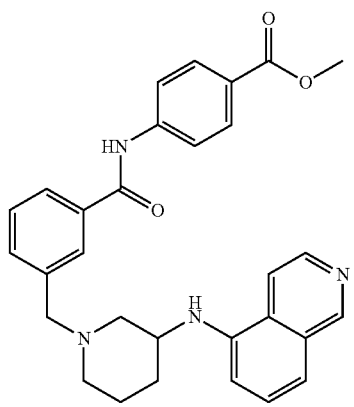 [SMILES: COC(=O)c1ccc(NC(=O)c2cccc(CN3CCCC(Nc4cccc5cnccc45)C3)c2)cc1]

Example

Compound 25

To a solution of intermediate 5 (100 mg, 277 umol, 1.0 eq), methyl 4-aminobenzoate (554 µmol, 2.0 eq) and DIEA (1662 µmol, 6.0 eq) in DMF (1.5 ml) was added HATU (157.9 mg, 415.5 μmol, 1.5 eq). Then HOBT (138.5 μmol, 0.5 eq) was added into the mixture. The reaction mixture was stirred at 30° C. overnight. The solvent was then evaporated under vacuum and the crude product was purified by prep. HPLC to give the TFA salt of the expected compound (30 mg, 17%) as a white powder. RT: 2.058 min. m/z (MH+)=495.2

The following compounds of the invention were prepared using the general procedures described above:

| Compound | Intermediate | R—NH$_2$ | protocol |
|---|---|---|---|
| 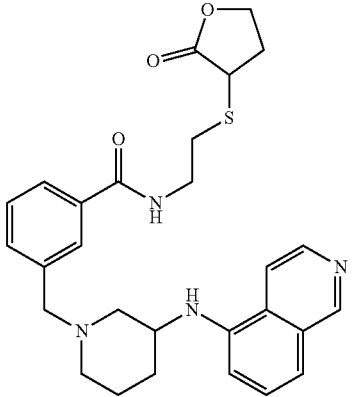 [SMILES: O=C(NCCSC1CCOC1=O)c1cccc(CN2CCCC(Nc3cccc4cnccc34)C2)c1] 26 | 5 | 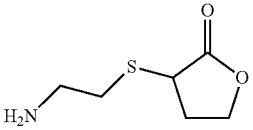 | A |
| 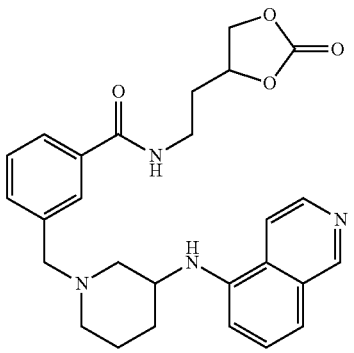 [SMILES: O=C1OCC(CCNC(=O)c2cccc(CN3CCCC(Nc4cccc5cnccc45)C3)c2)O1] 27 | 5 | 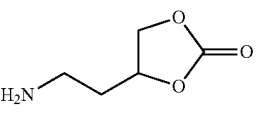 | A |
| 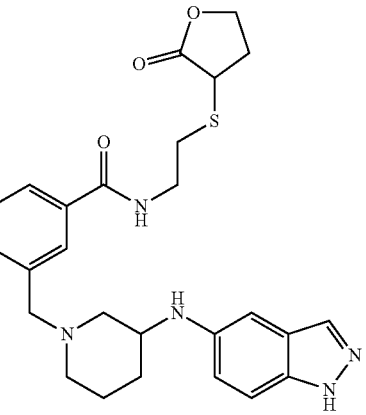 28 | 2 | 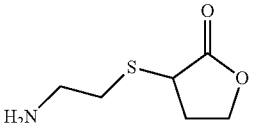 | B |

-continued
| Compound | Intermediate | R—NH₂ | protocol |
|---|---|---|---|
| 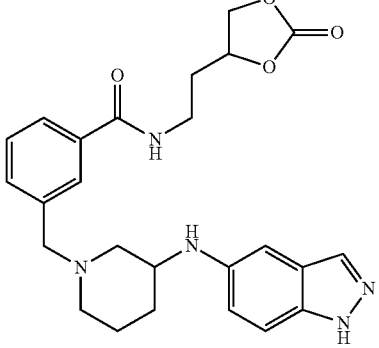 29 | 2 | 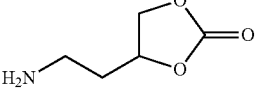 | B |
| 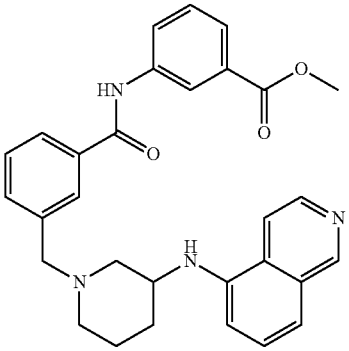 [SMILES: COC(=O)c1cccc(NC(=O)c2cccc(CN3CCCC(Nc4cccc5cnccc45)C3)c2)c1] 30 | 5 | 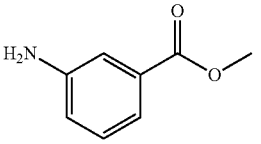 | D |
| 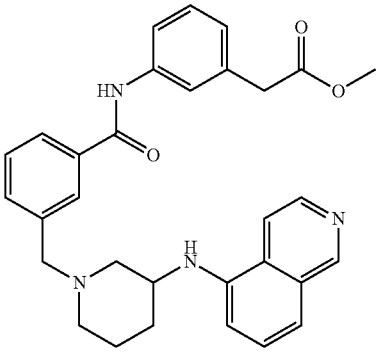 [SMILES: COC(=O)Cc1cccc(NC(=O)c2cccc(CN3CCCC(Nc4cccc5cnccc45)C3)c2)c1] 31 | 5 | 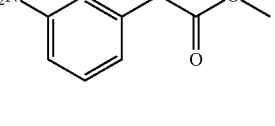 | D |
| 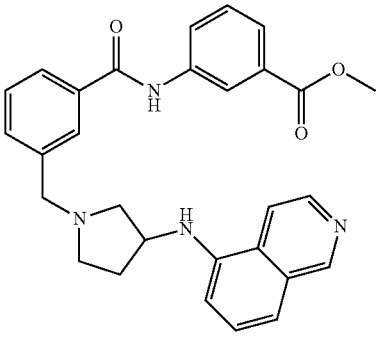 [SMILES: COC(=O)c1cccc(NC(=O)c2cccc(CN3CCC(Nc4cccc5cnccc45)C3)c2)c1] 32 | 6 | 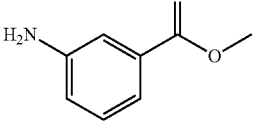 | C |

-continued

| Compound | Intermediate | R—NH₂ | protocol |
|---|---|---|---|
| 33 | 6 | 3-aminophenyl methyl acetate | C |
| 25 | 5 | methyl 4-aminobenzoate | F |
| 34 | 5 | methyl 2-(4-aminophenyl)acetate | D |

-continued
| Compound | Intermediate | R—NH$_2$ | protocol |
|---|---|---|---|
| 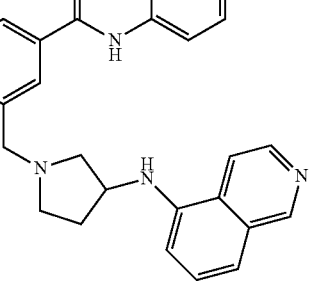<br>35 | 6 | 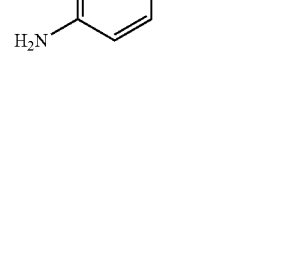 | C |
| 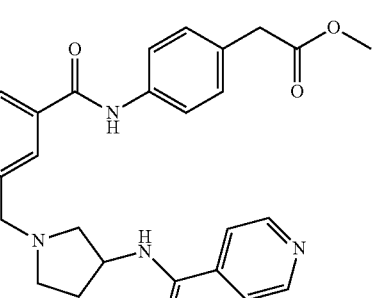<br>36 | 6 | 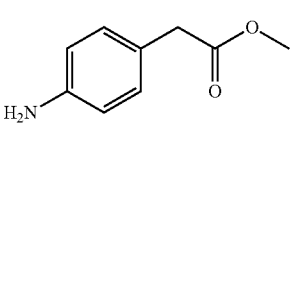 | C |
| 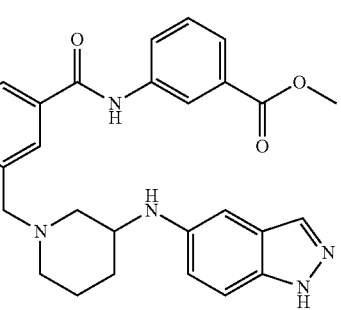<br>37 | 2 | 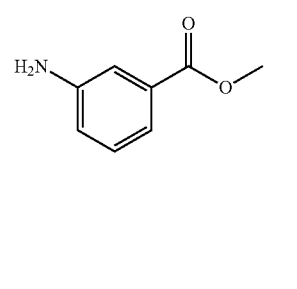 | E |
| 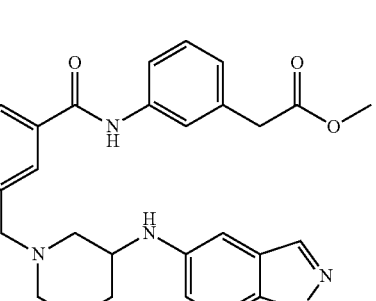<br>38 | 2 | 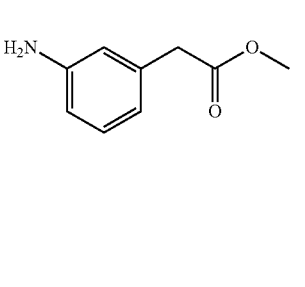 | E |

-continued

| Compound | Intermediate | R—NH₂ | protocol |
|---|---|---|---|
| 39 | 2 | methyl 4-aminobenzoate | G |
| 40 | 2 | methyl 2-(4-aminophenyl)acetate | E |
| 41 | 3 | methyl 3-aminobenzoate | E |
| 42 | 3 | methyl 2-(3-aminophenyl)acetate | E |

-continued

| Compound | Intermediate | R—NH₂ | protocol |
|---|---|---|---|
| 43 | 3 | methyl 4-aminobenzoate | G |
| 44 | 3 | methyl 2-(4-aminophenyl)acetate | E |
| 45 | 6 | propyl 2-(4-aminophenyl)acetate | C |
| 46 | 6 | 2-methoxyethyl 2-(4-aminophenyl)acetate | C |

-continued
| Compound | Intermediate | R—NH$_2$ | protocol |
|---|---|---|---|
| 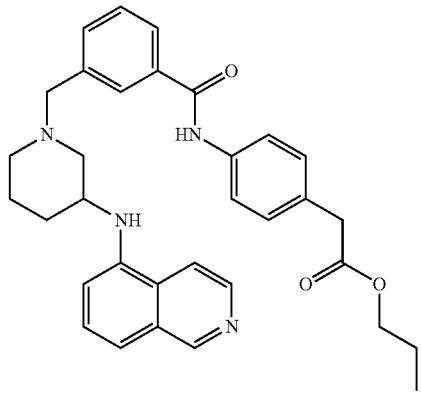<br>47 | 5 | 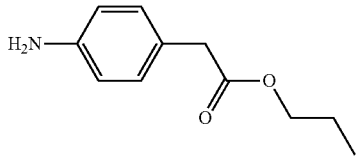 | D |
| 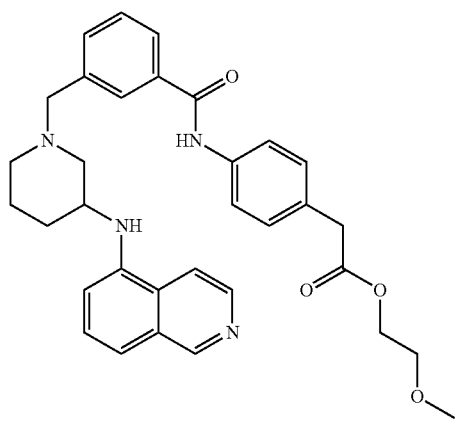<br>48 | 5 | 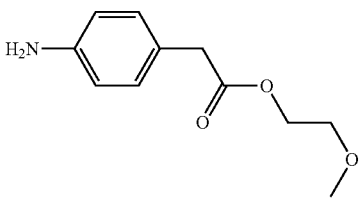 | D |
| 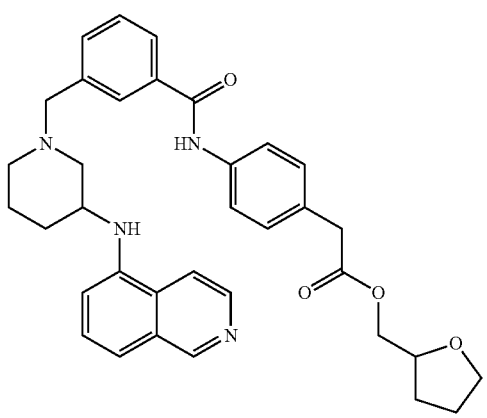 [SMILES: O=C(Cc1ccc(NC(=O)c2cccc(CN3CCCC(Nc4cccc5cnccc45)C3)c2)cc1)OCC1CCCO1]<br>49 | 5 | 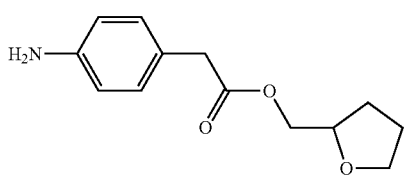 | D |

-continued

| Compound | Intermediate | R—NH₂ | protocol |
|---|---|---|---|
| 50 | 2 | (4-aminophenyl)acetic acid propyl ester | E |
| 51 | 2 | (4-aminophenyl)acetic acid 2-methoxyethyl ester | E |
| 52 | 2 | (4-aminophenyl)acetic acid 2-(pyrrolidin-1-yl)ethyl ester | E |

Compound 53 (methyl 3-({4-[(isoquinolin-5-yl)amino]piperidin-1-yl}methyl)benzoate)

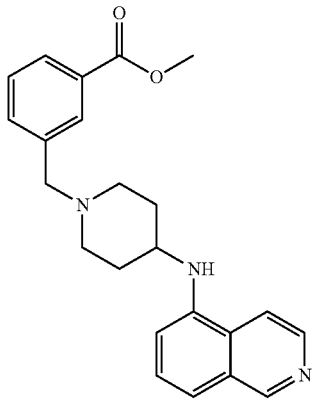 [SMILES: COC(=O)c1cccc(CN2CCC(Nc3cccc4cnccc34)CC2)c1]

To a solution of 5-bromoisoquinoline (419 mg, 2.01 mmol, 1.0 eq) in toluene (5 ml) were added intermediate 10 (500 mg, 2.01 mmol, 1.0 eq), palladium acetate (67.5 mg, 0.3 mmol, 0.15 eq), rac-(+/−)-BINAP (187.5 mg, 0.3 mmol, 0.15 eq) and cesium carbonate (2.35 g, 7.22 mmol, 3.6 eq). Then the reaction mixture was degassed three times with nitrogen and stirred at 80° C. overnight.

The mixture was diluted with AcOEt and washed with brine, dried over Na$_2$SO$_4$, filtered and concentrated under vacuum. The crude product was purified by flash chromatography on C18, eluting with CH$_3$CN/H$_2$O to give the title compound (144 mg, 19%) as a white powder.

Purity and identity of the title compound was checked by liquid chromatography/mass spectrometry (LC/MS). HPLC system: Shimadzu SIL-20A/20AC. Column: Luna C18 50*2.1 mm; 5 μm. Gradient: 0°-0.5°: mobile phase A (water, 10 mM ammonium acetate) 100%; 0.5°-3.0°: from 100% mobile phase A to 98% mobile phase B (Acetonitrile); 3'-4': 2% mobile phase A and 98% mobile phase B. Flow: 0.6 ml/min. Mass spectrometer: Applied Biosystems MDS SCIEX, 3200 Q Trap.

For title compound: RT:3.65 min; m/z (MH+):376.5.

Compound 54 (methyl 3-[({4-[(isoquinolin-5-yl)amino]cyclohexyl}amino)methyl]benzoate)

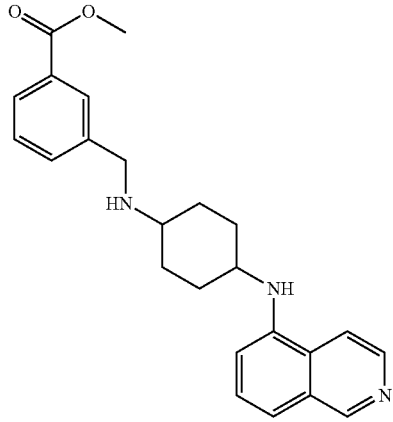 [SMILES: COC(=O)c1cccc(CNC2CCC(Nc3cccc4cnccc34)CC2)c1]

Compound 54 (19 mg, 4% yield) was synthesized using the same procedure as for compound 53, by reaction of 5-bromo-isoquinoline (250 mg) with the HCl salt of intermediate 11 (403 mg). Purity and identity of title compound was checked by liquid chromatography/mass spectrometry, using the same equipment and setup as for compound 53. RT: 3.25 min. m/z (MH+)=390.4

Compound 55: methyl 3-({3-[(4-methylisoquinolin-5-yl)amino]pyrrolidin-1-yl}methyl)benzoate

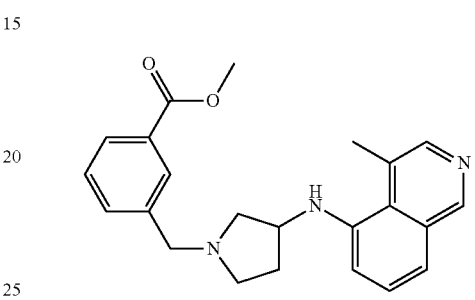

Compound 55 (51 mg, 10% yield) was synthesized using the same procedure as for compound 53, by reaction of 5-bromo-4-methylisoquinoline (300 mg) with intermediate 13 (420 mg). Purity and identity of title compound was checked by liquid chromatography/mass spectrometry, using the same equipment and setup as for compound 53. RT: 3.81 min. m/z (MH+)=376.4

Met1 (3-({3-[(1H-indazol-5-yl)amino]piperidin-1-yl}methyl)benzoic acid)

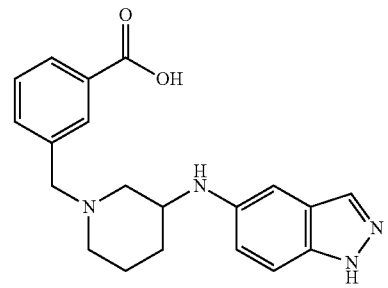 [SMILES: O=C(O)c1cccc(CN2CCCC(Nc3ccc4[nH]ncc4c3)C2)c1]

Met1 does not represent a compound of the invention, but is instead the metabolite resulting from ester hydrolysis of compounds 7, 9, 10, 14, 16, 17, 18, 19 by carboxylic ester hydrolases or pseudoesterases. In laboratory, Met1 can be readily prepared via saponification of compound 7 with LiOH; such a process being well known to people skilled in the art. Metabolites from other compounds of the invention can be readily prepared via saponification with LiOH.

The purpose of Met1 is here to demonstrate the lack of functional activity of metabolites resulting from ester hydrolysis of compounds of the invention by carboxylic ester hydrolases or pseudoesterases. Once prepared in a laboratory through saponification of the parent compound of the invention, Met1 or similar metabolites can be evaluated in functional assays, to confirm their lack of functional activity.

C. In Vitro and In Vivo Assays

C.1. ROCK Inhibitory Activity Screening
C.1.1. Kinase Inhibition (ROCKI & ROCKII)

On-target activity against ROCK was measured in a biochemical assay, using the following reagents: Base Reaction buffer; 20 mM Hepes (pH 7.5), 10 mM $MgCl_2$, 1 mM EGTA, 0.02% Brij35, 0.02 mg/ml BSA, 0.1 mM $Na_3VO_4$, 2 mM DTT, 1% DMSO. Required cofactors are added individually to each kinase reaction. The reaction procedure first involved the preparation of a peptide substrate in a freshly prepared reaction buffer. Required cofactors were then added to the substrate solution. ROCK (1 nM final concentration) was then delivered to the substrate solution. After gentle mix, DMSO solutions of the test compounds were added to the enzyme. Substrate mix $^{33}$P-ATP (specific activity 0.01 μCi/μl final) was then delivered into the reaction mixture to initiate the reaction. The kinase reaction was incubated for 120 min. at room temperature. Reactions were then spotted onto P81 ion exchange paper (Whatman #3698-915). Filters were washed extensively in 0.1% Phosphoric acid. A radiometric count was then performed and $IC_{50}$ values were subsequently determined.

The $IC_{50}$ values obtained (in accordance with the protocol set forth above) are represented as follows: "+++" means $IC_{50}$ below 0.1 μM, "++" means $IC_{50}$ between 0.1 μM and 1 μM; "+" means $IC_{50}$ between 1 and 10 μM and "ND" means "not determined yet".

| # Cpds | $IC_{50}$ ROCK2 |
|---|---|
| 1 | +++ |
| 2 | ++ |
| 3 | ++ |
| 4 | +++ |
| 5 | +++ |
| 6 | ++ |
| 7 | +++ |
| 8 | ++ |
| 9 | +++ |
| 10 | +++ |
| 11 | +++ |
| 12 | +++ |
| 13 | ++ |
| 14 | +++ |
| 15 | +++ |
| 16 | +++ |
| 17 | +++ |
| 18 | +++ |
| 19 | +++ |
| 20 | +++ |
| 21 | ++ |
| 22 | ND |
| 23 | +++ |
| 24 | +++ |
| 25 | ND |
| 26 | +++ |
| 27 | +++ |
| 28 | +++ |
| 29 | +++ |
| 30 | +++ |
| 31 | ND |
| 32 | +++ |
| 33 | +++ |
| 34 | +++ |
| 35 | +++ |
| 36 | +++ |
| 37 | +++ |
| 38 | ND |
| 39 | ND |
| 40 | ND |
| 41 | +++ |
| 42 | +++ |
| 43 | ND |
| 44 | +++ |
| 45 | ND |
| 46 | ND |
| 47 | ND |
| 48 | ND |
| 49 | ND |
| 50 | ND |
| 51 | ND |
| 52 | ND |
| 53 | ND |
| 54 | ND |
| 55 | ND |

C.1.2. Myosin Light Chain Phosphorylation Assay

Rat smooth muscle cell line A7r5 is used. The endogenous expression of ROCK esults in a constitutive phosphorylation of the regulatory myosin light chain at T18/S19. A7r5 cells were plated in DMEM supplemented with 10% FCS in multiwall cell culture plates. After serum starvation overnight, cells were incubated with compounds in serum-free medium.

Quantification of MLC-T18/S19 phosphorylation is assesses in 96 well-plates via ELISA using a phspho-MLC-T18/S19 specific antibody and a secondary detection antibody. Raw data were converted into percent substrate phosphorylation relative to high controls, which were set to 100%.

$EC_{50}$ values were determined using GraphPad Prism 5.01 software using a nonlinear regression curve fit with variable hill slope.

The $EC_{50}$ values obtained (in accordance with the protocols set forth above) are represented as follows: "+++" means $EC_{50}$ below 0.3 μM, "++" means $EC_{50}$ between 0.3 μM and 1 μM; "+" means $EC_{50}$ between 1 and 10 μM and "–" means $EC_{50}$>10 μM.

| # Cpds | $EC_{50}$ |
|---|---|
| 7 | + |
| 9 | ++ |
| 14 | +++ |
| 15 | + |
| 17 | ++ |
| 19 | ++ |
| 26 | ++ |
| 28 | ++ |
| 32 | +++ |
| Met1 | – |

In addition to this data, FIG. 1 provides the concentration-response curves for compound 14 and Met1, the predicted metabolite of compound 14 resulting from ester hydrolysis by carboxylic ester hydrolases. As will be demonstrated in point C2, such hydrolysis readily occurs in plasma, but not in aqueous humor. FIG. 1 further exemplifies the important difference of activity between compound 14 which represents a functionally active compound and its metabolite Met1, which is a functionally inactive compound; and thereby further demonstrates the soft character of compound 14.

C.2. Pharmacological Characterization

C.2.1. Stability Assay in Human and/or Mouse Plasma

Compounds are incubated at a concentration of 1 μM in rat (mice or rabbit) or human plasma. Samples are taken at fixed time points and the remnant of compound is determined by LC-MS/MS after protein precipitation. Half life is expressed in minutes.

| # Cpd | t½ mice plasma | t½ human plasma |
|---|---|---|
| 1 | ND | 49 |
| 2 | ND | 53 |
| 3 | ND | 19 |
| 10 | ND | <5 |
| 14 | ND | <5 |
| 15 | ND | 5 |
| 17 | ND | 25 |
| 18 | ND | 26 |
| 26 | 2.5 | 5 |
| 27 | ND | 4 |
| 28 | 2.2 | <5 |
| 29 | ND | <5 |
| 31 | ND | <5 |
| 32 | ND | 25 |
| 33 | ND | <4 |
| 36 | ND | 24 |
| 40 | ND | 40 |
| 41 | ND | 10 |
| 42 | ND | <5 |
| 44 | ND | <5 |

C.2.2. Stability Towards Drug Metabolizing Enzymes in Lung S9

A 1 µM solution of the ROCK inhibitors is incubated with a reaction mixture containing lung S9 (from smokers) as well as the cofactors NADPH, UDPGA, PAPS and GSH. Samples are collected at 0, 15, 30 and 60 minutes post incubation. Negative control samples incubated with ROCK inhibitors and S9 fraction in the absence of cofactors are run in parallel. By using LC-MS/MS analysis, the percent of ROCK compounds remaining at each time point, the metabolic half-life of the ROCK compounds (expressed in minutes) and the metabolic half-life of the control compounds are determined.

| # Cpd | t½ human lung S9 |
|---|---|
| 26 | >240 |
| 28 | >240 |
| 32 | >240 |

C.2.3. Stability Assay in Rabbit Aqueous Humor

Compounds are incubated at a concentration of 1 µM in rabbit aqueous humor (AH). Samples are taken at fixed time points and the remnant of compound is determined by LC-MS/MS after protein precipitation. Half life is expressed in minutes.

| # Cpd | t½ AH |
|---|---|
| 14 | >120 |
| 17 | >120 |
| 25 | >120 |
| 27 | 111 |
| 29 | >120 |
| 30 | >120 |
| 31 | >120 |
| 32 | >120 |
| 33 | 59 |
| 34 | >120 |
| 35 | >120 |
| 36 | >120 |
| 37 | >120 |
| 38 | >120 |
| 39 | >120 |
| 40 | >120 |
| 41 | >120 |
| 43 | >120 |

C.2.4. Intraocular Pressure (IOP) Lowering in Normotensive Rabbits

A detailed example of the IOP lowering effects of the compounds of the invention is here provided for compound 14. Compound 14 was here formulated as a 0.3% solution of pH=6.91 in Water/PEG 400 1:1.

IOP of to normotensive New Zeland White rabbits (n=3) was measured using a Tonolab tonometer, at 9h00, prior to compound administration.

At 9h30, one drop (50 µl) of the formulated solution was administered to rabbits, in the right eye (OD); while one drop (50 µl) of the vehicle solution was administered to the left eye (OS). IOP was then recorded in 1 h intervals until 17 h. As can be observed in the following table, a pronounced IOP decrease is observed following administration of compound 14 and is visible until 17 h. This decrease is considered as statistically significant (P≤0.05) until the 14 h time point, or 4.30 h after administration, demonstrating sustained activity of compound 14 in the eye.

| Time | Average IOP OS (mmHg) | Average IOP OD (mmHg) | SEM OS | SEM OD | P-value |
|---|---|---|---|---|---|
| 9 h | 9.00 | 9.89 | 0.33 | 0.40 | 0.17 |
| 10 h | 9.11 | 7.67 | 0.44 | 0.11 | 0.08 |
| 11 h | 8.44 | 6.44 | 0.11 | 0.11 | 0.00 |
| 12 h | 8.56 | 6.22 | 0.40 | 0.11 | 0.03 |
| 13 h | 8.44 | 7.00 | 0.40 | 0.19 | 0.05 |
| 14 h | 8.33 | 6.44 | 0.51 | 0.29 | 0.04 |
| 15 h | 8.56 | 7.67 | 0.44 | 0.40 | 0.33 |
| 16 h | 9.11 | 7.89 | 0.22 | 0.59 | 0.16 |
| 17 h | 9.00 | 8.11 | 0.00 | 0.29 | 0.09 |

Figure 2:
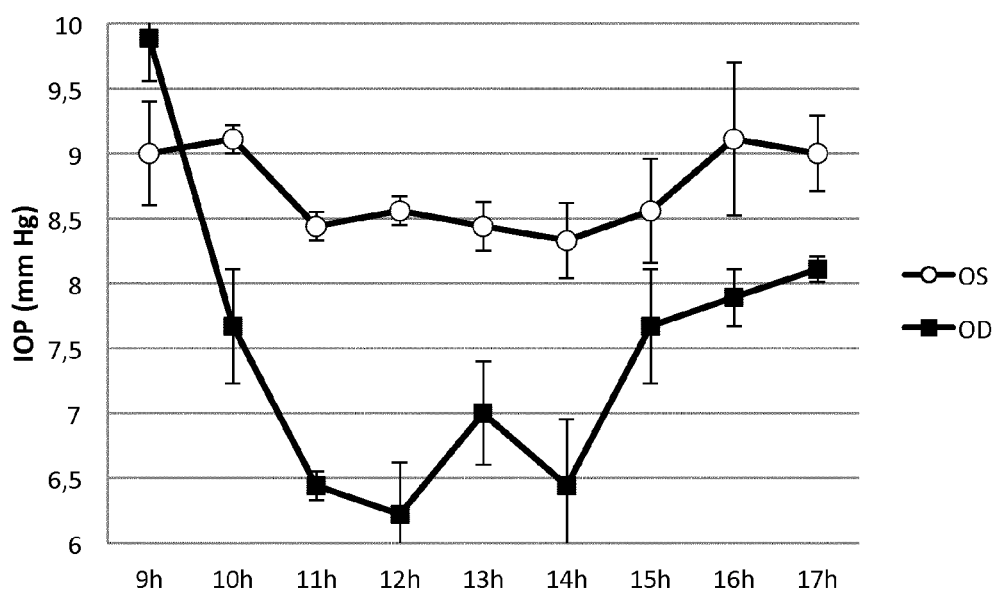
FIG. 2: Lowering of intra-ocular pressure followed over time for compound 14.

A graphical representation of this data is provided in FIG. 2.

C3: Enablement of the Soft ROCK Inhibitors

Compounds of the invention can be used as soft ROCK inhibitors for the treatment of ROCK-associated diseases. Examples disclosed hereinbelow in points C3.1 and C3.2 refer to the treatment of eye diseases or lung diseases, but do not limit the scope of the invention in any way. Comparison to structurally related ROCK inhibitors disclosed in prior art is provided.

C3.1: Soft ROCK Inhibitors for Eye Diseases

Compounds of the invention qualify as soft ROCK inhibitors for the treatment of ROCK-associated eye diseases. They display good inhibitory potency against ROCK, functional activity in cellular assay(s), low stability in systemic circulation, and good stability in the eye (estimated through stability in aqueous humor). Furthermore, they are converted converted into predictable species, displaying negligible functional activity.

A detailed example of soft ROCK inhibitors for the treatment of eye diseases is provided by compounds such 14 or 17. This example does not limit the applicability of other compounds of the invention for the treatment of eye diseases in any way.

From the disclosed data, it will indeed be appreciated that compounds 14 or 17 combine the required properties for the treatment of ROCK-associated eye diseases. As disclosed in point C1.1, compounds 14 and 17 possess strong inhibitory activity against ROCK. As disclosed in point C1.4, they display functional activity in the MLC phosphorylation assay. As disclosed in point C.2.1, they have a short half life in plasma. As disclosed in point C.2.3, they have a significantly longer half-life in aqueous humor than in plasma. Additionally, upon ester hydrolysis by esterases, compounds 14 and 17 yield compound Met1. As disclosed in point C.1.4, this predictable metabolite resulting from the rapid degradation of compounds 14 or 17 in blood/plasma is devoid of functional activity.

C3.2: Soft ROCK Inhibitors for Lung Diseases

Compounds of the invention qualify as soft ROCK inhibitors for the treatment of ROCK-associated lung diseases. They display good inhibitory potency against ROCK, functional activity in cellular assay(s), low stability in systemic circulation, and good stability in the lung. Furthermore, they are converted into a predictable species, displaying negligible functional activity.

A detailed example of soft ROCK inhibitors for the treatment of lung diseases is provided by compounds such 26 or 28. This example does not limit the applicability of other compounds of the invention for the treatment of lung diseases in any way.

From the disclosed data, it will indeed be appreciated that compounds 26 or 28 combine the required properties for the treatment of ROCK-associated lung diseases. As disclosed in point C1.1, these compounds possess strong inhibitory activity against ROCK. As disclosed in point C1.4, they display functional activity in the MLC phosphorylation assay. As disclosed in point C.2.1, they have a short half life in plasma. As disclosed in point C.2.2, they have a significantly longer half-life in lung tissue (>240 min) than in plasma.

C3.3: Comparison to Structurally Related Compounds

Compared to structurally similar prior art known ROCK inhibitors, such as for example described in WO2008/077057, WO2010/065782, WO2009/158587, US2009/0325960, US2009/0325959, Iwakubo et al. (*Bioorg. Med. Chem.*, 2007, 15, 350-364 & *Bioorg. Med. Chem.*, 2007, 15, 1022-1033) and WO2001/56988, the compounds of the present invention differ in that they are very rapidly converted into predictable, functionally inactive compounds when entering systemic circulation, yet retain good stability in target organs. While the above-mentioned documents disclose ROCK inhibitors that are structurally similar to the compounds of this invention, none of these documents discusses the design, discovery or potential advantages of soft ROCK inhibitors. In particular, no information is provided regarding the stability of the disclosed ROCK inhibitors in plasma, whole blood, or in potential target organs.

In view of the structural similarity between some compounds from the above-mentioned documents and compounds of the present invention, comparison is here provided with compounds 1.091 and 1.060, which are present in documents WO2008/077057, WO2009/158587, WO2010/065782, US2009/0325960, and US2009/0325959. In particular, compound 1.091 and 1.060 are cited as preferred compounds in document WO2008/077057 (see claim 6), which puts considerable emphasis on the treatment of eye diseases. Compound 1.091 is further cited as a preferred compound in documents WO2009/158587 (see claims 5) and WO2010/065782 (see claim 15), which put considerable emphasis on the treatment of lung diseases, including COPD. Furthermore, compound 1.200 is a chirally pure isomer of the compound 1.060, which is described as racemate, and is further described as a preferred compound in document WO2010/065782. In view of their potent activity, and status of preferred compounds for the treatment of pathologies that are discussed in the present document, it will be appreciated that these compounds constitute appropriate references for comparison.

| Compound | 14 | 26 | 32 | 1.091 | 1.060 |
|---|---|---|---|---|---|
| IC$_{50}$ ROCK2 (nM) | 3.4 | 1.9 | 25 | 2.4 | 7.0 |
| IC$_{50}$ MLC-PP (nM) | 240 | 400 | 160 | 110 | ND |
| t$_{1/2}$ Plasma (min) | <5 | <5 | 22 | >120* | <5 |
| t$_{1/2}$ AH (min) | >120 | ND | 98 | >120 | <5 |
| t$_{1/2}$ lung S9 (min) | 9 | >240 | >240 | >240 | <5 |

From this data, it will be appreciated that both compounds of the invention and prior art compounds 1.091 and 1.060 display comparable on-target (ROCK2) and functional (MLC-PP) activity. It will therefore be acknowledged that optimization of the compounds of this invention into soft ROCK inhibitors did not compromise their functional activity in any way.

Compound 1.091 represents a typical non-soft ROCK inhibitor that is not recognized as a substrate by carboxylic ester hydrolases. As such, this compound fails to solve the technical problem of providing a soft ROCK inhibitor with strong on-target and functional activity, good stability in the target organ, and low stability in the systemic circulation. More in particular, compound 1.091 is not degraded at a significant rate in any of the tested media, including plasma. The compound will therefore not be readily degraded when entering the blood flow, resulting in potential systemic exposure.

Compound 1.060 represents, within the above-mentioned documents, an example of ester derivative designated as a preferred compound. Although this compound is disclosed in a document emphasizing the potential of ROCK inhibitors for the treatment of eye diseases, we hereby demonstrate that this compound displays very low stability (t$_{1/2}$<5 min) in all tested media, including aqueous humor. As a result, 1.060 is unlikely to achieve and maintain a pharmacologically relevant concentration in aqueous humor for a sustained period of time. This compound therefore fails to solve the technical problem of providing a soft ROCK inhibitor with strong on-target and functional activity, good stability in the target organ, and low stability in the systemic circulation. In particular, the very low stability of compound 1.060 in lung or aqueous humor makes it unsuitable for the treatment of lung diseases or eye diseases.

It will therefore be appreciated that prior art compounds such as 1.060 or 1.091 do not solve the technical problem of providing a ROCK inhibitor with strong on-target and functional activity, high stability in the target organ, and low stability in the systemic circulation. As a result, these compounds differ in their pharmacological profile from the compounds of this invention, which represent soft ROCK inhibitors.

The invention claimed is:

1. A compound of Formula I or a stereoisomer, tautomer, racemic, salt, hydrate, or solvate thereof,

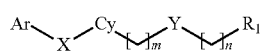

(I)

wherein
X is oxygen, —NH—, or a direct bond;
Y is —NH— or a direct bond;
n is an integer from 0 to 4;
m is an integer from 0 to 4;
Cy represents a bivalent radical consisting of a saturated (poly)cycle selected from the group consisting of:

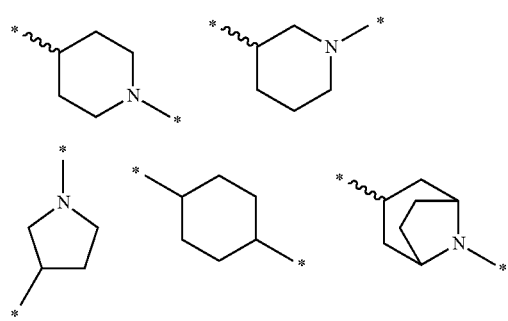

Ar is selected from the group comprising:

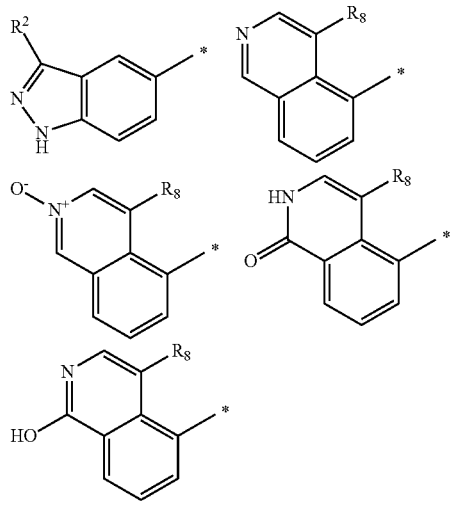

wherein $R^2$ is hydrogen or methyl; and
$R^8$ is hydrogen, methyl, halogen, or alkynyl;
$R^1$ is an aryl or heteroaryl optionally substituted with halo or $C_{1-6}$alkyl; wherein said aryl or heteroaryl is substituted with —$(CH_2)_p$—C(=O)—$NR^3R^4$;
wherein
p is an integer from 0 to 3
$Het^1$ is selected from the group consisting of:

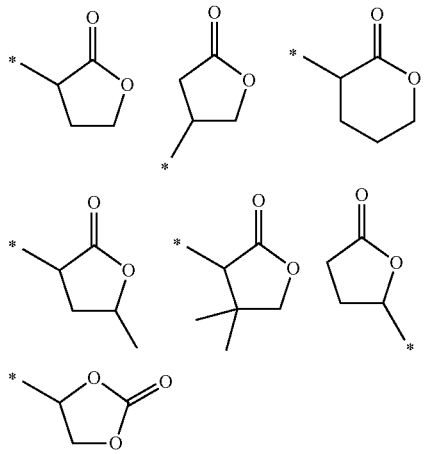

$R^3$ is selected from the group consisting of $Het^1$, $C_{1-20}$alkyl, aryl or heteroaryl; wherein said $C_{1-20}$alkyl, aryl or heteroaryl is substituted with 1, 2 or 3 substituents each independently selected from the group consisting of aryl, heteroaryl, —$(CH_2)_p$—C(=O)—$OR^{21}$, -$Het^1$, —NH-$Het^1$, —O-$Het^1$, —S-$Het^1$, —S—$C_{2-6}$alkyl, —NH—$C_{2-6}$alkyl, and —O—$C_{2-6}$alkyl;
wherein said aryl, heteroaryl, —O—$C_{2-6}$alkyl, —NH—$C_{2-6}$alkyl, or —S—$C_{2-6}$alkyl are each independently substituted with a substituent selected from the group consisting of C(=O)—$OR^{21}$, -$Het^1$, —O-$Het^1$, —NH-$Het^1$, and —S-$Het^1$; and
$R^4$ is selected from the group consisting of hydrogen or $C_{1-6}$alkyl; or
$R^3$ and $R^4$ together with the nitrogen atom to which they are attached form a heterocycle substituted with one substituent selected from the group consisting of $C_{1-20}$alkyl, aryl or heteroaryl; wherein said $C_{1-20}$alkyl, aryl, or heteroaryl is substituted with 1, 2 or 3 substituents each independently selected from the group consisting of aryl, heteroaryl, —C(=O)—$OR^{21}$, -$Het^1$, —O-$Het^1$, —S-$Het^1$, —S—$C_{2-6}$alkyl, —NH—$C_{2-6}$alkyl, and —O—$C_{2-6}$alkyl;
wherein said —O—$C_{2-6}$alkyl, —NH—$C_{2-6}$alkyl, or —S—$C_{2-6}$alkyl are each independently substituted with a substituent selected from the group consisting of C(=O)—$OR^{21}$, -$Het^1$, —O-$Het^1$, —NH-$Het^1$, and —S-$Het^1$; and
$R^{21}$ is selected from the group consisting of optionally substituted $C_{1-20}$alkyl, optionally substituted $C_{1-20}$alkenyl, optionally substituted $C_{1-20}$alkynyl, optionally substituted $C_{3-15}$cycloalkyl, optionally substituted aryl, optionally substituted heterocyclyl, and optionally substituted heteroaryl.

2. A compound according to claim 1 wherein X is oxygen or NH.

3. A compound according to claim 1 wherein
X is oxygen, —NH—, or a direct bond;
Y is —NH— or a direct bond;
n is an integer from 0 to 4;
m is an integer from 0 to 4;
Cy is selected from the group consisting of:

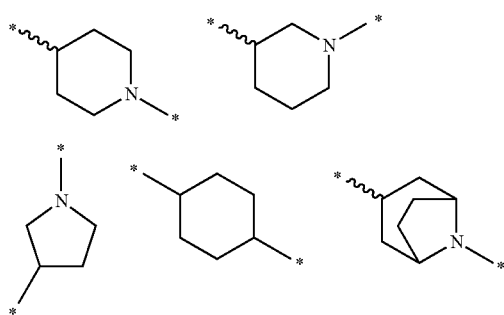

Ar is selected from the group comprising:

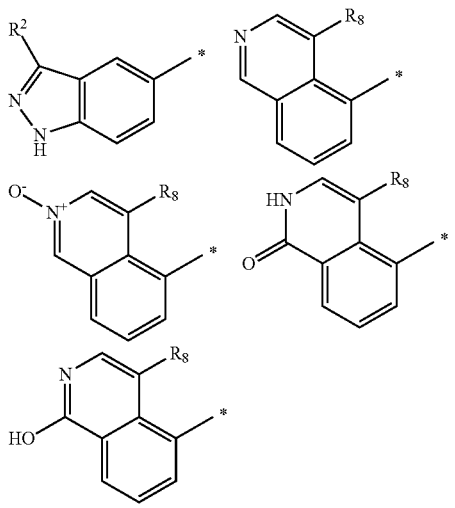

$R^2$ is hydrogen or methyl;
$R^8$ is hydrogen, methyl, halogen, or alkynyl;
$R^1$ is an aryl or heteroaryl optionally substituted with halo or $C_{1-6}$alkyl; wherein said aryl or heteroaryl is substituted with —$(CH_2)_p$—C(=O)—$NR^3R^4$;
wherein
p is an integer from 0 to 3
$Het^1$ is selected from the group consisting of:

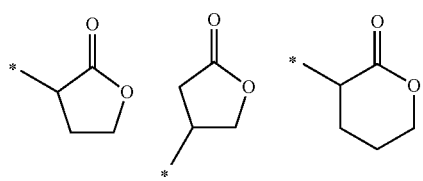

-continued

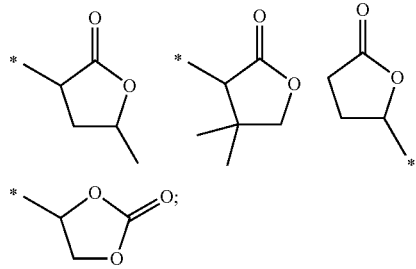

$R^3$ is selected from the group consisting of $Het^1$, $C_{1-20}$alkyl, aryl or heteroaryl; wherein said $C_{1-20}$alkyl, aryl or heteroaryl is substituted with 1, 2 or 3 substituents each independently selected from the group consisting of aryl, heteroaryl, —$(CH_2)_p$—C(=O)—$OR^{21}$, -$Het^1$, —NH-$Het^1$, —O-$Het^1$, —S-$Het^1$, —S—$C_{2-6}$alkyl, —NH—$C_{2-6}$alkyl, and —O—$C_{2-6}$alkyl;

Wherein said aryl, heteroaryl, —O—$C_{2-6}$alkyl, —NH—$C_{2-6}$alkyl, or —S—$C_{2-6}$alkyl are each independently substituted with a substituent selected from the group consisting of C(=O)—$OR^{21}$, -$Het^1$, —O-$Het^1$, —NH-$Het^1$, and —S-$Het^1$; and $R^4$ is selected from the group consisting of hydrogen or $C_{1-6}$alkyl; or $R^3$ and $R^4$ together with the nitrogen atom to which they are attached form a heterocycle substituted with one substituent selected from the group consisting of $C_{1-20}$alkyl, aryl or heteroaryl; wherein said $C_{1-20}$alkyl, aryl, or heteroaryl is substituted with 1, 2 or 3 substituents each independently selected from the group consisting of aryl, heteroaryl, —C(=O)—$OR^{21}$, -$Het^1$, —O-$Het^1$, —S-$Het^1$, —S—$C_{2-6}$alkyl, —NH—$C_{2-6}$alkyl, and —O—$C_{2-6}$alkyl;

wherein said —O—$C_{2-6}$alkyl, —NH—$C_{2-6}$alkyl, or —S—$C_{2-6}$alkyl are each independently substituted with a substituent selected from the group consisting of C(=O)—$OR^{21}$, -$Het^1$, —O-$Het^1$, —NH-$Het^1$, and —S-$Het^1$; and $R^{21}$ is selected from the group consisting of optionally substituted $C_{1-20}$alkyl, optionally substituted $C_{1-20}$alkenyl, optionally substituted $C_{1-20}$alkynyl, optionally substituted $C_{3-15}$cycloalkyl, optionally substituted aryl, optionally substituted heterocyclyl, and optionally substituted heteroaryl.

4. A compound according to claim 1, wherein
$R^1$ is aryl or heteroaryl substituted with —$(CH_2)_p$—C(=O)—$NR^3R^4$.

5. A compound according to claim 1, wherein
$R^1$ is phenyl, pyrrolyl or thiophenyl substituted with —$(CH_2)_p$—C(=O)—$NR^3R^4$.

6. A compound according to claim 1, wherein
Cy represents a bivalent radical selected from the group consisting of:

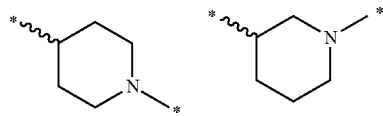

-continued

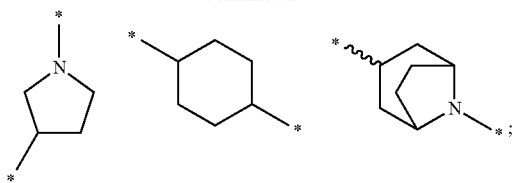

and
Ar is selected from the group consisting of:

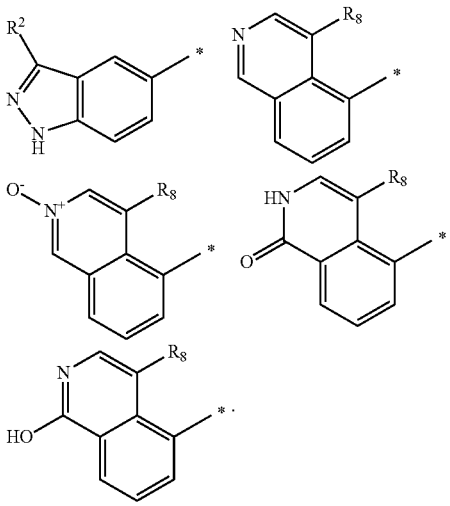

7. A compound according to claim 1 wherein at least one of the following apply:
X is oxygen, —NH— or a direct bond;
Y is —NH— or a direct bond;
n is an integer from 0 to 4;
m is an integer from 0 to 4;
Cy is selected from the group consisting of:

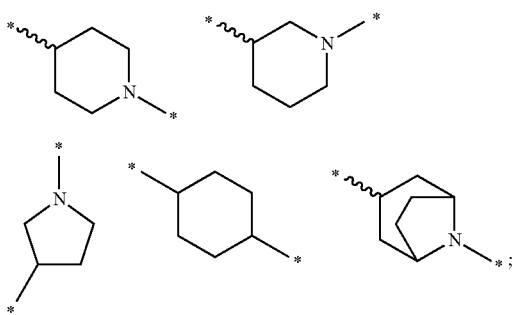

Ar is selected from the group consisting of:

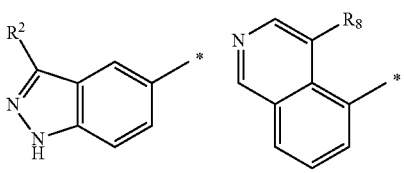

-continued

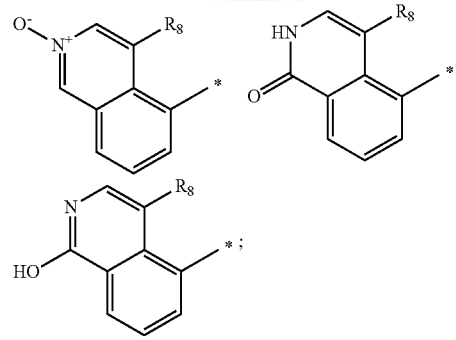

$R^2$ is hydrogen or methyl;
$R^8$ is hydrogen, methyl, halogen, or alkynyl;
$R^1$ is an aryl or heteroaryl optionally substituted with halo or $C_{1-6}$alkyl; wherein said aryl or heteroaryl is substituted with —$(CH_2)_p$—C(=O)—$NR^3R^4$;
p is an integer from 0 to 3;
$Het^1$ is selected from the group consisting of:

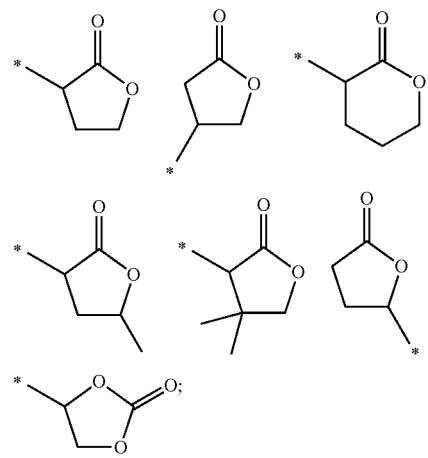

$R^{21}$ is selected from the group consisting of optionally substituted $C_{1-20}$alkyl, optionally substituted $C_{1-20}$alkenyl, optionally substituted $C_{1-20}$alkynyl, optionally substituted $C_{3-15}$cycloalkyl, optionally substituted aryl, optionally substituted heterocyclyl, and optionally substituted heteroaryl;
$R^3$ is selected from the group consisting of $Het^1$, $C_{1-20}$alkyl, aryl or heteroaryl; wherein said $C_{1-20}$alkyl, aryl or heteroaryl is substituted with 1, 2 or 3 substituents each independently selected from the group consisting of aryl, heteroaryl, —$(CH_2)_p$—C(=O)—$OR^{21}$, -$Het^1$, —NH-$Het^1$, —O-$Het^1$, —S-$Het^1$, —S—$C_{2-6}$alkyl, —NH—$C_{2-6}$alkyl, and —O—$C_{2-6}$alkyl;
Wherein said aryl, heteroaryl, —O—$C_{2-6}$alkyl, —NH—$C_{2-6}$alkyl, or —S—$C_{2-6}$alkyl are each independently substituted with a substituent selected from the group consisting of C(=O)—$OR^{21}$, -$Het^1$, —O-$Het^1$, —NH-$Het^1$, and —S-$Het^1$;
$R^4$ is selected from the group consisting of hydrogen or $C_{1-6}$alkyl;
$R^3$ and $R^4$ together with the nitrogen atom to which they are attached form a heterocycle substituted with one substituent selected from the group consisting of $C_{1-20}$alkyl, aryl or heteroaryl; wherein said $C_{1-20}$alkyl, aryl, or heteroaryl is substituted with 1, 2 or 3 substituents each independently selected from the group consisting of aryl, heteroaryl, —C(=O)—OR$^{21}$, -Het$^1$, —O-Het$^1$, —S-Het$^1$, —S—C$_{2-6}$alkyl, —NH—C$_{2-6}$alkyl, and —O—C$_{2-6}$alkyl;

wherein said —O—C$_{2-6}$alkyl, —NH—C$_{2-6}$alkyl, or —S—C$_{2-6}$alkyl are each independently substituted with a substituent selected from the group consisting of C(=O)—OR$^{21}$, -Het$^1$, —O-Het$^1$, —NH-Het$^1$, and —S-Het$^1$;

with the proviso that:

R$^3$ and R$^4$ cannot be taken together with the nitrogen atom to which they are attached to form a heterocycle;

R$^1$ cannot be selected from indolyl;

if R$^1$ is phenyl, then said phenyl is substituted in the meta position.

8. A pharmaceutical composition comprising a compound as defined in claim 1 and a pharmaceutically acceptable carrier.

9. A method for the treatment of at least one disease or disorder selected from the group comprising eye diseases; lung diseases; and intestinal diseases; said method comprising administering to a subject in need thereof a therapeutic effective amount of a compound as defined in claim 1.

10. A method for the treatment of an eye disease selected from the group consisting of retinopathy, optic neuropathy, glaucoma, inflammatory eye diseases and degenerative retinal diseases; said method comprising administering to a subject in need thereof a therapeutic effective amount of a compound as defined in claim 1.

11. A method for the treatment of a lung disease selected from the group consisting of pulmonary fibrosis, emphysema, chronic bronchitis, asthma, fibrosis, pneumonia, cystic fibrosis, chronic obstructive pulmonary disease (COPD), bronchitis rhinitis, and respiratory distress syndrome; said method comprising administering to a subject in need thereof a therapeutic effective amount of a compound as defined in claim 1.

12. A method for the treatment of an intestinal disease selected from the group consisting of inflammatory bowel disease (IBD), colitis, gastroenteritis, ileus, ileitis, appendicitis and Crohn's disease; said method comprising administering to a subject in need thereof a therapeutic effective amount of a compound as defined in claim 1.

13. A method for inhibiting a Rho kinase in a subject, comprising administering a compound of claim 1 to said subject.

* * * * *